United States Patent
Desai et al.

(10) Patent No.: US 9,663,517 B2
(45) Date of Patent: May 30, 2017

(54) COMPOSITIONS AND USES THEREOF

(71) Applicants: Plexxikon Inc., Berkeley, CA (US); Hoffman-La Roche Inc., Nutley, NJ (US)

(72) Inventors: Dipen Desai, Whippany, NJ (US); Ralph Diodone, Breisach (DE); Zenaida Go, Clifton, NJ (US); Prabha N. Ibrahim, Mountain View, CA (US); Raman Iyer, Piscataway, NJ (US); Hans-Juergen Mair, Loerrach (DE); Harpreet K. Sandhu, West Orange, NJ (US); Navnit H. Shah, Clifton, NJ (US); Gary Visor, Castro Valley, CA (US); Nicole Wyttenbach, Sissach (CH); Stephan Lauper, Kaiseraugst (CH); Johannes Pudewell, Oberwil (CH); Frank Wierschem, Rheinfelden (CH)

(73) Assignees: Plexxikon Inc., Berkeley, CA (US); Hoffman-La Roche Inc., Nutley, NJ (US)

(*) Notice: Subject to any disclaimer, the term of this patent is extended or adjusted under 35 U.S.C. 154(b) by 0 days.

(21) Appl. No.: 15/241,773

(22) Filed: Aug. 19, 2016

(65) Prior Publication Data
US 2016/0355513 A1 Dec. 8, 2016

Related U.S. Application Data

(62) Division of application No. 12/752,035, filed on Mar. 31, 2010, now Pat. No. 9,447,089.

(60) Provisional application No. 61/166,677, filed on Apr. 3, 2009, provisional application No. 61/176,051, filed on May 6, 2009.

(30) Foreign Application Priority Data

Nov. 11, 2009 (EP) ..................... 09175665

(51) Int. Cl.
| A61K 9/14 | (2006.01) |
| C07D 471/04 | (2006.01) |
| A61K 31/437 | (2006.01) |
| A61K 9/10 | (2006.01) |
| A61K 9/16 | (2006.01) |
| A61K 9/00 | (2006.01) |

(52) U.S. Cl.
CPC ............ *C07D 471/04* (2013.01); *A61K 9/10* (2013.01); *A61K 9/1635* (2013.01); *A61K 9/1652* (2013.01); *A61K 31/437* (2013.01); *A61K 9/0014* (2013.01); *A61K 9/0019* (2013.01); *C07B 2200/13* (2013.01)

(58) Field of Classification Search
None
See application file for complete search history.

(56) References Cited

U.S. PATENT DOCUMENTS

| 2,234,705 | A | 3/1941 | Normington et al. |
| 2,413,258 | A | 12/1946 | Soday et al. |
| 4,150,949 | A | 4/1979 | Smith |
| 4,301,159 | A | 11/1981 | Ogata et al. |
| 4,439,444 | A | 3/1984 | Nisato et al. |
| 4,568,649 | A | 2/1986 | Bertoglio-Matte |
| 4,595,780 | A | 6/1986 | Ogata et al. |
| 4,626,513 | A | 12/1986 | Burton et al. |
| 4,634,701 | A | 1/1987 | De Vincentiis |
| 4,714,693 | A | 12/1987 | Targos |
| 4,727,395 | A | 2/1988 | Oda et al. |
| 4,863,945 | A | 9/1989 | Friebe et al. |
| 5,120,782 | A | 6/1992 | Hubsch et al. |
| 5,143,854 | A | 9/1992 | Pirrung et al. |
| 5,338,849 | A | 8/1994 | Festal et al. |
| 5,360,882 | A | 11/1994 | Dougherty et al. |
| 5,426,039 | A | 6/1995 | Wallace et al. |
| 5,432,177 | A | 7/1995 | Baker et al. |
| 5,434,049 | A | 7/1995 | Okano et al. |
| 5,449,614 | A | 9/1995 | Danos et al. |
| 5,474,935 | A | 12/1995 | Chatterjee et al. |
| 5,486,525 | A | 1/1996 | Summers et al. |
| 5,556,752 | A | 9/1996 | Lockhart et al. |
| 5,576,319 | A | 11/1996 | Baker et al. |
| 5,580,859 | A | 12/1996 | Felgner et al. |
| 5,631,236 | A | 5/1997 | Woo et al. |
| 5,632,957 | A | 5/1997 | Heller et al. |
| 5,658,775 | A | 8/1997 | Gilboa |
| 5,681,959 | A | 10/1997 | Bishop et al. |
| 5,700,637 | A | 12/1997 | Southern |
| 5,700,809 | A | 12/1997 | Leeson et al. |
| 5,712,285 | A | 1/1998 | Curtis et al. |
| 5,721,118 | A | 2/1998 | Scheffler |
| 5,744,305 | A | 4/1998 | Fodor et al. |

(Continued)

FOREIGN PATENT DOCUMENTS

| CA | 2550361 | 7/2005 |
| CL | 15952006 | 6/2006 |

(Continued)

OTHER PUBLICATIONS

U.S. Appl. No. 61/054,445, filed May 19, 2008, Ibrahim et al.
U.S. Appl. No. 61/060,418, filed Jun. 10, 2008, Ibrahim et al.
Abou-Khalil, et al., "Delayed bone regeneration is linked to chronic inflammation in murine muscular dystrophy," J. Bone Miner. Res., (2013), DOI 10.1002/jbmr.2038.
Ahmad, "BRAF mutation common to 70% of thyroid carcinomas," The Lancet, Oncology, (2003), 4:330.
Alfthan, "Surface Plasmon Resonance Biosensors as a Tool in Antibody Engineering", Biosensors & Bioelectronics 13:653-663 (1998).
Allegretti, et al., Palladium-Catalysed Functionalisation at 4- and 6- Position of the 7-Azaindole System, Synlett 5:609-612 (2001).
Al-Obeidi, et al., Peptide and Peptidomimetic Libraries, Mol Biotechnol 9:205-223, 1998.
Alvarez, et al., Synthesis of 3-Aryl- and 3-Heteroaryl-7-Azaindoles, Synthesis 4:615-620 (1999).
Amersdorfer, et al., Phage Libraries for Generation of Anti-Botulinum scFv Antibodies, Methods in Molecular Biology 145:219-240, 2000.

(Continued)

*Primary Examiner* — Robert A Wax
*Assistant Examiner* — Randeep Singh
(74) *Attorney, Agent, or Firm* — Sheppard Mullin Richter & Hampton LLP

(57) ABSTRACT

Provided are solid dispersions, solid molecular complexes, salts and crystalline polymorphs involving propane-1-sulfonic acid {3-[5-(4-chloro-phenyl)-1H-pyrrolo[2,3-b]pyridine-3-carbonyl]-2,4-difluoro-phenyl}-amide.

5 Claims, 8 Drawing Sheets

(56) References Cited

U.S. PATENT DOCUMENTS

| | | |
|---|---|---|
| 5,747,276 A | 5/1998 | Hoch et al. |
| 5,763,198 A | 6/1998 | Hirth et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,858,995 A | 1/1999 | Kawai et al. |
| 5,877,007 A | 3/1999 | Housey |
| 5,908,401 A | 6/1999 | Henley |
| 5,952,362 A | 9/1999 | Cournoyer et al. |
| 5,958,930 A | 9/1999 | Gangjee |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pedersen et al. |
| 6,110,456 A | 8/2000 | During |
| 6,110,458 A | 8/2000 | Freeman et al. |
| 6,113,913 A | 9/2000 | Brough et al. |
| 6,117,681 A | 9/2000 | Salmons et al. |
| 6,161,776 A | 12/2000 | Byles |
| 6,178,384 B1 | 1/2001 | Kolossvary |
| 6,235,769 B1 | 5/2001 | Clary |
| 6,243,980 B1 | 6/2001 | Bronstein et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,288,234 B1 | 9/2001 | Griffin |
| 6,294,330 B1 | 9/2001 | Michnick et al. |
| 6,310,074 B1 | 10/2001 | Depreux et al. |
| 6,350,786 B1 | 2/2002 | Albano et al. |
| 6,545,014 B2 | 4/2003 | Verner |
| 6,653,309 B1 | 11/2003 | Saunders et al. |
| 6,858,860 B2 | 2/2005 | Hosono et al. |
| 6,897,207 B2 | 5/2005 | Cox et al. |
| 7,259,165 B2 | 8/2007 | Bernotas et al. |
| 7,271,262 B2 | 9/2007 | La Greca et al. |
| 7,361,763 B2 | 4/2008 | Arnold et al. |
| 7,361,764 B2 | 4/2008 | Arnold et al. |
| 7,452,993 B2 | 11/2008 | Arnold et al. |
| 7,498,342 B2 | 3/2009 | Ibrahim et al. |
| 7,504,509 B2 | 3/2009 | Ibrahim et al. |
| 7,582,637 B2 | 9/2009 | Arnold et al. |
| 7,601,839 B2 | 10/2009 | Arnold et al. |
| 7,626,021 B2 | 12/2009 | Arnold et al. |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,893,075 B2 | 2/2011 | Zhang et al. |
| 7,947,708 B2 | 5/2011 | Ibrahim et al. |
| 7,994,185 B2 | 8/2011 | Rheault |
| 8,067,638 B2 | 11/2011 | Kai et al. |
| 8,129,404 B2 | 3/2012 | Ibrahim et al. |
| 8,143,271 B2 | 3/2012 | Ibrahim et al. |
| 8,404,700 B2 | 3/2013 | Ibrahim et al. |
| 8,415,469 B2 | 4/2013 | Ibrahim et al. |
| 2001/0001449 A1 | 5/2001 | Kiliany et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2003/0003004 A1 | 1/2003 | Stones et al. |
| 2003/0219489 A1 | 11/2003 | Curatolo et al. |
| 2004/0002534 A1 | 1/2004 | Lipson et al. |
| 2004/0067257 A1 | 4/2004 | Bateman et al. |
| 2004/0073274 A1 | 4/2004 | Cook et al. |
| 2004/0077595 A1 | 4/2004 | Cheng et al. |
| 2004/0142864 A1 | 7/2004 | Bremer et al. |
| 2004/0167030 A1 | 8/2004 | Bernotas et al. |
| 2004/0171062 A1 | 9/2004 | Hirth et al. |
| 2005/0026792 A1 | 2/2005 | Cartwright |
| 2005/0031692 A1 | 2/2005 | Beyerinck et al. |
| 2005/0085463 A1 | 4/2005 | Weiner et al. |
| 2005/0154014 A1 | 7/2005 | Bloxham et al. |
| 2005/0164300 A1 | 7/2005 | Artis et al. |
| 2005/0170431 A1 | 8/2005 | Ibrahim et al. |
| 2005/0256151 A1 | 11/2005 | Salom et al. |
| 2006/0018726 A1 | 1/2006 | Hall |
| 2006/0024361 A1 | 2/2006 | Odidi et al. |
| 2006/0035898 A1 | 2/2006 | Arnold et al. |
| 2006/0058324 A1 | 3/2006 | Capraro et al. |
| 2006/0058339 A1 | 3/2006 | Ibrahim et al. |
| 2006/0058340 A1 | 3/2006 | Ibrahim et al. |
| 2006/0167403 A1 | 7/2006 | Henley et al. |
| 2007/0032519 A1 | 2/2007 | Zhang et al. |
| 2007/0049615 A1 | 3/2007 | Ibrahim et al. |
| 2007/0054963 A1 | 3/2007 | Lifshitz-Liron et al. |
| 2007/0072862 A1 | 3/2007 | Dimauro et al. |
| 2007/0161666 A1 | 7/2007 | Blumenkopf et al. |
| 2007/0218138 A1 | 9/2007 | Bittorf et al. |
| 2007/0225306 A1 | 9/2007 | Choi et al. |
| 2007/0287711 A1 | 12/2007 | Arnold et al. |
| 2008/0004661 A1 | 1/2008 | Silverstone |
| 2008/0079906 A1 | 4/2008 | Finn |
| 2008/0167338 A1 | 7/2008 | Spevak et al. |
| 2008/0188514 A1 | 8/2008 | Wu et al. |
| 2009/0005356 A1 | 1/2009 | Blaney et al. |
| 2009/0076046 A1 | 3/2009 | Zhang et al. |
| 2009/0143352 A1 | 6/2009 | Arnold et al. |
| 2009/0286783 A1 | 11/2009 | Ibrahim et al. |
| 2009/0306056 A1 | 12/2009 | Arnold et al. |
| 2009/0306086 A1 | 12/2009 | Ibrahim et al. |
| 2009/0306087 A1 | 12/2009 | Ibrahim et al. |
| 2010/0286142 A1 | 11/2010 | Ibrahim et al. |
| 2010/0286178 A1 | 11/2010 | Ibrahim et al. |
| 2011/0028511 A1 | 2/2011 | Hildbrand et al. |
| 2011/0092538 A1 | 4/2011 | Spevak et al. |
| 2011/0112127 A1 | 5/2011 | Zhang et al. |
| 2011/0112136 A1 | 5/2011 | Diodone et al. |
| 2011/0152258 A1 | 6/2011 | Ibrahim et al. |
| 2011/0183988 A1 | 7/2011 | Ibrahim et al. |
| 2012/0053177 A1 | 3/2012 | Ibrahim et al. |
| 2012/0165366 A1 | 6/2012 | Ibrahim et al. |
| 2012/0245174 A1 | 9/2012 | Ibrahim et al. |
| 2013/0172375 A1 | 7/2013 | Albano et al. |
| 2013/0261117 A1 | 10/2013 | Ibrahim et al. |
| 2013/0274259 A1 | 10/2013 | Zhang et al. |
| 2013/0303534 A1 | 11/2013 | Ibrahim et al. |
| 2014/0028373 A1 | 1/2014 | Voelker et al. |
| 2014/0037617 A1 | 2/2014 | Bollag et al. |
| 2014/0094611 A1 | 4/2014 | Ibrahim et al. |
| 2014/0128373 A1 | 5/2014 | Ibrahim et al. |
| 2014/0243365 A1 | 8/2014 | Zhang et al. |
| 2014/0288070 A1 | 9/2014 | Ibrahim et al. |

FOREIGN PATENT DOCUMENTS

| | | |
|---|---|---|
| DE | 2413258 | 1/1975 |
| EP | 0344603 | 5/1989 |
| EP | 0154734 | 8/1990 |
| EP | 0465970 | 1/1992 |
| EP | 0580860 | 4/1992 |
| EP | 0901786 | 7/1998 |
| EP | 0596406 | 12/1998 |
| EP | 0988863 | 3/2000 |
| EP | 1057826 | 12/2000 |
| EP | 1368001 | 2/2002 |
| EP | 0870768 | 5/2002 |
| EP | 1267111 | 12/2002 |
| EP | 1388541 | 2/2004 |
| EP | 1749829 | 2/2007 |
| EP | 2036990 | 4/2014 |

(56) References Cited

FOREIGN PATENT DOCUMENTS

| | | |
|---|---|---|
| FR | 2264804 | 10/1975 |
| GB | 1 198 301 A | 5/1973 |
| GB | 2 292 143 | 2/1996 |
| GB | 2 292 145 | 2/1996 |
| GB | 2 298 198 | 8/1996 |
| GB | 2 299 581 | 10/1996 |
| JP | 06-135946 | 5/1994 |
| JP | 10-087629 | 4/1998 |
| JP | 10-130269 | 5/1998 |
| JP | 2000-95708 A | 4/2000 |
| JP | 2001-278886 | 10/2001 |
| JP | 15-073357 | 3/2003 |
| WO | WO-93/13099 | 7/1993 |
| WO | WO-94/14808 | 7/1994 |
| WO | WO-94/20459 | 9/1994 |
| WO | WO-94/20497 | 9/1994 |
| WO | WO-95/04742 | 2/1995 |
| WO | WO-95/07910 | 3/1995 |
| WO | WO-95/28387 | 10/1995 |
| WO | WO-96/00226 | 1/1996 |
| WO | WO-96/11929 | 2/1996 |
| WO | WO-96/05200 | 4/1996 |
| WO | WO-96/17958 | 6/1996 |
| WO | WO-96/18738 | 6/1996 |
| WO | WO-96/38131 | 12/1996 |
| WO | WO-97/03967 | 2/1997 |
| WO | WO-97/46313 | 12/1997 |
| WO | WO-97/46558 | 12/1997 |
| WO | WO-97/49703 | 12/1997 |
| WO | WO-98/06433 | 2/1998 |
| WO | WO-98/22457 | 5/1998 |
| WO | WO-98/47899 | 10/1998 |
| WO | WO-99/00386 | 1/1999 |
| WO | WO-99/09217 | 2/1999 |
| WO | WO-99/32106 | 7/1999 |
| WO | WO-99/32433 | 7/1999 |
| WO | WO-99/51231 | 10/1999 |
| WO | WO-99/51232 | 10/1999 |
| WO | WO-99/51233 | 10/1999 |
| WO | WO-99/51234 | 10/1999 |
| WO | WO-99/51595 | 10/1999 |
| WO | WO-99/51596 | 10/1999 |
| WO | WO-99/51773 | 10/1999 |
| WO | WO-00/09162 | 2/2000 |
| WO | WO-00/12074 | 3/2000 |
| WO | WO-00/12514 | 3/2000 |
| WO | WO-00/17202 | 3/2000 |
| WO | WO-00/29411 | 5/2000 |
| WO | WO-00/53582 | 9/2000 |
| WO | WO-00/55153 | 9/2000 |
| WO | WO-00/64898 | 11/2000 |
| WO | WO-00/71506 | 11/2000 |
| WO | WO-00/71537 | 11/2000 |
| WO | WO-00/75139 | 12/2000 |
| WO | WO-01/09121 | 2/2001 |
| WO | WO-01/24236 | 4/2001 |
| WO | WO-01/29036 | 4/2001 |
| WO | WO-01/46196 | 6/2001 |
| WO | WO-01/60822 | 8/2001 |
| WO | WO-01/62255 | 8/2001 |
| WO | WO-01/74786 | 11/2001 |
| WO | WO-01/98299 | 12/2001 |
| WO | WO-02/00657 | 1/2002 |
| WO | WO-02/18346 | 3/2002 |
| WO | WO-02/078780 | 10/2002 |
| WO | WO-02/083175 | 10/2002 |
| WO | WO-02/085896 | 10/2002 |
| WO | WO-02/102783 | 12/2002 |
| WO | WO-03/000258 | 1/2003 |
| WO | WO-03/000267 | 1/2003 |
| WO | WO-03/003004 | 1/2003 |
| WO | WO-03/004472 | 1/2003 |
| WO | WO-03/006459 | 1/2003 |
| WO | WO-03/008422 | 1/2003 |
| WO | WO-03/011868 | 2/2003 |
| WO | WO-03/020698 | 3/2003 |
| WO | WO-03/028724 | 4/2003 |
| WO | WO-03/037862 | 5/2003 |
| WO | WO-03/051838 | 6/2003 |
| WO | WO-03/064413 | 8/2003 |
| WO | WO-03/068221 | 8/2003 |
| WO | WO-03/082289 | 10/2003 |
| WO | WO-03/082868 | 10/2003 |
| WO | WO-03/082869 | 10/2003 |
| WO | WO-03/087087 | 10/2003 |
| WO | WO-03/062236 | 12/2003 |
| WO | WO-03/101990 | 12/2003 |
| WO | WO-2004/005283 | 1/2004 |
| WO | WO-2004/009600 | 1/2004 |
| WO | WO-2004/009601 | 1/2004 |
| WO | WO-2004/014369 | 2/2004 |
| WO | WO-2004/016609 | 2/2004 |
| WO | WO-2004/016610 | 2/2004 |
| WO | WO-2004/024895 | 3/2004 |
| WO | WO-2004/052880 | 6/2004 |
| WO | WO-2004/054581 | 7/2004 |
| WO | WO-2004/056830 | 7/2004 |
| WO | WO-2004/065393 | 8/2004 |
| WO | WO-2004/065394 | 8/2004 |
| WO | WO-2004/069138 | 8/2004 |
| WO | WO-2004/054974 | 9/2004 |
| WO | WO-2004/074278 | 9/2004 |
| WO | WO-2004/074286 | 9/2004 |
| WO | WO-2004/078756 | 9/2004 |
| WO | WO-2004/078923 | 9/2004 |
| WO | WO-2004/101565 | 11/2004 |
| WO | WO-2005/005426 | 1/2005 |
| WO | WO-2005/028475 | 3/2005 |
| WO | WO-2005/028624 | 3/2005 |
| WO | WO-2005/030128 | 4/2005 |
| WO | WO-2005/030709 | 4/2005 |
| WO | WO-2005/034869 | 4/2005 |
| WO | WO-2005/044181 | 5/2005 |
| WO | WO-2005/058891 | 6/2005 |
| WO | WO-2005/062795 | 7/2005 |
| WO | WO-2005/063746 | 7/2005 |
| WO | WO-2005/063747 | 7/2005 |
| WO | WO-2005/066347 | 7/2005 |
| WO | WO-2005/082367 | 9/2005 |
| WO | WO-2005/085244 | 9/2005 |
| WO | WO-2005/086904 | 9/2005 |
| WO | WO-2005/092896 | 10/2005 |
| WO | WO-2005/095400 | 10/2005 |
| WO | WO-2005/103050 | 11/2005 |
| WO | WO-2005/115363 | 12/2005 |
| WO | WO-2005/115374 | 12/2005 |
| WO | WO-2005/116035 | 12/2005 |
| WO | WO-2005/123076 | 12/2005 |
| WO | WO-2006/004984 | 1/2006 |
| WO | WO-2006/009755 | 1/2006 |
| WO | WO-2006/009797 | 1/2006 |
| WO | WO-2006/010637 | 2/2006 |
| WO | WO-2006/015123 | 2/2006 |
| WO | WO-2006/015124 | 2/2006 |
| WO | WO-2006/063167 | 6/2006 |
| WO | WO-2006/114180 | 11/2006 |
| WO | WO-2006/114520 | 11/2006 |
| WO | WO-2006/127587 | 11/2006 |
| WO | WO-2006/137376 | 12/2006 |
| WO | WO-2007/002325 | 1/2007 |
| WO | WO-2007/002433 | 1/2007 |
| WO | WO-2007/009799 | 1/2007 |
| WO | WO-2007/013896 | 2/2007 |
| WO | WO-2007/022380 | 2/2007 |
| WO | WO-2007/106236 | 9/2007 |
| WO | WO-2008/058341 | 5/2008 |
| WO | WO-2008/065417 | 6/2008 |
| WO | WO-2008/063888 | 7/2008 |
| WO | WO-2008/079906 | 7/2008 |
| WO | WO-2008/079909 | 7/2008 |
| WO | WO-2008/064255 | 8/2008 |
| WO | WO-2008/076779 | 8/2008 |
| WO | WO-2008/064265 | 11/2008 |
| WO | WO-2008/138755 | 11/2008 |

(56) References Cited

FOREIGN PATENT DOCUMENTS

| WO | WO-2009/012283 | 1/2009 |
|---|---|---|
| WO | WO-2009/012791 | 1/2009 |
| WO | WO-2009/111277 | 9/2009 |
| WO | WO-2009/111278 | 9/2009 |
| WO | WO-2009/111279 | 9/2009 |
| WO | WO-2009/111280 | 9/2009 |
| WO | WO-2009/115084 | 9/2009 |
| WO | WO-2009/143024 | 11/2009 |
| WO | WO-2010/020905 | 2/2010 |
| WO | WO-2010/059658 | 5/2010 |
| WO | WO-2010/104945 | 9/2010 |
| WO | WO-2010/104973 | 9/2010 |
| WO | WO-2010/114928 | 10/2010 |
| WO | WO-2010/129567 | 11/2010 |
| WO | WO-2010/129570 | 11/2010 |
| WO | WO-2011/015522 | 2/2011 |
| WO | WO-2011/060216 | 5/2011 |
| WO | WO-2011/063159 | 5/2011 |
| WO | WO-2011/079133 | 6/2011 |
| WO | WO-2011/133637 | 10/2011 |
| WO | WO-2012/032236 | 3/2012 |
| WO | WO-2012/037060 | 5/2012 |
| WO | WO-2012/138809 | 10/2012 |
| WO | WO-2012/158957 | 11/2012 |
| WO | WO-2012/161776 | 11/2012 |

OTHER PUBLICATIONS

Amiel, et al., Hirschsprung disease, associated syndromes and genetics: a review, J Med Genet, (2008), 45:1-14.
Anderson, et al., Cooperative Catalyst Effects in Palladium-Mediated Cyanation Reactions of Aryl Halides and Triflates, J. Org. Chem. 63:8224-8228 (1998).
Antonini, et al., Synthesis of 4-Amino-1-β-D-Ribofuranosyl-1H-pyrrolo[2,3-b]pyridine (1-Deazatubercidin) as a Potential Antitumor Agent, J. Med. Chem. 25:1258-1261 (1982).
Arbiser, "Why targeted therapy hasn't worked in advanced cancer," The Journal of Clinical Investigation, (2007), 117(10):2762-2765.
Arthan, et al., "Leukemia inhibitory factor can mediate Ras/Raf/MEK/ERK-induced growth inhibitory signaling in medullary thyroid cancer cells," Cancer Letters (2010) 297:31-41.
Ashman, et al., The biology of stem cell factor and its receptor C-kit, The International Journal of Biochemistry & Cell Biology, 31:1037-1051, 1999.
Baghestanian, et al., A Case of Malignant Mastocytosis with Circulating Mast Cell Precursors: Biologic and Phenotypic Characterization of the Malignant Clone, Leuk. 10:159-166 (1996).
Bagshaw, et al, Measurement of Ligand Binding to Proteins Spectrophotometry and Spectrofluorimetry, 4:91-113, 1987.
Bagshawe, Antibody-Directed Enzyme Prodrug Therapy: A Review; 1995, Drug Dev. Res., 34:220-230.
Balak, et. al., Novel D761Y and common secondary T790M mutations in epidermal growth factor receptor-mutant lung adenocarcinomas with acquired resistance to kinase inhibitors. Clin. Cancer Res. 12:6494-501 (2006).
Bancalari, et al., Blood Markers of Early and Late Airway Responses to Allergen in Asthmatic Subjects. Relationship with Functional Findings Allergy 52:32-40, 1997.
Banker, et al, "Modern Pharmaceutics, 3ed.", Marcel Dekker, New York, 1996, p. 596.
Bartlett, et al., CAVEAT: A Program to Facilitate the Structure-Derived Design of Biologically Active Molecules Royal Society of Chemistry 78:I80-I96, 1989.
Barton, et al, The chemistry of pentavalent organobismuth reagants. Part X. Studies on the phenylation and oxidation of phenols, Tetrahedron, vol. 43, No. 2, 1987, pp. 323-332.
Bashford, et al., Measurement of Ligand Binding to Proteins, Spectrophotometry and Spectrofluorimetry: A Practical Approach 4:91-113 (1987).
Basta, et al, High-dose Intravenous Immunoglobulin Exerts Its Beneficial Effect in Patients with Dermatomyositis by Blocking Endomysial Deposition of Activated Complement Fragments; J Clin Invest 1994, 94:1729-1735.
Basto, et al., "Mutation analysis of B-RAF gene in human gliomas," Acta Neuropathol., (2005), 109:207-210.
Bayindir, et al., "Cellular mesoblastic nephroma (infantile renal fibrosarcoma): institutional review of clinical, diagnostic imaging, and pathological features of a distinctive neoplasm of infancy," Pediatr. Radiol., (2009), 39(10):1066-74.
Beaucage, et al., "Advances in Synthesis of Oligonucleotides by the Phosphoramidite Approach," Tetrahedron (1992), 48:2223-2311.
Bedi, et al., BCR-ABL-Mediated Inhibition of Apoptosis With Delay of G2/M Transition After DNA Damage: A Mechanism of Resistance to Multiple Anticancer Agents; Blood 1995, 86:1148-1158.
Bell, (1981) Spectroscopy in Biochemistry, vol. I, pp. 155-194, CRC Press.
Bellone, et al., Growth Stimulation of Colorectal Carcinoma Cells Via the c-Kit Receptor is Inhibited by TGF-β1, J. Cell Physiol. 172:1-11 (1997).
Berdel, et al., Recombinant Human Stem Cell Factor Stimulates Growth of a Human Glioblastoma Cell Line Expressing c-kit Protooncogene, Canc. Res. 52:3498-3502 (1992).
Bertolini, et al., A new Rational Hypothesis for the Pharmacophore of the Active Metabolite of Leflunomide, a Potent Immunosuppressive Drug; 1997, J. Med. Chem., 40:2011-2016.
Bjorntorp, Neuroendocrine Pertuirbations as a Cause of Insulin Resistance; Diabetes Metab. Res. Rev., 1999, 15: 427-441.
Bloom, et al., The Preparation of 2-Alkylaminobenzimidazoles, J. Org. Chem. 14, 17 (1939).
Blundell, et al., Knowledge-Based Protein Modelling and Design Eur. J. Biochem. 172:513-520 1988.
Bode, et al, Modern Pathology, (2006), 19:541-547.
Böhm, On the Use of LUDI to Search the Fine Chemicals Directory for Ligands of Proteins of Known Three-Dimensional Structure, J. Comp. Aided Molec. Design 8:623-632, 1994.
Bokenmeyer, et al., Expression of Stem-Cell Factor and Its Receptor c-kit Protein in Normal Testicular Tissue and Malignant Germ-Cell Tumours, J. Cancer Res. Clin. Oncol. 122:301-306 (1996).
Bolger, et al, Computer Modeling of Combining Site Structure of Anti-Hapten Monoclonal Antibodies, Methods Enz., 203:21-45, 1991.
Bollag, et al., "Vemurafenib: the first drug approved for BRAF-mutant cancer," Nature Reviews Drug Discovery, (2012), 11(11):873-886.
Bongarzone, et al., High Frequency of Activation of Tyrosine Kinase Oncogenes in Human Papillary Thyroid Carcinoma, Oncogene 4(12):1457-1462 (1989).
Bothwell, Keeping Track of Neurotrophin Receptors Cell, 65:915-918, 1991.
Bouzakri, et al., MAP4K4 Gene silencing in Human Skeletal Muscle Prevents Tumor Necrosis Factor-a-induced Insulin Resistance, J. Biol. Chem. 282:7783-7789 (2007).
Bouzas-Rodriguez, et al., Neurotrophin-3 production promotes human neuroblastoma cell survival by inhibiting TrkC-induced apoptosis, J. Clin. Invest., (2010), 120(3):850-858.
Bowtell, Options Available From Start to Finish for Obtaining Expression Data by Microarray, Nature Genetics Supp. 21:25-32 (1999).
Breindl, "No Melanocyte is an Island: In Melanoma, Interfeon, Roles Need Rethinking," BioWorld Today, (2011), 22(17):1:5.
Brenner, et al., Encoded Combinatorial Chemistry, Proc. Natl. Acad. Sci. USA 89:5381-5383, 1992.
Broudy, Stem Cell Factor and Hematopoiesis, Blood 90:1345-1364 (1997).
Brünger, Free R Value: a Novel Statistical Quantity for Assessing the Accuracy of Crystal Structures Nature 355:472-475 (1992).
Buchschacher, Human Immunodeficiency Virus Vectors for Inducible Expression of Foreign Genes; (1992) J. Virol. 66:2731-2739.
Bundgaard, "Design of produdrugs: Bioreversible derivatives for various functional groups and chemical entitites," Design of Produgs, , (1985), p. 1.
Burns, et al., c-FMS Inhibitars: A Patent Review, Expert Opinion Ther. Patents (2011), 21(2):147-165.
Caira, "Crystalline polymorphism of organic compounds," Topics in Current Chemistry, (1998), 198:163-208.

(56) References Cited

OTHER PUBLICATIONS

Calabresi, et al., "Section IX: Chemotherapy of neoplastic diseases," Goodman & Gilman's The Pharmacological Basis of Therapeutics, Tenth Edition, McGraw-Hill Medical Publishing Division (2001), pp. 1381, 1383-1385 and 1388.
Capon, et al., Designing CD4 Immunoadhesins for AIDS Therapy, Nature 337:525-531 (1989).
Carell, et al., New Promise in Combinatorial Chemistry: Synthesis, Characterization, and Screening of Small-Molecule Libraries in Solution, Chem. Biol. 2:171-183 (1995).
Carpino, et al., p62dok: A Constitutively Tyrosine-Phosphorylated, GAP-Associated Protein in Chronic Myelogenous Leukemia Progenitor Cells; Cell 1997, 88:197-204.
Castellone, et al., A novel de novo germ-line V292M mutation in the extracellular region of RET in a patient with phaeochromocytoma and medullary thyroid carcinoma: functional characterization, Clinical Endocrinology, (2010), 73:529-534.
Castells, et al., The Presence of Membrane-Bound Stem Cell Factor on Highly Immature Nonmetachromatic Mast Cells in the Peripheral Blood of a Patient with Aggressive Systemic Mastocytosis, J. Aller. Clin. Immunol. 98:831-840 (1996).
Castro, et al. "Utilizacion de dispersiones solidas como estrategia para aumentar la velocidad de disolucion de farmacos", Nuestra Farmcia, 25:24-29 (2008) (No English Translation Available).
Chabala, Solid-Phase Combinatorial Chemistry and Novel Tagging Methods for Identifying Leads, Curr Opin Biotechnol 6:632-639 (1995).
Chappell, et al., "Ras/Raf/MEK/ERK and PI3K/PTEN/Akt/mTOR Inhibitors: Rationale and Importance to Inhibiting These Pathways in Human Health," Oncotarget, (2011), 2(3):135-164.
Chayer, et al., Synthesis of Carboranylpyrroles, Tetrahedron Lett. 42(44):7759-7761 (2001).
Checovich, et al., Fluorescence Polarization—A New Tool for Cell and Molecular Biology, Nature 375:254-256 (1995).
Chou, et al., Chemotherapeutic Synergism, Potentiation and Antagonism, Encyclopedia of Human Biology, Academic Press, 2:371-9 (1991).
Chou, et al., Computerized Quantitation of Synergism and Antagonism of Taxol, Topotecan, and Cisplatin Against Human Teratocarcinoma Cell Growth: a Rational Approach to Clinical Protocol Design, J. Natl. Cancer Inst. 86:1517-24 (1994).
Chou, Quantitative analysis of Dose-Effect Relationships: The Combined Effects of Multiple Drugs or Enzyme Inhibitors, Adv. Enzyme Regul. 22:27-55 (1984).
Chou, Synergism and Antagonism in Chemotherapy, San Diego, CA: Academic Press, Chapter 2, 61-102 (1991).
Clark, et al., PRO_LIGAND: An Approach to De Novo Molecular Design. 1. Application to the Design of Organic Molecules, J. Comp. Aided Molec. Design 9:13-32 (1995).
Clohisy, et al, Review of Cellular Mechanisms of Tumor Osteolysis; Clin. Orthop. 2000, 373: 104-14.
Coe, et al., Solution-Phase Combinatorial Chemistry, Mol Divers. 4:31-38 (1999).
Coelho, et al., Studies of RET gene expression and acetylcholinesterase activity in a series of sporadic Hirschsprung's disease, Pediatr Surg Int, (2008), 24:1017-21.
Cohen, et al., Expression of Stem Cell Factor and C-Kit in Human Neuroblastoma; 1994, Blood 84:3465-3472.
Collins, et al., A small interfereing RNA screen for modulators of tumor cell motility identifies MAP4K4 as a prommigratory kinase, Proc. Natl. Acad. Sci. USA, 103:3775-3780 (2006).
Collioud, et al., Oriented and Covalent Immobilization of Target Molecules to Solid Supports: Synthesis and Application of a Light-Activatable and Thiol-Reactive Cross-Linking Reagent; (1993) Bioconjugate Chem. 4:528-536.
Colman, Structure-Based Drug Design, Current Opinion in Struc. Biol. 4: 868-874 (1994).
Columbo, et al., The Human Recombinant c-kit Receptor Ligand, rhSCF, Induces Mediator Release From Human Cutaneous Mast Cells and Enhances IgE-Dependent Mediator Release From Both Skin Mast Cells and Peripheral Blood Basophils, J. Immunol 149:599-608 (1992).
Communication Pursuant to Article 94(3). EPC for European Application No. 04814626.0 dated Jun. 6, 2011.
Communication Pursuant to Article 94(3). EPC for European Application No. 05789913.0 dated Feb. 15, 2010.
Communication Pursuant to Article 94(3). EPC for European Application No. 06773861.7 dated Apr. 22, 2010.
Communication Pursuant to Article 94(3). EPC for European Application No. 06773861.7 dated Jul. 9, 2009.
Communication Pursuant to Article 94(3). EPC for European Application No. 06773861.7 dated Dec. 21, 2009.
Communication Pursuant to Article 94(3). EPC for European Application No. 06813186.1 dated Sep. 15, 2009.
Communication Pursuant to Article 94(3). EPC for European Application No. 07864681.7 dated Dec. 2, 2009.
Communication Pursuant to Article 94(3). EPC for European Application No. 10722860.3 dated Mar. 27, 2013.
Communication Pursuant to Article 94(3). EPC for European Appln. No. 11173701.1 dated Jan. 4, 2013.
Communication Pursuant to Article 94(3). EPC for European Appln. No. 07864681.7 dated Oct. 8, 2012.
Coniglio, et al., "Microglial stimulation of glioblastoma invasion involves epidermal growth factor receptor (EGFR) and colony stimulating factor 1 receptor (CSF-1R) signaling," Mol. Med., (2012), 18:519-527.
Costa, et al., The Cells of the Allergic Response, JAMA 278:1815-1822 (1997).
Coste, et al., Coupling N-Methylated Amino Acids Using PyBroP1 and PyCloP Halogenophosphonium Salts: Mechanism and Fields of Application, Journal of Organic Chemistry 59:2437-2446 (1994).
Coulie, et al, Recombinant Human Neurotropic Factors Accelerate Colonic Transit and Relieve Constipation in Humans, Gastroenterology 119:41-50 (2000).
Creighton, An Empirical Approach to Protein Conformation Stability and Flexibility, Biopolymers 22(1):49-58 (1983).
Crouch, et al., The use of ATP bioluminescence as a measure of cell proliferation and cytotoxicity. Journal of Immunological Methods, 160:81-8 (1993).
Crump,Inhibition of Raf Kinase in the Treatment of Acute Myeloid Leukemia, Curr. Pharm. Design 8(25):2243-8 (2002).
Curtin, et al., Discovery and Evaluation of a Series of 3-Acylindole Imidazopyridine Platelet-Activating Factor Antagonists, J. Med. Chem., vol. 41, 1998, pp. 74-95.
Curtin, et al., "Somatic activation of KIT in distinct subtypes of melanoma," J. of Clinical Oncology, (2006), 24(26):4340-4345.
Cwirla, et al., Peptides on Phage: A Vast Library of Peptides for Identifying Ligands, Biochemistry 87:6378-6382 (1990).
Dai, et al., Targeted disruption of the mouse colony-stimulating factor 1 receptor gene results in osteopetrosis, mononuclear phagocyte deficiency, increased primitive progenitor cell frequencies, and reproductive defects; Blood, 2002, 99: 111-120.
Damasio, "Alzheimer's Disease and Related Dementias," Cecil Textbook of Medicine, 20th Edition, (1996), 2:1992-1996.
Dandliker, et al., Equilibrium and Kinetic Inhibition Assays Based Upon Fluorescence Polarization, Methods in Enzymology 74:3-28 (1981).
Das-Gupta et al., "Acridine Derivatives, Part VI," J. Indian Chem. Society, (1941), 18:25-28.
Dastych, et al., Stem Cell Factor Induces Mast Cell Adhesion to Fibronectin; 1994, J. Immunol. 152:213-219.
Davies, et al., "Mutations of the BRAF gene in human cancer," Nature, (2002), 417:949-954.
Demetri, Targeting c-kit mutations in solid tumors: Scientific rationale and novel therapeutic options, Seminars in Oncology, 28(5), Supp. 17, 19-26, 2001.
Denardo, et al., "Leukocyte complexity predicts breast cancer survival and functionally regulates response to chemotherapy," Cancer Discovery, (2011), 54-67.
Dewar, et al., Inhibition of c-fms by Imatinib Expanding the Spectrum of Treatment; Cell Cycle 4(7):851-3 (2005).

(56) References Cited

OTHER PUBLICATIONS

Dobeli, et al., Recombinant Fusion Proteins for the Industrial Production of Disulfide Bridge containing Peptides: Purification, Oxidation without Cancatamer Formation, and Selective Cleavage; (1998) Protein Expr. Purif. 12:404-414.
Dolle, et al., Comprehensive Survey of Combinatorial Library Synthesis: 1998, J Comb Chem 1:235-282 (1999).
Dong, et al., "BRAF Oncogenic Mutations Correlate with Progression rather than Initiation of Human Melanoma," Cancer Research, (2003), 63:3883-3885.
Donis-Keller, et al., Mutations in the RET Proto-Oncogene are Associated with MEN 2A and FMTC, Hum Mol Genet. 2(7):851-856 (1993).
Dorwald, Side Reactions in Organic Synthesis: A Guide to Successful Synthesis Design. Wiley-VCH, Preface (2005), p. IX.
Douma, et al, Suppression of anoikis and induction of metastasis by the neurotropic receptor TrkB, Nature 430:1034-9 (2004).
Doyle, Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media; J. Org. Chem. 44:1572, (1979).
Dube, Reductive N-Alkylation of Amides, Carbamates and Ureas, Tetrahedron Lett. 40:2295-2298 (1999).
Dumas, Protein kinase inhibitors: emerging pharmacophores 1997-2000. Exp. Opin. Ther. Patents, (2001), 11(3):405-429.
Durbec, et al., GDNF Signalling Through the Ret Receptor Tyrosine Kinase, Nature 381:789-793 (1996).
Dutcher et al., "Studies of the C11H8N2OS Degradation Product of Gliotoxin," J. Am. Chem. Soc., (1951), 73:4139-4141.
Dyson, et al., The Human Papilloma Virus 13 16 E7 Oncoprotein is Able to Bind to the Retinoblastoma Gene Product, Science 243:934-937 (1989).
Eklund, Treatment of rheumatoid arthritis with imatinib mesylate: clinical improvements in three refractory cases, Annals of Medicine, 35:362-367, 2003.
Eliseev, et al, Dynamic Combinatorial Chemistry: Evolutionary Formation and Screening of Molecular Libraries, Current Topics in Microbiology & Immunology 243:159-172 (1999).
Engelman, et al., "Effective use of P13K and MEK inhibitors to treat mutant Kras G12D and PIK3CA H1047R murine lung cancers," Nature Medicine, (2008), 14(12):1351-1356.
Enjalbal, et al., Mass Spectrometry in Combinatorial Chemistry, Mass Spectrometry Reviews. 19:139-161 (2000).
Ertl, et al., "Fast calculation of molecular polar surface area as a sum of fragment-based contributions i I and its application to the prediction of drug transport properties," J Med Chem, (2000), 43:3714-3717.
Escribano, et al., Expression of the c-kit (CD117) Molecule in Normal and Malignant Hematopoiesis, Leuk. Lymph. 30:459-466 (1998).
European Communication pursuant to Article 94(3) EPC dated Oct. 8, 2012 in related European Patent Application No. 07 864 681.7.
Exam Report in Australian Application No. 2012200933 dated Jul. 3, 2013.
Exam Report in Egyptian Application No. 1439/2007 dated Nov. 3, 2014.
Examination Report dated Mar. 14, 2012 in related New Zealand Patent Application No. 577011.
Examination Report for GCC Patent Application No. GCC/P/2005/4795 dated Jun. 27, 2008.
Examination Report for Guatemala Patent Application No. PI-2005-00164 dated Jul. 2, 2008.
Examination Report for Pakistan Patent Application No. 0679/2006.
Examination Report in New Zealand Application No. 599866 dated Aug. 22, 2014.
Examination Report in New Zealand Application No. 613786 dated May 5, 2014.
Examiner's Report dated Mar. 13, 2012 in related Australian Patent Application No. 2007323644.
Examiners Report for New Zealand Application No. 629615 dated Sep. 1, 2014.
Examiners Report in Australian Application No. 2010232670 dated Jun. 6, 2014.
Examiners Report in New Zealand Application No. 599866 dated Feb. 14, 2013.
Extended European Search Report dated Mar. 6, 2012 in related EP Application No. 1117370.1.
Extended European Search Report for EP Application 100840075.5 dated May 13, 2013.
Extended European Search Report for EP Application 10832209.0 dated Apr. 17, 2013.
Extended Search Report in European Application No. 10829123.8 dated May 31, 2013.
Felder, The Challenge of Preparing and Testing Combinatorial Compound Libraries in the Fast Lane, at the Front End of Drug Development, Chimia 48:531-541 (1994).
Feng, et al, Tyrosines 559 and 807 in the Cytoplasmic Tail of the Macrophage colony-Stimulating Factor Receptor Play Distinct Roles in Osteoclast Differentiation and Function; Endocrinology 2002, 143: 4868-74.
Feng, et al., Stable in Vivo Gene Transduction via a Novel Adenoviral/Retroviral Chimeric Vector, Nature Biotechnology 15:866-870 (1997).
Finotto, et al., Glucocorticoids Disease Tissue Mast Cell Number by Reducing the Production of the c-kit Ligand, Stem Cell Factor, by Resident Cells, J. Clin. Invest. 99:1721-1728 (1997).
Fischer, et al., "Targeting receptor tyrosine kinase signalling in small cell lung cancer (SCLC): What have we learned so far?," Cancert Treatment Reviews, (2007), 33:391-406.
Fivash, et al., BIAcore for macromolecular interaction; (1998) BIAcore for macromolecular interaction, Current Opinion in Biotechnology. 9:97-101.
Flaherty, "Inhibition of mutated, activated BRAF in metastatic melanoma," New England Journal of Medicine, (2010), 363(9):809-819.
Flanagan, et al., "Update on the biologic effects of macrophage colony-stimulating factor," Curr Opin Hematol., (1998), 5:181-185.
Flanagan, Macrophages and the various isoforms of macrophage colony-stimulating factor; Curr Opin Hematol. 1998, 5:181-5.
Franz, Sulfuranes. X. A Reagent for the Facile Cleavage of Secondary Amides, JACS, 95(6):2017-2019 (1973).
Friesen, et al., "Hydroxypropyl Methylcellulose Acetate Succinate-Based Spray-Dried Dispersions: An Overview," Molecular Pharmaceutics, 5(6):1003-1019 (2008).
Furitsu, et al., Identification of Mutations in the Coding Sequence of the Proto-oncogene c-kit in a Human Mast Cell Leukemia Cell Line Causing Ligand-independent Activation of the c-kit Product; 1993, J. Clin. Invest. 92:1736-1744.
Furuta, et al., Stem Cell Factor Influences Mast Cell Mediator Release in Response to Eosinophil-Derived Granule Major Basic Protein, Blood 92:1055-1061 (1998).
Gallego, et al., "Increased opioid dependence in a mouse model of panic disorder," Front Behav. Neurosci., (2010), 3:60.
Gallop, et al., Applications of Combinatorial Technologies to Drug Discovery. 1. Background and Peptide Combinatorial Libraries, J. Med. Chem. 37:1233-1251 (1994).
Galofre, et al., Evaluation and Treatment of Thyroid Nodules: A Clinical Guide, (2008), Mt Sinai J Med, 75:299-311.
Garzya, et al., "Indium(III)-catalysed aryl sulfonylation reactions," Tetrahedron Letters, (2004), 45:1499-1501.
Gassman, et al., Specific Ortho Substitution of Aromatic Heterocyclic Amines, J American Chemical Society, (1973), 95(13), pp. 4453-4455.
Ghebre-Sellassie, "Pharmaceuticast Extrusion Technology," Marcer Dekker, Inc., New York. Basel. CRC Press, (2003), p. 238.
Gimbel, et al., "Braf mutations are associated with increased mortality in colorectal cancer," Journal of the American College of Surgeons, (2004), 199:S91-S92.
Girgis, et.al., The Synthesis of 5-Azaindoles by Substitution-Rearrangement of 7-Azaindoles upon Treatment with Certain Primary Amines; J. Heterocyclic. Chem. 1989, 26:317-325.

(56) References Cited

OTHER PUBLICATIONS

Golkar, et al., Mastocytosis, Lancet 349:1379-1385 (1997).
Golub, et al., Molecular Classifcation of Cancer: Class Discovery and Class Prediction by Gene Expression Monitoring, Science, 286:531-537 (1999).
Goodford, A Computational Procedure for Determining Energetically Favorable Binding Sites on Biologically Important Macromolecules, J. Med. Chem. 28:849-857 (1985).
Goodsell, et al, Automated Docking of Substrates to Proteins by Simulated Annealing, Proteins: Structure, Function, and Genetics 8:195-202 (1990).
Gordon, Detection of Peroxides and Their Removal, The Chemist's Companion: A Handbook of Practical Data, Techniques, and References p. 437 (1972).
Gordon, et al., Applications of Combinatorial Technologies to Drug Discovery. 2. Combinatorial Organic Synthesis, Library Screening Strategies, and Future Directions, J. Med. Chem. 37:1384-1401 (1994).
Gram, Phage Display in Proteolysis and Signal Transduction, Combinatorial Chemistry & High Throughput Screening 2:19-28 (1999).
Gravert, et al, Synthesis on Soluble Polymers: New Reactions and the Construction of Small Molecules, Curr Opin Chem Biol 1:107-113 (1997).
Greer, Model Structure for the Inflammatory Protein C5a, Science 228:1055-1060 (1985).
Grieco, et al., PTC is a Novel Rearranged Form of the ret Proto-Oncogene and is Frequently Detected in Vivo in Human Thyroid Papillary Carcinomas, Cell 60(4):557-563 (1990).
Guida, Software for Structure-Based Drug Design, Current Opinion in Struc. Biol. 4:777-781 (1994).
Gura, "Systems for identifying New Drugs Are Often Faulty, Cancer Models," Science, (1997), 278(5340):1041-1042.
Hafner, et al., Isothermal Amplification and Multimerization of DNA by Bst DNA Polymerase, Biotechniques Apr;30(4):852-867 (2001).
Hallek, et al., Interaction of the Receptor Tyrosine Kinase p145c-kit with the p210bcr/abl Kinase in Myeloid Cells, Brit. J Haem. 94:5-16 (1996).
Halvorson, et al., A Blocking Antibody to Nerve Growth Factor Attenuates Skeletal Pain Induced by Prostate Tumor Cells Growing in Bone, Cancer Res. 65:9426-35 (2005).
Hamel, et al., The Road Less Traveled: c-kit and Stem Cell Factor, J. Neuro-Onc. 35:327-333 (1997).
Hancock, et al., "Characteristics and Significance of the Amorphous State in Pharmaceutical Systems," Journal of Pharmaceutical Sciences 86(1):1-12 (1997).
Hands, et. al., A convenient Method for the Preparation of 5-, 6- and 7-Azaindoles and Their Derivatives; Synthesis, 877-882 (1996).
Hanselman, et al., A cDNA-Dependent Scintillation Proximity Assay for Quantifying Apolipoprotein A-1, J. Lipid Res. 38:2365-2373 (1997).
Hasegawa, et al., "Visualizing Mechanosensory Endings ofTrkC-Expressing Neurons in HS3ST-2-hPLAP Mice," J Comp. Neurol., (2008), 511(4):543-556.
Hassan, et al., Expression of Protooncogene c-kit and Its Ligand Stem Cell Factor (SCF) in Gastric Carcinoma Cell Lines; 1998, Digest. Dis. Science 43:8-14.
Hassan, Stem Cell Factor as a Survival and Growth Factor in Human Normal and Malignant Hematopoiesis, Acta. Hem. 95:257-262 (1996).
Hayashi, et al., Dichloro[1,1 19-bis(diphenylophosphino)ferrocene]palladium-(II), An Effective Catalyst for Cross-Coupling of Secondary and Primary Alkyl Grignard and Alkylzinc Reagents with Organic Halides, J. Am. Chem. Soc. 106:158-163 (1984).
Haydock, et al., Analogues of clofibrate and clobuzarit containing fluorine in the side chains, European Journal of Medicinal Chemistry, 19:205-214 (1984).
He et al. "c-Fms Signaling Mediates Neurofibromatosis Type-1 Osteoclast Gain-In-Functions," PLoS ONE, (2012), 7(11):1-9.

He, et al., "Gamma-secretase activating protein, a therapeutic target for Alzheimer's disease," Nature, (2010), 467(7311):95-98.
Heacock et al., Orientation and Relative Reaction rate Factors in aromatic Substitution by the Benzensulfonimido Radical, J. Am. Chem. Soc., vol. 82, 1960, pp. 3460-3463.
Heim, et al., Engineering Green Fluorescent Protein for Improved Brightness, Longer Wavelengths and Fluorescence Resonance Energy Transfer, Curr. Biol. 6:178-182 (1996).
Heinrich, et al., "Inhibition of Kit Tyrosine Kinase Activity: A Novel Molecular Approach to the Treatment of KIT-Positive Malignancies," J. Clin. Oncol., vol. 20, No. 6, pp. 1692-1703, Mar. 15, 2002.
Heinrich, et al., PDGFRA Activating Mutations in Gastrointestinal Stromal Tumors; (Science 2003, 299:708-10).
Hentschel, et al., "BCR-ABL-and Ras-independent activiation of Raf as a novel mechanism of Imatinib resistance in CML," (2012), http://www.ncbi.nlm.nih.gov/pubmed/2163917.
Herbst, et al., Differential Effects of W Mutations on p145c-kit Tyrosine Kinase Activity and Substrate Interaction, J. Biol. Chem. 267:13210-13216 (1992).
Hibi, et al., Coexpression of the stem cell factor and the c-kit genes in small-cell lung cancer; 1991, Oncogene 6:2291-2296.
Hirota, et al., Gain-of-function Mutations of c-kit in Human Gastrointestinal Stromal Tumors; 1998, Science 279:577-580.
Hoffmann, m-Trifluoromethylbenzenesulfonyl Chloride, Organic Syntheses , Coll. vol. 60, p. 121-126, 1981.
Hogaboam, et al., Novel Role of Transmembrane SCF for Mast Cell Activation and Eotaxin Production in Mast Cell-Fibroblast Interactions, J. Immunol. 160:6166-6171 (1998).
Holmes, et al., "Long-term effects of Aβ42 immunisation in Alzheimer's disease: follow-up of a randomised, placebo-controlled phase I trail," The Lancet, (2008), 372:216-233.
Hood, J.D. et al., Tumor Regression by Targeted Gene Delivery to the Neovasculature, Science 296, 2404 (2002).
Houghten, et al., Generation and Use of Synthetic Peptide Combinatorial Libraries for Basic Research and Drug Discovery, Nature 354:84-86 (1991).
Houghten, Parallel Array and Mixture-Based Synthetic Combinatorial Chemistry: Tools for the Next Millennium, Annu Rev Pharmacol Toxicol 40:273-282 (2000).
Houghten, Peptide Libraries: Criteria and Trends, Trends Genet. 9:235-239 (1993).
Hudson, et al., A Simple Method for the Determination of Serum Acid Phosphatase, Journal of Urology 58:89-92 (1947).
Hughes-Jones, et al., Synthesis of Rh Fv Phage-Antibodies Using VH and VL Germline Genes, British Journal of Haematology 105:811-816 (1999).
Ibrahim, et al., "Pyrrolo[2,3-b]pyridine derivatives as protein kinase inhibitors and their preparation, pharmaceutical compositions and use in the treatment of diseases," Caplus , (2007), 11300.
Iemura, et al., The c-kit Ligand, Stem Cell Factor, Promotes Mast Cell Survival by Suppressing Apoptosis, Amer. J. Pathol 144:321-328 (1994).
Inoue, et al., Coexpression of the c-kit Receptor and the Stem Cell Factor in Gynecological Tumors, Cancer Res. 54:3049-3053 (1994).
International Preliminary Report on Patentability dated Sep. 23, 2014 for PCT Application No. PCT/US2013/032835.
International Preliminary Report on Patentability dated Nov. 9, 2011 in PCT Application No. PCT/US2010/033576.
International Search Report and Written Opinion dated Jan. 14, 2011 for PCT Patent Application No. PCT/US2010/055519.
International Search Report and Written Opinion dated Jan. 25, 2011 for PCT Patent Application No. PCT/US2010/057293.
International Search Report and Written Opinion dated Feb. 18, 2010 for PCT Patent Application No. PCT/US2009/044151.
International Search Report and Written Opinion dated Mar. 31, 2012 for PCT Patent Application No. PCT/US2012/025965.
International Search Report and Written Opinion dated May 7, 2013 for PCT Patent Application No. PCT/US2013/032835.
International Search Report and Written Opinion dated May 31, 2012 for PCT Patent Application No. PCT/US2012/023543.
International Search Report and Written Opinion dated Jun. 11, 2010 for PCT Patent Application No. US2010/026856.

(56) References Cited

OTHER PUBLICATIONS

International Search Report and Written Opinion dated Jun. 30, 2010 for PCT Application No. PCT/US2010/033576.
International Search Report and Written Opinion dated Jul. 22, 2013 for PCT Patent Application No. PCT/US2013/043400.
International Search Report and Written Opinion dated Sep. 22, 2009 for PCT Patent Application No. PCT/US2009/046598.
International Search Report and Written Opinion dated Sep. 23, 2011 for PCT Patent Application No. PCT/US2010/061601.
International Search Report and Written Opinion dated Oct. 24, 2006 for PCT Patent Application No. PCT/US2006/024524.
International Search Report and Written Opinion dated Jun. 11, 2010 for PCT Patent Application No. PCT/US2010/026816.
International Search Report and Written Opinion of the ISA dated Oct. 24, 2006 for PCT Application No. PCT/US2006/024524.
International Search Report and Written Opinion of the ISA dated Apr. 4, 2007 for PCT Application No. PCT/US2006/018726.
International Search Report and Written Opinion of the ISA dated Apr. 20, 2006 for PCT Application No. PCT/US2005/021231.
International Search Report and Written Opinion of the ISA dated Jun. 4, 2008 for PCT Application No. PCT/US2007/088231.
International Search Report and Written Opinion of the ISA dated Jun. 4, 2008 for PCT Application No. PCT/US2007/088237.
International Search Report and Written Opinion of the ISA dated Jun. 5, 2008 for PCT Application No. PCT/US2007/083910.
International Search Report and Written Opinion of the ISA dated Jun. 5, 2008 for PCT Application No. PCT/US2007/085289.
International Search Report and Written Opinion of the ISA dated Jun. 5, 2008 for PCT Application No. PCT/US2007/088243.
International Search Report and Written Opinion of the ISA dated Jul. 25, 2008 for PCT Application No. PCT/US2007/088443.
International Search Report and Written Opinion of the ISA dated Jul. 28, 2008 for PCT Application No. PCT/US2007/085299.
International Search Report and Written Opinion of the ISA dated Oct. 24, 2006 for PCT Application No. PCT/US2006/024361.
International Search Report and Written Opinion of the ISA dated Nov. 17, 2008 for PCT Application No. PCT/US07/088412.
International Search Report and Written Opinion of the ISA dated Nov. 25, 2005 for PCT Application No. PCT/US04/42470.
International Search Report and Written Opinion of the ISA dated Oct. 5, 2010 for PCT Application No. PCT/US2010/029489.
International Search Report dated Sep. 13, 2010 in PCT Application No. PCT/US2010/033571.
International Search Report dated Dec. 19, 2011 in PCT Application No. PCT/US2011/033192.
International Search Report for PCT/US2012/038417 dated Aug. 10, 2012.
Isbel, et al., Local macrophage proliferation correlates with increased renal M-CSF expression in human glomerulonephritis; Nephrol Dial Transplant 2001, 16: 1638-1647.
Ishizaka, et al., Human ret Proto-Oncogene Mapped to Chromsome 10q11.2, Oncogene 4(12):1519-1521 (1989).
Isozaki, et al., Deficiency of c-kit cells in patients with a myopathic form of chronic idiopathic intestinal pseudo-obstruction; 1997, Amer. J. of Gast. 9 332-334.
Ivanisevic et al., "Uses of X-Ray Powder Diffraction in the Pharmaceutical Industry," Pharm Sci Encyc 1-42 (2010).
Iwane, et al., Myosin Subfragment-1 is Fully Equipped with Factors Essential for Motor Function, Biochem. and Biophys. Res. Comm. 230:76-80 (1997).
Izquierdo, et al., Differential Expression of the c-kit Proto-Oncogene in Germ Cel Tumours, J. Pathol. 177:253-258 (1995).
Jaiswal, et al., Combined Targeting of BRAF and CRAF or BRAF and P13K Effector Pathways is Requred for Efficacy in NRAS Mutant Tumors, PLoS One, (2009), 4(5):e5717.
Jarugula, et al., "Nonlinear Pharmacokinetics of 5-Fluorouracil in Rats," J Pharm Sci., (1997), 86(6):756-757.
Jensen, et al, Brit J Pharmacology, (2008), 154:1572-1582.
Jing, et al., GDNF-Induced Activation of the Ret Protein Tyrosine Kinase is Mediated by GDNFR-a, a Novel Receptor for GDNF, Cell 85:1113-1124 (1996).
Johann, et al., GLVR1, a Receptor for gibbon Ape Leukemia Virus, is Homologous to a Phosphate Permease of Neurospora crassa and is Expressed at High Levels in the Brain and Thymus; (1992) J. Virol. 66:1635-1640.
Johnson, et al., Relationships between drug activity in NCI preclinical in vitro and in vivo models and early clinical trials, British Journal of Cancer (2001), 64(10):1424-1431.
Johnston, Gene Chips: Array of hope for understanding gene regulation; (1998) Curr. Biol. 8:R171-R174.
Jones, Biology and Treatment of Chronic Myeloid Leukemia, Curr. Opin. Onc. 9:3-7 (1997).
Jones, et al., Antiestrogens. 2. Structure-Activity Studies in a Series of 3-Aroyl-2-arylbenzo[b]thiophene Derivatives Leading to [6-Hydroxy-2-(4-hydroxyphenyl)benzo(b)thien-3-yl](4-[2-(1-piperidinyl)ethoxy]-phenyl]methanone Hydrochloride (LY156758), a Remarkably Effective Estrogen Antagonist with Only Minimal Intrinsic Estrogenicity, J.Med.Chem., 27:1057-1066 (1984).
Jones, Interactive Computer Graphics: FRODO, Methods in Enzymology 115:157-171 (1985).
Jongh, et al. "The Role of Interleukin-6 in Nociception and Pain," Anesth. Analg., (2003), 96:1096-103.
Jose, et al., Blockade or Macrophage colony-Stimulating Factor Reduces Macrophage Proliferation and Accumulation in Renal Allograft Rejection; Am J Transplant 2003, 3(3):294-300.
Joseph-McCarthy, Computational Approaches to Structure-Based Ligand Design, Pharmacology & Therapeutics 84:179-191 (1999).
Joule, et al., "Indole and its Derivatives," Science of Synthesis (2001), 10:618-652.
Kahl, et al., A Multiple-Approach Scintillation Proximity Assay to Measure the Association Between Ras and Raf, Anal. Biochem. 243:282-283 (1996).
Kassel, et al., Local increase in the number of mast cells and expression of nerve growth factor in the bronchus of asthmatic patients after repeated inhalation of allergen at low-dose, Clin. Exp. Allergy 31:1432-40 (2001).
Katritzky, et al., Regiospecific C-Acylation of Pyrroles and Indoles Using N-Acylbenzotriazoles, J. Org. Chem. 68:5720-5723 (2003).
Kay, et al., Eosinophils and Eosinophil-Associated Cytokines in Allergic Inflammation, Int. Arch. Aller. Immunol. 113:196-199 (1997).
Kern, Direct Hybridization of Large-Insert Genomic Clones on High-Density Gridded cDNA Filter Arrays, Biotechniques 23:120-124 (1997).
Khazak, et al., "Selective Raf Inhibition in Cancer Therapy," (2012), http://www.ncbu.nlm.nih.gov/pms/articles/PMC2720036.
Kim, et al, A Merger of Rational Drug Design and Combinatorial Chemistry: Development and Application of Peptide Secondary Structure Mimetics, Combinatorial Chemistry & High Throughput Screening 3:167-183 (2000).
Kim, et al, Database CAS on STN (Columbus, OH, USA) No. 138:55974, Preparation of 2-anilino-4-indolyl pyrimidines as tyrosine kinase inhibitors, abstract, 2002) see whole article.
Kinashi, Steel Factor and c-kit Cell-Matrix Adhesion; Blood 83:1033-1038 (1994).
Kirkpatrick, et al., Structure-Based Drug Design: Combinatorial Chemistry and Molecular Modeling, Combinatorial Chemistry & High Throughput Screening 2:211-221 (1999).
Kitamura, et al., Synthesis of Quinolines and 2H-Dihydropyrroles by Nucleophilic Substitution at the Nitrogen Atom of Oxime Derivatives, Synthesis 15:2415-2426 (2003).
Kline, et al., Studies by 1H Nuclear Magnetic Resonance and Distance Geometry of the Solution Conformation of the x-Amylase Inhibitor Tendamistat, J. Mol. Biol. 189:377-382 (1986).
Knighton, et al., Structural Basis of the Intrasteric Regulation of Myosin Light Chain Kinases, Science 258:130-135 (1992).
Kodama, et al, Congenital Osteoclast Deficiency in Osteopetrotic (op/op) Mice is Cured by Injections of Macrophage colony-stimulating Factor; J. Exp,. Med. 1991, 173: 269-72.

(56) References Cited

OTHER PUBLICATIONS

Kolaskar, et al, A Semi-Empirical Method for Prediction of Antigenic Determinants on Protein Antigens, FEBS Lett. 276:172-174 (1990).
Komoyira, et. al., Design, synthesis and biological activity of amidinobicyclic compounds (derivatives of DX-9065a) as a factor Xa inhibitors: SAR study of S1 and aryl binding sites, Bioorg. Med. Chem. 12, 2099 (2004).
Kondoh, et al., An in vivo model for receptor tyrosine kinase autocrine/paracrine activation: auto-stimulated Kit receptor acts as a tumor promoting factor in papillomavirus-induced tumorigenesis; 1995, Oncogene 10:341-347.
Kondoh, et al., Establishment and Further Characterization of a Line of Transgenic Mice Showing Testicular Tumorigenesis at 100% Incidence, J. Urol. 152:2151-2154 (1994).
Kondoh, et al., Very High Incidence of Germ Cell tumorigenesis (Seminomagenesis) in Human Papillomavirus Type 16 Transgenic Mice; 1991, J. Virol. 65:3335-3339.
Konishi, et al., Brit J Cancer, (2003), 88:1223-1228.
Konno et al., "Influence of Different Polymers on the Crystallization Tendency of Molecularly Dispersed Amorphous Felodipine," Journal of Pharmaceutical Sciences 95(12):2692-2705 (2006).
Kroll, et al., A Malfunctional Prokaryotic Protein Expression System: Overproduction, Affinity Purification, and Selective Detection; (1993) DNA Cell. Biol. 12:441-53.
Kubo, et al., "Resequencing Analysis of the Human Tyrosine Kinase Gene Family in Pancreatic Cancer," Pancreas, (2009), 38(7):e200-e206.
Kubo, et al., "Resequencing and copy number analysis of the human tyrosine kinase gene family in poorly differentiated gastric cancer," Carcinogenesis, (2009), 30(11 ):1857-64.
Kundu, et al., Combinatorial Chemistry: Polymer Supported Synthesis of Peptide and Non-Peptide Libraries, Progress in Drug Research 53:89-156 (1999).
Kunisada, et al., Murine Cutaneous Mastocytosis and Epidermal Melanocytosis Induced by Keratinocyte Expression of Transgenic Stem Cell Factor; 1998, J. Exp. Med. 187:1565-1573.
Kunkel, "Rapid and Efficient Site-Specific Mutagenesis Without Phenotypic Selection" Proc. Natl. Acad. Sci. USA, (1985), 82:488-492.
Kunnimalaiyaan, et al., The Raf-1 pathway: a molecular target for treatment of select neuroendocrine tumors? Anticancer Drugs 17(2):139-42 (2006).
Kuntz, et al., A Geometric Approach to Macromolecule-Ligand Interactions, J. Mol. Biol. 161:269-288 (1982).
Kuntz, et al., Structure-Based Molecular Design, Acc. Chem. Res. 27:117-123 (1994).
Lahm, et al., Interleukin 4 Down-Regulates Expression of c-kit and Autocrine Stem Cell Factor in Human Colorectal Carcinoma Cells, Cell Growth & Differ 6:1111-1118 (1995).
Lala, et al. Role of nitric oxide in tumor progression: Lessons from experimental tumors, Cancer and Metastasis Reviews, 17:91-106 (1998).
Lam, et al., A new type of synthetic peptide library for identifying ligand-binding activity, Nature, 354: 82-84, 1991.
Lambros, et al., "Genomic profile of a secretory breast cancer with an ETV6-NTRK3 duplication," J. Clin. Pathol., (2009), 62(7):604-12.
Langham, et al., Metalation of Halogen-Metal Interconversion Reactions of Some Halogenated Phenyl Ethers, J. Am. Chem. Soc., vol. 63, 1941, pp. 545-549.
Lawicki, et al., The pretreratment plasma level and disgnostic utility of M-CSF in benign breast tumor and breast cancer patients, Clinica Chimica Acta, 371: 112-116, 2006.
Layzer, "Degenerative Diseases of the Nervous System," Cecil Textbook of Medicine, 20th Edition, (1996), 2:2050-2057.
Le Meur, et.al., Macrophage accumulation at a site of renal inflammation is dependent on the M-CSF/c-fms pathway; J Leukocyte Biology, 2002, 72: 530-537.
Lebl, et al., One-Bead-One-Structure Combinatorial Libraries, Biopolymers 37:177-198 (1995).
Lee, et al., HLA-DR-Triggered Inhibition of Hemopoiesis Involves Fas/Fas Ligand Interactions and is Prevented by c-kit Ligand, J. Immunol. 159:3211-3219 (1997).
Lee, et al., "FMS-like tyrosine kinase 3 inhibitors: a patent review," Expert Opinion Ther. Patents (2011), 21(4):483-503.
Lee, et al., Mast Cells: A Cellular Link Between Autoantibodies and Inflammatory Arthritis, Science 297:1689-1692 (2002).
Leuner, et al., "Improving drug solubility for oral delivery using solid dispersions," European Journal of Pharma. and Biopharma., (2000), 50(1):47-60.
Levin, et al., Neoplasms of the Central Nervous System, Cancer Principles & Practice of Oncology 2:2022-2082 (1997).
Levis, et al., "A FLT3 tyrosine kinase inhibitor is selectively cytotoxic to acute myeloid leukemia blasts harboring FL T3 internal tandem duplication mutations," Blood, (2001), 98:885-887.
Li, et al., Abrogation of c-kit/Steel Factor-Dependent Tumorigenesis by Kinase Defective Mutants of the c-kit Receptor: c-kit Kinase Defective Mutants as Candidate Tools for Cancer Gene Therapy, Canc. Res. 56:4343-4346 (1996).
Libby, Inflammation in atherosclerosis, Nature, 420:868-874 (2002).
Liparoto, et al., Biosensor Analysis of the Interleukin-2 Receptor Complex, Journal of Molecular Recognition 12:316-321 (1999).
Lipinski, et al., Experimental and Computational Approaches to Estimate Solubility and Permeability in Drug Discovery and Development Settings, Advanced Drug Delivery Reviews 23:3-25 (1997).
Lipschultz, et al., Experimental design for analysis of complex kinetics using surface plasmon resonance, Methods; (2000) 20(3):310-318.
Liu, et al., "Sorafenib Blocks the RAF/MEK/ERK Pathway, Inhibits Tumor Angiogenesis, and Induces Tumor Cell Apoptosis in Hepatocellular Carcinoma Model PLC/PRF/5," Cancer Res., (2006), 66:11852-11858.
Liu, et al., "CD68 Expression is Markedly Different in Crohn's Disease and the Colitis Associated with Chronic Granulomatous Disease," Inflamm. Bowel Dis., (2009), 15(8):1213-1217.
London, et al., Expression of Stem Cell Factor Receptor (c-kit) by the Malignant Mast Cells from Spontaneous Canine Mast Cell Tumors, 1996, J. Compar. Pathol. 115:399-414.
Longley, et al., Altered Metabolism of Mast-cell Growth Factor (c-kit Ligand) in Cutaneous Mastocytosis, 1993, New Engl. J. Med. 328:1302-1307.
Longley, et al., Chymase Cleavage of Stem Cell Factor Yields a Bioactive Soluble Product, Proc. Natl. Acad. Sci. 94:9017-9021 (1997).
Longley, et al., Somatic c-Kit Activating Mutation in Urticaria Pigmentosa and Aggressive Mastocytosis: Establishment of Clonality in a Human Mast Cell Neoplasm, Nat. Gen. 12:312-314 (1996).
Louvet, et al., "Tyrosine kinase inhibitors reverse type 1 diabetes in nonobese diabetic mice," Proc. Nat. Acad. Sci., (2008), 105(48):18895-18900.
Loveland, et al., Stem Cell Factor and c-kit in the Mammalian Testis: Lessons Originating from Mother Nature 19s Gene Knockouts, J. Endocrinol 153:337-344 (1997).
Lu, et al., Oriented Immobilization of Fab 19 Fragments on Silica Surfaces, Anal. Chem. 67:83-87 (1995).
Lukacs, et al., Stem Cell Factor (c-kit Ligand) Influences Eosinophil Recruitment and Histamine Levels in Allergic Airway Inflammation, J. Immunol. 156:3945-3951 (1996).
Luo, et al., Close Linkage with the RET Proto-Oncogene and Boundaries of Deletion Mutations in Autosomal Dominant Hirschsprung Disease, Hum Mol Genet. 2(11):1803-1808 (1993).
Lyman, et al., C-kit Ligand and Flt3 Ligand: Stem/Progenitor Cell Factors With Overlapping Yet Distinct Activities, Blood 91:1101-1134 (1998).
Ma, et al., The c-Kit Mutation Causing Human Mastocytosis is Resistant to ST1571 and Other KIT Kinase Inhibitors; Kinases with Enzymatic Site Mutations Show Different Inhibitor Sensitivity Profiles Than Wild-type Kinases and Those With Regulatory-Type Mutations, Blood 99:1741-1744 (2002).

(56) References Cited

OTHER PUBLICATIONS

Ma, et al., Indolinone Derivatives Inhibit Constitutively Activated KIT Mutants and Kill Neoplastic Mast Cells, 2000, J Invest Dermatol. 114:392-394.
Machens, et al., Modification of multiple endocrine neoplasia 2A phenotype by cell membrane proximity of RET mutations in exon 10, Endocrine-Related Cancer, (2009), 16:171-177.
Machida, et al., Mitogen-activated Protein Kinase Kinase Kinase Kinase 4 as a Putative Effector of Rap2 to Activate the c-Jun N-terminal Kinase, J. Biol. Chem. 279: 15711-15714 (2004).
Mack, et al., Functional identification of kinases essential for T-cell activation through a genetic suppression screen, Immunol. Lett. 96, 129-145 (2005).
Madden, et al., Synthetic Combinatorial Libraries: Views on Techniques and Their Application Perspectives in Drug Discovery and Design 2:269-285 (1994).
Madhusdan, et al., "Tyrosine kinase inhibitors in cancer therapy," Clinical Biochemistry, (2004), 37:618-635.
Malaysian Examination Report in Malaysian Application Serial No. PI20092547 dated Aug. 15, 2012.
Malaysian Substantive Examination Report dated Aug. 15, 2012 in Malaysian Application Serial No. PI20092040.
Malmborg, et al., BIAcore as a Tool in Antibody Engineering, Journal of Immunological Methods 183:7-13 (1995).
Malmqvist, BIAcore: an affinity biosensor system for characterization of biomolecular interactions, (1999) Biochemical Society Transactions 27:335-40.
Malmqvist, et al., Biomolecular Interaction Analysis: Affinity Biosensor Technologies for Functional Analysis of Proteins, Current Opinion in Chemical Biology 1:378-383 (1997).
Marchetti, et al., Frequent Mutations in the Neurotrophic Tyrosine Receptor Kinase Gene Family in Large Cell Neuroendocrine Carcinoma of the Lung, Hum. Mutat., (2008), 29(5):609-16.
Markiewicz, et al., Synthetic Oligonucleotide Combinatorial Libraries and Their Applications, II Farmaco 55:174-177 (2000).
Marshall, et al., "Blockade of colony stimulating Factor-1 (CSF-1) Leads to inhibition of DSS-induced colitis," Inflamm. Bowel Dis., (2007), 13(2):219-224.
Martin, Computer-Assisted Rational Drug Design, Methods Enz. 203:587-613 (1991).
Matayoshi, et al, Actions of brain-derived neurotrophic factor on spinal nociceptive transmission during inflammation in the rat, J Physiol. 569:685-95 (2005).
Matsumoto, Physical properties of solid molecular dispersions of indomethacin with poly(vinylpyrrolindone) and poly(vinylpyrrolidone-co-vinyl-acetate) in relation to indomethacin crystallization. Pharmaceutical Research, 16:11, 1722-1728, 1999.
Mazeas, et. al., Synthesis of new melatoninergic ligands including azaindole moiety. Heterocycles, 50:1065 (1999).
McArthur, et al., "Safety and efficacy of vemurafenib in BRAFV600E and BRAFV600K mutation-positive melanoma (BRUM-3): extended follow-up of phase 3, randomized, open-label study," Lancet. Oncol., (2014), 15(3), 323-332.
McCall, et al., Characterization of Anti-Mouse FcγRII Single-Chain Fv Fragments Derived from Human Phage Display Libraries, Immunotechnology 4:71-87 (1998).
McDermott, et al., "Identification of genotype-correlated sensitivity to selective kinase inhibitors by using high throughput tumor cell line profiling," PNAS, (2007), 104(50):19936-19941.
McPherson, Current Approaches to Macromolecule Crystallization, Eur. J. Biochem. 189:1-23 (1990).
Mekori, et al., Transforming Growth Factor-βPrevents Stem Cell Factor-Mediated Rescue of Mast Cells from Apoptosis After IL-3 Deprivation, 1994, J. Immunol 153:2194-2203.
Mekori, et al., The Role of c-Kit and Its Ligand, Stem Cell Factor, in Mast Cell Apoptosis, 1995, Int. Arch. Allergy Immunol. 107:136-138.
Meltzer, The pharmacological basis for the treatment of perennial allergic rhinitis and non-allergic rhinitis with topical corticosteroids, 1997, Aller. 52:33-40.

Meng, et al., Automated Docking with Grid-Based Energy Evaluation, J. Compt. Chem. 13:505-524 (1992).
Menke, et al., "Sunlight triggers cutaneous lupus through a CSF-1-dependent mechanism in MRL-Fas$^{lpr}$ mice," Journal of Immunology, (2008), 181:7367-7379.
Merour, Synthesis and Reactivity of 7-Azaindoles (1H-Pyrrolo[2,3-b]pyridine), Curr. Org. Chem. 2001, 5:471-506.
Merritt, Solution Phase Combinatorial Chemistry, Comb Chem High Throughput Screen 1:57-72 (1998).
Metcalf, Lineage Commitment in the Progeny of Murine Hematopoietic Preprogenitor Cells: Influence of Thrombopoietin and Interleukin 5, Proc. Natl. Acad. Sci. USA 95:6408-6412 (1998).
Metcalfe, Classification and Diagnosis of Mastocytosis: Current Status, 1991, J. Invest. Derm 93:2S-4S.
Metcalfe, et al., Mast Cells, Physiol. Rev. 77:1033-1079 (1997).
Mettey, et al., "Aloisines, a New family of CDK.GSK-3 Inhibitors. SAR Study, Crystal Structure in Complex with CDK2, Enzyme Selectivity, and Cellular Effects," J. Med. Chem., (2003), 46:222-236.
Meula Pomeda, et al., Efecto De Codisolventes Y Dispersiones Solida De Polivinilpirrolidona K-30 En La Solubilidad Tel Tiabendazol, Departamento de Farmacia y Tecnologia Farmaceutica. Facultad de Farmacia. Universidad de Alcala, pp. 85-87 (2002) (No English Translation Available).
Miller, et al., FLOG: A System to Select Quasi-Flexible Ligands Complementary to a Receptor of Known Three-Dimensional Structure, J. Comp. Aided Molec. Design 8:153-174 (1994).
Minakata et al., Functionalization of 1H-Pyrrolo[2,3-b]pyridine, Bulletin of the Chemical Society of Japan (1992), 65(11): 2992-2997.
Minakata, et al., Regioselective Funtionalization of 1H-Pyrrolo[2,3-b]pyridine via its N-Oxide, Synthesis pp. 661-663 (1992).
Miranker et al, Functionality Maps of Binding Sites: A Multiple Copy Simultaneous Search Method, Proteins: Structure, Function, and Genetics 11:29-34 (1991).
Mitra, et al., Fluorescence Resonance Energy Transfer Between Blue-Emitting and Red-Shifted Excitation Derivatives of the Green Fluorescent Protein, Gene 173:13-17 (1996).
Miyaura, Palladium-Catalyzed Cross-Coupling Reactions of Organoboron Compounds, Chem. Rev. 1995, 95:2457.
Mokhtari, et al, Clinical Science, 118(4):241-247 (2010).
Mol, et al. Structural Basis for the Autoinhibition and STI-571 Inhibition of c-Kit Tyrosine Kinase, J. Biol. Chem. 279:31655-31663 (2004).
Mol, et al., Structure of a c-Kit Product Complex Reveals the Basis for Kinase Transactivation, J. Biol. Chem. 278:31461-31464 (2003).
Morgan, Isolation and Characterization of a Cloned Growth Factor Dependent Macrophage Cell Line, BAC1.2F5, Journal of Cellular Physiology, 130:420-427 (1987).
Motoyoshi, Biological activities and clinical application of M-CSF, Int J Hematol. 1998, 67:109-22.
Murphy, et al., "Expression of macrophage colony-stimulating factor receptor is increased in the AβPP$^{V717F}$ transgenic mouse model of Alzheimer's disease," Am. J. of Pathology, (2000), 157(3):895-904.
Murty, et al., A Genetic Perspective of Male Germ Cell tumors, 1998, Sem. Oncol. 25:133-144.
Naclerio, et al., Rhinitis and Inhalant Allergens, JAMA 278:1842-1848 (1997).
Nagafuji and Cushman, A General Synthesis of Pyrroles and Fused Pyrrole Systems from Ketones and Amino Acids, J. Org. Chem. 61:4999-5003 (1996).
Nagata, et al., Elevated Expression of the Proto-Oncogene c-kit in Patients with Mastocytosis, Leukemia 12:175-181 (1998).
Nahm, N-Methoxy-N-Methylamides as Effective Acylating Agents, Tetrahedron Lett. 22(39):3815-3818 (1981).
Nakagawara, et al., Expression and Function of TRK-B an BDNF in Human Neuroblastomas, Mol. Cell Biol. 14:759-767 (1994).
Nakai, et al., New Potent Antagonists of Leukotrienes C4 and D4. 1. Synthesis and Structure-Activity Relationships, J.Med.Chem, 31:84-91 (1988).

(56) References Cited

OTHER PUBLICATIONS

Nassentein, et al, The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma, J. Exp. Med. 198:455-467 (2003).
Natali, et al., "Breast cancer is associated with loss of the c-*kit* oncogene product," Int. J. Cancer (1992) 52:713-717.
Navaza, J., AMoRe: an Automated Package for Molecular Replacement, Acta Cryst. A50:157-163 (1994).
Neidle, et al., Molecular Modeling to Study DNA Intercalation by Anti-Tumor Drugs, Methods Enz. 203:433-458 (1991).
New Zealand Office Action dated Aug. 16, 2012 in related NZ Patent Appl Serial No. 594398.
Ng, et al., Engineering Protein-Lipid Interactions: Targeting of Histidine-Tagged Proteins to Metal-Chelating Lipid Monolayers, Langmuir 11:4048-4055 (1995).
Nicholls, et al., Protein Folding and Association: Insights From the Interfacial and Thermodynamic Properties of Hydrocarbons, Proteins 11:281-296 (1991).
Nichols, et al., Development of a Scintillation Proximity Assay for Peroxisome Proliferator-Activated Receptor γ Ligand Binding Domain, Anal. Biochem. 257:112-119 (1998).
Niihori, T. et al., Germline KRAS and BRAF mutations in cardio-facio-cutaneous syndrome, Nature Genet. 38(3):294-6 (2006).
Non Final Office Action dated Apr. 18, 2012 in related U.S. Appl. No. 12/958,376.
Norwegian Office Action dated Aug. 15, 2012 in related Norwegian Patent Appl No. 20076659 (With English Translation).
Notice of Allowance dated Nov. 19, 2012 for related U.S. Appl. No. 13/546,923.
Notice of Allowance dated Dec. 26, 2007 for U.S. Appl. No. 11/016,350.
Notice of Allowance dated Jun. 18, 2010 for U.S. Appl. No. 11/473,347.
Notice of Allowance dated Jun. 6, 2008 for U.S. Appl. No. 11/154,988.
Notice of Allowance for U.S. Appl. No. 11/473,347 dated Sep. 8, 2010.
Notice of Allowance for U.S. Appl. No. 11/986,667 dated Aug. 6, 2010.
Notice of Allowance for U.S. Appl. No. 12/082,665 dated Jul. 26, 2011.
Notice of Allowance for U.S. Appl. No. 12/244,730 dated Jan. 6, 2011.
Notice of Allowance for U.S. Appl. No. 12/244,730 dated Jul. 27, 2010.
Notice of Allowance for U.S. Appl. No. 12/616,079 dated Oct. 25, 2012.
Notice of Allowance for U.S. Appl. No. 12/721,500 dated Nov. 2, 2011.
Notice of Allowance for U.S. Appl. No. 12/773,798 dated Feb. 9, 2012.
Notice of Allowance for U.S. Appl. No. 13/546,923 dated Nov. 19, 2012.
Notice of Allowance for U.S. Appl. No. 12/467,194 dated Dec. 5, 2011.
Notification on the Result of Substantive Examination dated Oct. 17, 2014 for Vietnamese Application No. 1-2010-02238.
Notification Prior to Examination for Israeli Application No. 199194 dated May 4, 2010.
Novelty Search Report dated Sep. 24, 2009 for Gulf Cooperation Council Application No. GCC/P/2006/6469.
Ochs, et al, A phase I/II trial of recombinant methionyl human brain derived neurotrophic factor administered by intrathecal infusion to patients with amyotrophic lateral sclerosis, Amyotroph Lateral Scler Other Motor Neuron Disord. 1:201-6 (2000).
Odegaard et al. "Macrophage-specific PPARg controls alternative activation and improves insulin resistance," Nature, (2007), 447:1116-1121.
Office Action (with English Translation) dated Apr. 23, 2012 in related Israeli Patent Application No. 199194.
Office Action and Search Report for Taiwanese Application No. 100113512 dated Dec. 15, 2014.
Office Action dated Feb. 7, 2014 for Chinese Application No. 20110084299.
Office Action dated Mar. 25, 2014 for Chinese Application No. 201210012143.
Office Action dated Apr. 18, 2012 in related Israeli Patent Application Serial No. 198624 (English Translation).
Office Action dated Apr. 23, 2012 in related Dominican Republic Patent Application Serial No. P2011-0291 (English Translation).
Office Action dated Jan. 10, 2012 in related Canadian Patent Application Serial No. 2,738,573.
Office Action dated Jan. 23, 2012 in related U.S. Appl. No. 11/961,901.
Office Action dated Mar. 21, 2012 in related New Zealand Patent Application No. 577612.
Office Action dated May 16, 2012 in related Mexican Patent Application No. MX/a/2009/005428.
Office Action dated May 21, 2013 in related Japenese Patent Application No. 2012-503676.
Office Action Eurasian Application No. 201290210 dated May 2014.
Office Action for Chinese Application No. 2012800170177 dated Jul. 8, 2014.
Office Action for European Application No. 11173701.1 dated Jan. 13, 2014.
Office Action for Thai Application No. 1301004352 dated Sep. 29, 2014.
Office Action for Ukraine Application No. A200800780 dated Jul. 12, 2010.
Office Action in Australian Application No. 2006261993 dated Aug. 15, 2011.
Office Action in Australian Application No. 2012214762 dated Mar. 23, 2014.
Office Action in Canadian Application No. 2670362 dated Jul. 14, 2014.
Office Action in Canadian Application No. 2670362 dated Dec. 5, 2013.
Office Action in Canadian Application No. 2826123 dated Jun. 30, 2014.
Office Action in Chilean Application No. 2011-001903 dated Nov. 28, 2013.
Office Action in Chilean Application No. 2012-1303 dated Nov. 4, 2014.
Office Action in Chilean Application No. 2228-2013 dated Dec. 18, 2014.
Office Action in Chinese Application No. 200780050245.3 dated Jul. 20, 2011.
Office Action in Chinese Application No. 20108001288.0 dated Oct. 21, 2014.
Office Action in Chinese Application No. 201080012888.0 dated Mar. 10, 2014.
Office Action in Chinese Application No. 201080060838.X dated Oct. 29, 2014.
Office Action in Chinese Application No. 201310470059.2 dated Nov. 4, 2014.
Office Action in Colombia Application No. 11-111.102 dated Jan. 4, 2014.
Office Action in Colombian Application No. 08-005.567 dated Sep. 9, 2011.
Office Action in Colombian Application No. 09-052-610 dated Dec. 23, 2013.
Office Action in Colombian Application No. 12-081.901 dated Jun. 28, 2014.
Office Action in Colombian Application No. 13-187.418 dated Oct. 20, 2014.
Office Action in Costa Rican Application No. 2013-374 dated Feb. 25, 2014.
Office Action in Erasian Application No. 201391019 dated Oct. 6, 2014.

(56) References Cited

OTHER PUBLICATIONS

Office Action in Eurasian Application No. 201190098 dated Apr. 13, 2014.
Office Action in Eurasian Application No. 20119098 dated Jun. 16, 2014.
Office Action in European Application 10722860.3 dated Aug. 21, 2014.
Office action in Georgia Application No. AP2010012739 dated Oct. 9, 2014.
Office Action in Indian Application No. 1879/KOLNP/2009 dated Jul. 11, 2014.
Office Action in Indonesian Application No. W-00 2011-02778 dated Nov. 7, 2014.
Office Action in Israeli Application No. 214328 dated Jul. 31, 2013.
Office Action in Israeli Application No. 219418 dated Oct. 6, 2014.
Office Action in Israeli Application No. 219567 dated Jul. 31, 2014.
Office Action in Japanese Application No. 2008-518402 dated Nov. 29, 2011.
Office Action in Japanese Application No. 2009-538496 dated Jan. 29, 2013.
Office Action in Japanese Application No. 2009-538496 dated Aug. 20, 2013.
Office Action in Japanese Application No. 2012-538002 dated Sep. 16, 2014.
Office Action in Japanese Application No. 2012-546158 dated Dec. 2, 2014.
Office Action in Japanese Application No. 2013-552610 dated Nov. 4, 2014.
Office Action in Korean Application No. 10-2009-7012836 dated May 29, 2014.
Office Action in Malaysian Applictaion No. PI2011004969 dated Apr. 30, 2014.
Office Action in Mexican Application No. MX/a/2011/008303 dated Sep. 11, 2014.
Office Action in New Zealand Application No. 594398 dated Aug. 16, 2012.
Office Action in New Zealand Application No. 617526 dated Aug. 14, 2014.
Office Action in Norwegian Application No. 20076659 dated Aug. 15, 2012.
Office Action in Peru Applicantion No. 1471-2011 dated Mar. 23, 2014.
Office Action in Peruvian Application No. 1602-2007 dated Sep. 2, 2011.
Office Action in Peruvian Application No. 1796-2007 dated Sep. 15, 2011.
Office Action in Peruvian Application No. 1867-2011 dated Nov. 7, 2014.
Office Action in Philippine Application No. 12009501009 dated Jul. 27, 2012.
Office Action in Philippine Application No. 12009501009 dated Nov. 24, 2011.
Office Action in Philippine Application No. 1-2009-501241 dated Jul. 27, 2012.
Office Action in Philippine Application No. 1-2011-501775 dated Aug. 27, 2014.
Office Action in Russian Application No. 2009117475 dated Jul. 26, 2011.
Office Action in Russian Application No. 2009122436 dated Dec. 2, 2011.
Office action in Russian Application No. 2011101140 dated Dec. 24, 2014.
Office Action in Russian Application No. 2012125070 dated Dec. 5, 2014.
Office Action in Russian Application No. 2012131373 dated Jan. 14, 2015.
Office Action in Taiwan Application No. 095122373 dated Dec. 9, 2011.
Office Action in Taiwan Application No. 099110011 dated Jun. 26, 2012.
Office Action in Taiwan Application No. 099138273 dated Aug. 12, 2014.
Office Action in Taiwan Application No. 102123382 dated Nov. 16, 2013.
Office Action in Thailand Application No. 1201002096 dated May 13, 2014.
Office Action in U.S. Appl. No. 12/721,500 dated May 13, 2011.
Office Action in Ukraine Application No. a 2011 09548 dated Jun. 4, 2014.
Office Action in U.S. Appl. No. 12/467,194 dated Feb. 3, 2011.
Office Action in U.S. Appl. No. 11/016,350 dated Aug. 2, 2007.
Office Action in U.S. Appl. No. 11/961,901 dated Aug. 4, 2011.
Office Action in U.S. Appl. No. 12/082,665 dated Nov. 8, 2010.
Office Action in U.S. Appl. No. 12/467,194 dated Jun. 24, 2011.
Office Action in U.S. Appl. No. 12/669,450 dated Dec. 27, 2012.
Office Action in U.S. Appl. No. 12/733,798 dated Jan. 20, 2011.
Office Action in U.S. Appl. No. 12/773,798 dated Jul. 25, 2011.
Office Action in U.S. Appl. No. 12/906,980 dated Oct. 17, 2012.
Office Action in U.S. Appl. No. 12/939,998 dated Mar. 21, 2013.
Office Action in U.S. Appl. No. 12/939,998 dated Oct. 18, 2012.
Office Action in U.S. Appl. No. 12/958,379 dated Jul. 17, 2012.
Office Action in U.S. Appl. No. 12/958,379 dated Nov. 14, 2012.
Office Action in U.S. Appl. No. 12/981,427 dated Mar. 5, 2013.
Office Action in U.S. Appl. No. 13/243,748 dated Jun. 27, 2013.
Office Action in U.S. Appl. No. 13/243,748 dated Dec. 20, 2013.
Office Action in U.S. Appl. No. 13/546,923 dated Sep. 18, 2012.
Office Action in U.S. Appl. No. 13/786,219 dated Jul. 21, 2014.
Office Action in U.S. Appl. No. 13/786,219 dated Nov. 8, 2013.
Office Action in U.S. Appl. No. 13/793,917 dated Jul. 21, 2014.
Office action in U.S. Appl. No. 13/802,106 dated Dec. 23, 2014.
Office Action in U.S. Appl. No. 13/866,469 dated Oct. 31, 2013.
Office Action in U.S. Appl. No. 14/033,291 dated Sep. 26, 2014.
Office Action in U.S. Appl. No. 14/033,291 dated Dec. 17, 2013.
Ohno, et al. "A c-fms tyrosine kinase inhibitor, KI202227, suppresses osteoclast differentiation and osteolytic bone destruction in a bone metastasis model," Mol. Cancer Ther., (2006), 5(11):2634-2643.
Ohno, et al., "The orally-active and selective c_FMS tyrosine kinase inhibitor Ki20227 inhibits disease progression in a collagen-induced arthritis mouse model," Eur. J Immunol., (2008), 38:1-9.
Okada, et al., Gene Therapy Against an Experimental Glioma Using Adeno-Associated Virus Vectors, Gene Ther. 3:957-964 (1996).
Okayama, et al., Human Lung Mast Cells are Enriched in the Capacity to Produce Granulocyte-Macrophage Colony-Stimulating Factor in Response to IgE-Dependent Stimulation, Eur. J. Immunol. 28:708-715 (1998).
Okayama, et al., Activation of Eosinophils with Cytokines Produced by Lung Mast Cells, Int. Arch. Aller. Immunol. 114(suppl. 1):75-77 (1997).
Olah, et al., Synthetic Methods and Reactions: Part 209. Improved Preparation of Aldehydes and Ketones from N,N-Dimethylamides and Grignard Reagents, Synthesis pp. 228-230 (1984).
Opposition in Chilean Application No. 1180-2012 dated Nov. 26, 2014.
O'Shannessy, Interpretation of Deviations from Pseudo-First-Order Kinetic Behavior in the Characterization of Ligand Binding by Biosensor Technology, Analytical Biochemistry 236:275-283 (1996).
O'Shannessy, Determination of kinetic rate and equilibrium binding constants for macromolecular interactions: a critique of the surface plasmon resonance literature, (1994) Current Opinions in Biotechnology, 5:65-71.
Ottoni, et al., Efficient and Simple Methods for the Introduction of the Sulfonyl, Acyl and Alkyl Protecting Groups on the Nitrogen of Indole and its Derivatives, Tetrahedron 54:13915-13928 (1998).
Otwinowski, Maximum Likelihood Refinement of Heavy Atom Parameters, Dept. of Molecular Biophysics and Biochemistry pp. 80-86 (1991).
Owicki, et al., Application of Fluorescence Polarization Assays in High-Throughput Screening, (1997), Genetic Engineering News, 17:27.
Panitumumab, "In Combination with Cisplatin/Gemacitabine", (2011), http://clinicaltrials.gov/ct2/show/NCT0132054.

(56) References Cited

OTHER PUBLICATIONS

Parker, et al., Development of High Throughput Screening Assays Using Fluorescence Polarization: Nuclear Receptor-Ligand-Binding and Kinase/Phosphatase Assays, J Biomol Screen 5:77-88 (2000).
Partial European Search Report dated Oct. 26, 2011 for EP Patent Application No. 11173701.1.
Patani, et al, "Bioisosterism: a rational approach in drug design," Chem Rev, (1996), 96:3147-3176.
Pearce, et al., "Failure modes in anticancer drug discovery and development," Cancer Drug Design and Discovery Edited by Stephen Neidle, (2008), Chapter 18:424-435.
Perrin, Nucleic Acids for Recognition and Catalysis: Landmarks, Limitations, and Looking to the Future, Combinatorial Chemistry & High Throughput Screening 3:243-269 (2000).
Petty, et al, The effect of systemically administered recombinant human nerve growth factor in healthy human subjects. Ann Neurol. 36:244-6 (1994).
Pflugrath, et al., Crystal Structure Determination, Refinement and the Molecular Model of the x-Amylase Inhibitor Hoe-467A, J. Mol. Biol. 189:383-386 (1986).
Pierce, et al., Local anaesthetics. I. beta-Monoaklylaminoethyl Esters of Alkoxybenzoic Acids, J. Am. Chem. Soc., vol. 64, pp. 1691-1694 (1942).
Pignon, C-kit mutations and mast cell disorders a model of activating mutations of growth factor receptors, Hermatol Cell Ther 39:114-116 (1997).
Plunkett, et al, A Silicon-Based Linker for Traceless Solid-Phase Synthesis, J. Org. Chem. 60:6006-6007 (1995).
Poul, et al., Selection of Tumor-Specific Internalizing Human Antibodies from Phage Libraries, J. Mol. Biol. 301:1149-1161 (2000).
Prada, et al., "Neurofibroma-associated Macrophages Play Roles in Tumor Growth and Response to Pharmacological Inhibition," Acta Neuropathol, (2013), 125:159-168.
Pratilas, et al., "Marker gene showing changes in levels of expression in response to antineoplastic drug therapy and their use of chemotherapy", Hcalplus (2008), 670875.
Price, et al.; Summary report on the ISOBM TD-4 Workshop: analysis of 56 monoclonal antibodies against the MUC1 mucin, (1998) Tumour Biology 19 Suppl 1:1-20.
Prien, Target-family-oriented focused libraries for kinases—Conceptual design aspects and commercial availability. ChemBioChem, (2005), 6:500-505.
Qiao, et al., Role of Macrophage Colony-Stimulating Factor in Atherosclerosis, Am. J. Path. 1997;150:1687-1699.
Rajavashisth, et. al., Heterozygous Osteopetrotic (op) Mutation Reduces Atherosclerosis in LDL Receptor-deficient Mice, J. Clin. Invest. 1998;101:2702-2710.
Rajpert-De Meyts, et al., Expression of the c-kit Protein Product in Carcinoma-in-situ and Invasive Testicular Germ Cell Tumours, Int. J. Androl. 17:85-92 (1994).
Rapp, et al., "Raf kinases in lung tumor development," Advan. Enzyme Regul. (2003) 43:183-195.
Remington: The Science and Practice of Pharmacy, (1995) II:1454-1460.
Ricotti, et al., c-kit is Expressed in Soft Tissue Sarcoma of Neuroectodermic Origin and Its Ligand Prevents Apoptosis of Neoplastic Cells, Blood 91:2397-2405 (1998).
Ridge, et al, FMS mutations in myelodysplastic, leukemic, and normal subjects, Proc. Nat. Acad. Sci., 1990, 87:1377-1380.
Ritz, et al., "Elevated blood levels of inflammatory monocytes (CD14+CD16+) in patients with complex regional pain syndrome," Clin. Exper. Immunology, (2011), 1-10.
Roberts, et al., "Targeting the Raf-MEK-ERK mitogen-activated protein kinase cascade for the treatment of cancer," Oncogene (2007) 26:3291-3310.
Roberts, et al., Generation of an antibody with enhanced affinity and specificity for its antigen by protein engineering, (1987) Nature 328:731-734.
Robinson, et al., Stimulation of Bone Marrow Colony Growth in Vitro by Human Urine; Blood, 1969, 33:396-9.
Robison, et al, 7-Azaindole. I. Synthesis and Conversion to 7-Azatryptophan and Other Derivatives, J. Am. Chem. Soc. 77:457-460 (1955).
Rodan, et al., "Therapeutic Approaches to Bone Diseases," Science, (2000), 289:1508-1514.
Rodriguez-Viciana, et al., "Germline Mutations in Genes Within the MAPK Pathway Cause Cardio-facio-cutaneous Syndrome," Science, (2006), 311:1287-1290.
Rosenfeld, Human artificial chromosomes get real, (1997) Nat. Genet. 15:333-335.
Rosnet, et al., Isolation and Chromosomal Localization of a Novel FMS-like Tyrosine Kinase Gene, Genomics, (1991), 9:380-385.
Ryan, et al., Role for the Stem Cell Factor/KIT Complex in Schwann Cell Neoplasia and Mast Cell Proliferation Associated with Neurofibromatosis, 1994, J. Neuro. Res. 37:415-432.
Saify, et al, Database CAS on STN (Columbus, OH, USA) No. 124:170379, Synthesis of some 2-azaindole derivatives: their cyctotoxicity and antibacterial activity, abstract, (1996), See RN 271-63-6.
Saify, et al., Synthesis of some 7-azaindole derivatives: Their cytotoxicity and antibacterial activity, Pakistan Journal of Scientific and Industrial Research, 37(10): 439-441, 1994.
Saiki, Amplification of Genomic DNA, in PCR Protocols, Innis et al., Eds., Academic Press, San Diego, CA 1990, pp. 13-20.
Sambrook, et al., Introduction of Recombinant Vectors into Mammalian Cells 1D Molecular Cloning: A Laboratory Manual 2:16. 30-16.37 (1989).
Sandlow, et al., Expression of c-KIT and its Ligand, Stem Cell Factor, in Normal and Subfertile Human Testicular Tissue, 1996, J. Androl. 17:403-408.
Santoro, et al., The ret Proto-Oncogene is Consistently Expressed in Human Pheochromocytomas and Thyroid Medullary Carcinomas, Oncogene, 5(10):1595-1598 (1990).
Sathornsumetee, et al., "AAL881, a Novel Small Molecule Inhibitor of RAF and Vascular Endothelial Growth Factor Receptor Activities, Blocks the Growth of Malignant Glioma," Cancer Res., (2006), 66:8722-8730.
Sawada et al., 4-(Benzoylindolizinyl)butyric acids; Novel nonsteroidal inhibitors of steroid 5;1-reductase. III, Chemical and Pharmaceutical Bulletin (2001), 49(7): 799-813.
Sawada, et al., Role of Cytokines in Leukemic type Growth of Myelodysplastic CD34+ Cells, 1996, Blood 88:319-327.
Sawai, et al., Aberrant growth of granulocyte-macrophage progenitors in juvenile chronic myelogenous leukemia in serum-free culture, 1996, Exp. Hem. 2:116-122.
Scheffner, et al., The E6 Oncoprotein Encoded by Human Papillomavirus Types 16 and 18 Promotes the Degredation of p53, Cell 63:1129-1136 (1990).
Schiemann, p-Fluorobenzoic Acid, Org. Syn. Coll. vol. 2:299, 1943.
Schneider, et al., Functional Purification of a Bacterial ATP-Binding Cassette Transporter Protein (MaIK) from the Cytoplasmic Fraction of an Overproducing Strain, (1995) Protein Expr. Purif. 6435:10.
Schneller, et. al., Synthesis of 4-Amino-1 H-pyrrolo[2,3-b]pyridine {1,7-Dideazaadenine) and 1H-Pyrrolo[2,3-b]pyridine-4-ol (1,7-Dideazahypoxanthine), J. Org. Chem. 1980, 45:4045.
Schuhmann, et al., Immobilization of Enzymes on Langmuir-Blodgett Films via a Membrane-Bound Receptor. Possible Applications for Amperometric Biosensors, Adv. Mater. 3:388-391 (1991).
Schummer, et al., Inexpensive Handheld Device for the Construction of High-Density Nucleic Acid Arrays, Biotechniques 23:1087-1092 (1997).
Schweizer, et al., Combinatorial Synthesis of Carbohydrates, Curr Opin. Chem. Biol., 3:291-298 (1999).
Sclabas et al., "Overexpression of Tropomysin-Related Kinase Bin Metastatic Human Pancreatic Cancer Cells," Clin. Cancer. Res, (2005), VII :440-449.
Search Report for European Application No. 04814626.0 dated Aug. 4, 2009.
Search Report for European Application No. 12745360.3 dated Jul. 23, 2014.

(56) References Cited

OTHER PUBLICATIONS

Search Report for Taiwan Patent Application No. 094120055 dated Aug. 25, 2011.
Secor, et al., Mast cells are essential for early onset and severe disease in a murine model of multiple sclerosis. J. Exp. Med. 5:813-821 (2000).
Selvin, Fluorescence Resonance Energy Transfer, Meth. Enzymol. 246:300-345 (1995).
Serajuddin, "Solid Dispersion of Poorly Water-Soluble Drugs: Early Promises, Subsequent Problems, and Recent Breakthroughs," J. Pharm. Sci., (1999), 8(10):1058-1066.
Shah et al., "Development of Novel Microprecipitated Bulk Power (MBP) Technology for Manufacturing Stable Amorphous Formulations of Poorly Soluble Drugs," International Journal of Pharmaceutics, vol. 438, 2012, pp. 53-60.
Shah et al., "Improved Human Bioavailability of Vermurafenib, a Practically Insoluble Drug, Using an Amorphous Polymer-Stabilized Solid Dispersion Prepared by a Solvent-Controlled Coprecipitation Process," Journal of Pharmaceutical Sciences, 2012, pp. 1-15.
Shah, et al. "Approaches for improving bioavailability of poorly soluble drugs," Pharmaceutical Dosage Forms, (2008), 51-104.
Shan, et al., Prodrug strategies based on intramolecular cyclization reactions. Journal of Pharmaceutical Sciences, 86:7, 765-767, 1997.
Sheets, et al., Efficient Construction of a Large Nonimmune Phage Antibody Library: The Production of High-Affinity Human Single-Chain Antibodies to Protein Antigens, Proc Natl Acad Sci USA 95:6157-6162 (1998).
Shibata, et al, Alveolar macrophage deficiency in osteopetrotic mice deficient in macrophage colony-stimulating factor is spontaneously corrected with age and associated with matrix metalloproteinase expression and emphysema, Blood 98: pp. 2845-2852 (2001).
Siegel, et al., Mass Spectral Analysis of a Protein Complex Using Single-Chain Antibodies Selected on a Peptide Target: Applications to Functional Genomics, Journal of Molecular Biology 302:285-293 (2000).
Sigal, et al., A Self-Assembled Monolayer for the Binding and Study of histidine-Tagged Proteins by Surface Plasmon Resonance, (1996) Anal. Chem. 68:490-497.
Silverman, Prodrugs and Drug Delivery Systems, The Organic Chemistry of Drug Design and Drug Action, (1992), 352-399.
Simone, Oncology: Introduction, Cecil Textbook of Medicine, 20th Edition, (1996) 1:1004-1010.
Small, et al., "STK-I, the human homolog of Flk-2/Flt-3, is selectively expressed in CD34+ human bone marrow cells and is involved in the proliferation of early progenitor/stem cells," Proc. Nat. Acad. Sci., (1994),91:459-463.
Smalley, et al., C-KIT signaling as the driving oncogenic event in sub-groups of melanomas. Histol Histopathol, 24:643-650, 2009.
Smith, et al., "The Role of kinase inhibitors in the treatment of patients with acute myeloid leukemia," Am Soc Clin Oncol Educ Book, (2013), pp. 313-318.
Solinas-Toldo, et al., Matrix-Based Comparative Genomic Hybridization Biochips to Screen for Genomic Imbalances, Genes, Chromosomes & Cancer 20:399-407 (1997).
Song, et al., Isomerism of Bis(7-azaindolyl)methane, Organic Letters (2002), 4:23, 4049-4052, Table of content p. 1-16 and Supporting information p. 1-15.
Soreafenib, National Cancer Institute, (2012), http://www.cancer.gov/cancertopics/druginfo/sorafenibtosylate.
Specchia, et al., "Constitutive expression of iL-Iβ, M-CSF and c-fms during the myeloid blastic phase of chronic myelogenous leukaemia," Br J Haematol., (Mar. 1992), 80(3):310-316.
Sperling, et al., Expression of the Stem Cell Factor Receptor C-Kit (CD117) in Acute Leukemias, Haemat 82:617-621 (1997).
Stanulla, et al., Coexpression of Stem Cell Factor and Its Receptor c-Kit in Human Malignant Glioma Cell Lines, Act Neuropath 89:158-165 (1995).
Steinman, Multiple sclerosis: A coordinated immunological attack against myelin in the central nervous system. Cell 85:299-302 (1996).
Strohmeyer, et al., Expression of the C-kit Proto-Oncogene and its Ligand Stem Cell Factor (SCF) in Normal and Malignant Human Testicular Tissue, 1995, J. Urol. 153:511-515.
Strohmeyer, et al., Expression of the hst-1 and c-kit Protooncogenes in Human Testicular Germ Cell Tumors, Canc. Res. 51:1811-1816 (1991).
Su, Synthesis of bromo-substituted Idoxyl Esters for Cytochemical Demonstration of Enzyme Activity, J. Am. Chem. Soc., 82:1187 (1960).
Substantive Examination Report for Philippines Application No. 1/2011/501628 dated Nov. 28, 2014.
Substantive Examination Report for Philippines Application No. 1/2013/501633 dated Dec. 22, 2014.
Substantive Report for Chilean Application No. 2012-001180 dated Nov. 26, 2014.
Substantive Report in Chilean Application No. 2238-2011 dated Oct. 14, 2014.
Sun, et al., Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases, J. Med. Chem. 42:5120-5130 (1999).
Sun, Recent Advances in Liquid-Phase Combinatorial Chemistry, Comb. Chem. & High Throughput Screening 2:299-318 (1999).
Supplemental Notice of Allowance dated Jul. 23, 2008 for U.S. Appl. No. 11/154,988.
Supplemental Notice of Allowance dated Sep. 8, 2008 for U.S. Appl. No. 11/154,988.
Supplementary European Search Report for EP Application No. 11772612, dated Oct. 21, 2013.
Supplementary European Search Report for European Patent Application No. EP1278 9648 dated Jun. 23, 2014.
Supplementary Search Report for European Application No. 04814626.0 dated Aug. 4, 2009.
Tada, et al., Analysis of Cytokine Receptor Messenger RNA Expression in Human Glioblastoma Cells and Normal Astrocytes by Reverse-Transcription Polymerase Chain Reaction, J. Neuro 80:1063-1073 (1994).
Taiwanese Office Action dated Jun. 26, 2012 in related Taiwan Appl Serial No. 099110011 (With English Translation).
Takahashi, et al, Ret Transforming Gene Encodes a Fusion Protein Homologous to Tyrosine Kinases, Mol Cell Biol. 7:1378-1385 (1987).
Takahashi, et al., Activation of a Novel Human Transforming Gene, ret, by DNA Rearrangement, Cell 42(2):581-588 (1985).
Takahashi, et al., Cloning and Expression of the ret Proto-Oncogene Encoding a Tyrosine Kinase with Two Potential Transmembrane Domains, Oncogene 3(5):571-578 (1988).
Tang, X. et al., An RNA interference-based screen identifies MAP4K4/NIK as a negative regulator of PPARy, adipogenesis, and insulin-responsive hexose transport, Proc. Natl. Acad. Sci. U. S. A. 103:2087-2092 (2006).
Tanno, et al., "Evaluation of Hypromellose Acetate Succinate (HPMCAS) as a Carrier in Solid Dispersions," Drug Development and Industrial Pharmacy 30(1):9-17 (2004).
Taylor et al. The Rapid Generation of Oligonucleotide-directed Mutations at High Frequency Using Phosphorothloate-Modified DNA; (1985) Nucl. Acids Res. 13:8764-8785.
Teitelbaum, Bone Resorption by Osteoclasts, Science. 289:1504 (2000).
Thibault, et. al., Concise and Efficient Synthesis of 4-fluoro-1H-pyrrolo[2,3-b] pyridine, Org. Lett. 5:5023-5025 (2003).
Thomas, et al, The Eosinophil and its Role in Asthma, Gen. Pharmac 27:593-597 (1996).
Thomas, et. al., Light-Emitting Carbazole Derivatives: Potential Electroluminescent Materials, J. Am. Chem. Soc. 123:9404-9411 (2001).
Toste, et al., A Versatile Procedure for the Preparation of Aryl Thiocyanates Using N-Thiocyanatosuccinimide (NTS), Synth. Comm. 25(8):1277-1286 (1995).

(56) References Cited

OTHER PUBLICATIONS

Toy, et al., "Enhanced ovarian cancer tumorigenesis and metastasis by the mecrophage colony-stimulating factor," Neoplasia, (2009), 11(2):136-144.
Toyota, et al., Expression of c-kit and kit Ligand in Human Colon Carcinoma Cells, 1993, Turn Biol 14:295-302.
Trupp, et al., Functional Receptor for GDNF Encoded by the c-ret Proto-Oncogene, Nature 381:785-789 (1996).
Tsuda, et al., "Microglia and Intractable Chronic Pain," GLIA, (2012), pp. 1-7.
Tsujimura, et al., Substitution of an Aspartic Acid Results in Constitutive Activation of c-kit Receptor Tyrosine Kinase in a Rat Tumor Mast Cell Line RBL-2H3, 1995, Int. Arch. Aller. Immunol 106:377-385.
Tsujimura, et al.,Ligand-Independent Activation of c-kit Receptor Tyrosine Kinase in a Murine Mastocytoma Cell Line P-815 Generated by a Point Mutation, Blood 9:2619-2626 (1994).
Tsujimura, Role of c-kit Receptor Tyrosine Kinase in the Development, Survival and Neoplastic Transformation of Mast Cells, Pathol Int 46:933-938 (1996).
Turner, et al., Nonhematopoeietic Tumor Cell Lines Express Stem Cell Factor and Display c-kit Receptors, 1992, Blood 80:374-381.
Uemura, et al., "The Selective M-CSF Receptor Tyrosine Kinase Inhibitor Ki20227 Suppresses Experimental Autoimmune Encephalomyelitis," J. Neuroimmunology, (2008), 195:73-80.
Undenfriend, et al., Scintillation Proximity Assay: A Sensitive and Continuous Isotopic Method for Monitoring Ligand/Receptor and Antigen/Antibody Interactions, Anal. Biochem., 161:494-500 (1987).
Uritskaya, et al., STN Accession No. 1974-27133; Document No. 08:27133; Abstract of Khimiya Geterotsiklicheskikh Soedinenii (1973, (10), 1370-3).
Uritskaya, et al., STN Accession No. 1974-27133; Document No. 08:27133; Abstract of Khimiya Geterotsiklicheskikh Soedinenii (1973), 10:1370-1373.
US Final Office Action dated Jun. 29, 2012 in U.S. Appl. No. 12/616,079.
US Notice of Allowance dated Oct. 25, 2012 U.S. Appl. No. 12/616,079.
US Notice of Allowance dated Jul. 27, 2010 in U.S. Appl. No. 11/435,381.
US Notice of Allowance dated Aug. 11, 2010 in U.S. Appl. No. 11/960,590.
US Notice of Allowance dated Aug. 13, 2010 in U.S. Appl. No. 11/962,044.
US Notice of Allowance dated Aug. 6, 2010 in U.S. Appl. No. 11/986,667.
US Notice of Allowance dated Dec. 8, 2011 in U.S. Appl. No. 13/216,200.
US Notice of Allowance dated May 17, 2012 in U.S. Appl. No. 11/961,901.
US Notice of Allowance dated May 27, 2010 in U.S. Appl. No. 11/435,381.
US Office Action dated Jan. 4, 2008 for U.S. Appl. No. 11/154,988.
US Office Action dated Jun. 6, 2007 for U.S. Appl. No. 11/016,350.
US Office Action dated Aug. 22, 2007 for U.S. Appl. No. 11/487,134.
US Office Action dated Sep. 22, 2009 for U.S. Appl. No. 11/986,667.
US Office Action dated Sep. 23, 2009 for U.S. Appl. No. 11/962,044.
US Office Action dated Oct. 17, 2012 in U.S. Appl. No. 12/906,980.
US Office Action dated Oct. 19, 2007 for U.S. Appl. No. 11/154,988.
US Office Action dated Oct. 26, 2007 for U.S. Appl. No. 11/016,350.
US Office Action dated Nov. 14, 2012 in U.S. Appl. No. 12/958,379.
US Office Action dated Feb. 17, 2010 in U.S. Appl. No. 11/962,044.
US Office Action dated Jul. 22, 2010 in U.S. Appl. No. 12/244,730.
US Office Action dated Aug. 2, 2007 in U.S. Appl. No. 11/016,350.
US Office Action dated Feb. 19, 2010 in U.S. Appl. No. 11/435,381.
US Office Action dated Feb. 26, 2010 in U.S. Appl. No. 11/986,667.
US Office Action dated Feb. 29, 2012 in related U.S. Appl. No. 12/906,980.
US Office Action dated Feb. 9, 2012 in U.S. Appl. No. 12/616,079.
US Office Action dated Jun. 1, 2009 for U.S. Appl. No. 11/435,381.
US Office Action dated Mar. 4, 2009 for U.S. Appl. No. 11/435,381.
US Office Action dated May 15, 2008 in U.S. Appl. No. 11/487,134.
US Office Action Dec. 18, 2009 for U.S. Appl. No. 11/473,347.
Vachon, et al., "The influence of microencapsulation using Eudragit RS100 on the hydrolysis kinetics of acetylsalicylic acid," J. Microencapsulation, (1997), 14(3):281-301.
Valent, Biology, Classification and Treatment of Human Mastocytosis, Wein/Klin Wochenschr 108:385-397 (1996).
Van Heyningen, One Gene—Four Syndromes, Nature 367:319-320 (1994).
Van Regenmortel, Use of biosensors to characterize recombinant proteins, (1994), Developments in Biological Standardization, 83:143-51.
Vandelli, et al., Analysis of release data in the evaluation of the physical state of progesterone in matrix systems. J. Microencapsulation, 10:1, 55-65, 1993.
Variankaval, et al., "From form to function: crystallization of active pharmaceutical ingredients," AIChE Journal, (2008), 54(7):1682-1688.
Vely, et al., BIAcore® analysis to test phosphopeptide-SH2 domain interactions, (2000), Methods in Molecular Biology, 121:313-21.
Verfaillie, Chronic myelogenous leukemia: too much or too little growth, or both?; Leukemia, 1998, 12:136-138.
Viskochil, It Takes Two to Tango: Mast Cell and Schwann Cell Interactions in Neurofibromas, J Clin Invest., 112:1791-1793 (2003).
Vliagoftis, et al., The protooncogene c-kit and c-kit ligand in human disease, Journ. Clin. Immunol, 100:435-440 (1997).
Wakefield, Basil "Fluorinated Pharmaceuticals" Innovations in Pharmaceutical Technology, (2003), 74:76-78. Online "http://web.archive/org/web/20030905122408/http://www.iptonline.com/articles/public/IPTFOUR74NP.pdf." (accessed via Wayback machine Nov. 20, 2009 showing web availability as of Sep. 2003).
Waldo, et al., "Heterogeneity of human macrophages in culture and in atherosclerotic plaques," Am. J. of Pathology, (2008), 172(4):1112-1126.
Weber, Physical Principles of Protein Crystallization, Adv. Protein Chem., 41:1-36 (1991).
Wells, et al, Targeting the RET Pathway in Thyroid Cancer, Clin Cancer Res, (2009), 15(23):7119-7123.
Wendt, et al, Identification of novel binding interactions in the development of potent, selective 2-naphthamidine inhibitors of urokinase, synthesis, structural analysis, and SAR of y-Phenyl amide 6-substitution. J. Med. Chem., 47(2):303 (2004).
Wentworth, et al., "Pro-Inflammatory $CD11C^+CD206^+$ Adipose Tissue Macrophages Are Associated With Insulin Resistance in Human Obesity," Diabetes, (2010), 59:1648-1656.
Werness, et al., Association of Human Papillomavirus Types 16 and 18 E6 Proteins with p53, Science 248:76-79 (1990).
Wessjohann, Synthesis of Natural-Product-Based Compound Libraries, Curr Opin Chem Biol., 4:303-309 (2000).
Wharam, et al., Specific Detection of DNA and RNA Targets Using a Novel Isothermal Nucleic Acid Amplification Assay Based on the Formation of a Three-Way Junction Structure, Nucleic Acids Res., 29:1-8 (2001).
Wild, et al, Antibodies to Nerve Growth Factor Reverse Established Tactile Allodynia in Rodent Models of Neuropathic Pain without Tolerance, J. Pharmacol. Exp. Ther. 322:282-287 (2007).
Williams, et al., Dissection of the Extracellular Human Interferon y Receptor a-Chain into two Immunoglobulin-like domains. Production in an *Escherichia coli* Thioredoxin Gene Fusion Expression system and Recognition by Neutralizing Antibodies, (1995) Biochemistry 34:1787-1797.
Willmore-Payne, et al. Humon Pathology, (2005) 36:486-493.
Wolff, "Burger's Medicinal Chemistry, 5ed, Part 1", John Wiley & Sons, (1995), 975-977.

(56) References Cited

OTHER PUBLICATIONS

Woon, et al., Construction and Characterization of a 10-Fold Genome Equivalent Rat P1-Derived Artificial Chromosome Library, Genomics, 50:306-316 (1998).

Wright, et al., The STE20 Kinase KGK Is Broadly Expressed in Human tumor Cells and Can Modulate Cellular Transformation, Invasion, and Adhesion, Mol. Cell. Biol. 23:2068-2082 (2003).

Wuthrich, Chapter 10: Three-Dimensional Protein Structures by NMR, NMR of Proteins and Nucleic Acids, 10:176-199 (1986).

Wyckoff, et al., Direct visualization of macrophage-assisted tumor cell intravasation in mammary tumors. Cancer Research, 67(6): 2649-2656, 2007.

Xing, "BRAF mutation in thyroid cancer," Endocrine-Related Cancer, (2005), 12:245-262.

Xing, et al., "BRAF Mutation Predicts a Poorer Clinical Prognosis for Papillary Thyroid Cancer," J. Clin. Endocrinol. Metab., (2005), 90(12):6373-6379.

Xu, et al, Modulation of Endothelial Cell function by Normal Polyspecific Human Intraveneous immunoglobulins, Am. J. Path. 153:1257-1266 (1998).

Xu, et al., "CSF1R signaling blockade stanches tumor-infiltrating myeloid cells and improves the efficacy of radiotherapy in prostate cancer," Cancer Res., (2013), 73(9):2782-2794.

Yakhontov, et al., Derivatives of 7-azaindole. XV. Electrophilic substitution of 4-methyl-7-azaindole and its derivatives, Zhurnal Obshchei Khimii (1965), 1(11): 2032-2040. (English abstract only).

Yamaguchi, et al., "Calcium Restriction Allows cAMP Activation of the B-Raf/ERK Pathway, Switching Cells to a cAMP-dependent Growth-stimulated Phenotype," The Journal of Biological Chemistry, (2004), 279:40419-40430.

Yamaguchi, et al., "Cyclic AMP activates B-Raf and ERK in cyst epithelial cells from autosomal-dominant polycystic kidneys," Kidney International, (2003), 63:1983-1994.

Yang et. al., Synthesis of some 5-substituted indoles. Heterocycles, 34:1169 (1992).

Yang, et al, Identification of Brain-Derived Neurotrophic Factor as a Novel Functional Protein in Hepatocellular Carcinoma, Cancer Res. 65:219-225 (2005).

Yang, et al., Neurofibromin-Deficient Schwann Cells Secrete a Potent Migratory Stimulus for NF1+/− Mast Cells, J Clin Invest., 112:1851-1861 (2003).

Yang, et al., Nf1-Dependent tumors require a microenvironment containing Nf1+/__ -and c-kit-Dependent bone marrow, Cell, 135:437-448, 2008.

Yao, et al., A Novel Human STE20-related Protein Kinase, HGK, That Specifically Activates the c-Jun N-terminal Kinase Signaling Pathway, J. Biol. Chem. 274:2118-2125 (1999).

Yee, et al., Role of kit-Ligand in Proliferation and Suppression of Apoptosis in Mast Cells: Basis for Radiosensitivity of White Spotting and Steel Mutant Mice, J. Exp. Med., 179:1777-1787 (1994).

Yeung, et al., Friedel-Crafts acylation of indoles in acidic imidazolium chloroaluminate ionic liquid at room temperature, Tetrahedron Letters, (2002), 43(33), 5793-5795.

Yoshida, et al., "Studies on anti-helicobacter pylori agents, Part 1: Benzyloxyisoquinoline derivatives," Bioorganic & Medicinal Chemistry, Elsevier Science Ltd, (1999), 7(11):2647-2666.

Yuan, et al., Human Peripheral Blood Eosinophils Express a Functional c-kit Receptor for Stem Cell Factor that Stimulates Very Late Antigen 4 (VLA-4)-Mediated Cell Adhesion to Fibronectin and Vascular Cell Adhesion Molecule 1 (VCAM-1), J. Exp. Med. 186:313-323 (1997).

Zaidi, et al., "Interferon-γ links ultraviolet radiation to melanomagenesis in mice." Nature, (2011), 469:548-553.

Zanon, et. al., Copper-Catalyzed Domino Halide Exchange-Cyanation of Aryl Bromides, J. Am. Chem. Soc. 125:2890-2891 (2003).

Zhang, et al., "Design and pharmacology of a highly specific dual FMS and KIT kinase inhibitor," Proc. Natl. Acad. Sci., (2013), 110(14):5689-5694.

Zhang, et al., An effective procedure for the acylation of azaindoles at C-3, Journal of Organic Chemistry (2002), 67(17): 6226-6227 and p. S1-S30.

COMPOSITIONS AND USES THEREOF

CROSS-REFERENCE TO RELATED APPLICATIONS

This application is a divisional of U.S. application Ser. No. 12/752,035, filed Mar. 31, 2010, which claims the benefit under 35 U.S.C. §119(e) of U.S. Provisional Applications No. 61/166,677, filed Apr. 3, 2009, and No. 61/176, 051, filed on May 6, 2009, and under 35 U.S.C. §119(a)-(d) of European Patent Application 09175665.0, filed on Nov. 11, 2009.

FIELD OF THE INVENTION

Disclosed are compositions that include compounds, such as biologically active compounds, and methods of making such compositions.

BACKGROUND OF THE INVENTION

PCT Application Publication Number WO 2007/002325 discloses propane-1-sulfonic acid {3-[5-(4-chloro-phenyl)-1H-pyrrolo[2,3-b]pyridine-3-carbonyl]-2,4-difluoro-phenyl}-amide (see e.g., page 80 and corresponding formula on page 82).

SUMMARY OF THE INVENTION

The present inventions provide compositions that include or relate to Compound I. "Compound I" as used herein means propane-1-sulfonic acid {3-[5-(4-chloro-phenyl)-1H-pyrrolo[2,3-b]pyridine-3-carbonyl]-2,4-difluoro-phenyl}-amide (the compound has also been referred to using the nomenclature "propane-1-sulfonic acid {3-[5-(4-chlorophenyl)-1H-pyrrolo [2,3-b] pyridine-3-carbonyl-2,4-difluoro-phenyl]-amide}"), salts of such compound (including pharmaceutically acceptable salts), conjugates of such compound, derivatives of such compound, forms of such compound, and prodrugs of such compound. The structure of propane-1-sulfonic acid {3-[5-(4-chloro-phenyl)-1H-pyrrolo[2,3-b]pyridine-3-carbonyl]-2,4-difluoro-phenyl}-amide is shown below.

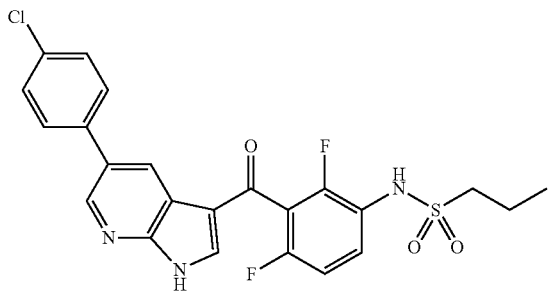 [SMILES: CCCS(=O)(=O)Nc1ccc(F)c(C(=O)c2c[nH]c3ncc(-c4ccc(Cl)cc4)cc23)c1F]

propane-1-sulfonic acid {3-[5-(4-chloro-phenyl)-1H-pyrrolo[2,3-b]pyridine-3-carbonyl]-2,4-difluoro-phenyl}-amide As used herein, the term "solid dispersion" means any solid composition having at least two components. In certain embodiments, a solid dispersion as disclosed herein includes an active ingredient (for example Compound 1); preferably dispersed among at least one other component, for example a polymer. In certain embodiments, a solid dispersion as disclosed herein is a pharmaceutical dispersion that includes at least one pharmaceutically or biologically active ingredient (for example Compound 1). In some embodiments, a solid dispersion includes Compound I molecularly dispersed with a polymer. Preferably the solid dispersion exists as a one phase system. An especially preferred solid dispersion according to the present invention is microprecipitated bulk powder (MBP) comprising Compound I.

The term "molecularly dispersed", as used herein, refers to the random distribution of a compound (e.g., Compound I) with a polymer. In certain embodiments the compound is present in the polymer in a final state of subdivision. See, e.g., M. G. Vachon et al., *J. Microencapsulation*, 14:281-301 (1997) and Vandelli et al., *J. Microencapsulation*, 10: 55-65 (1993). In some embodiments, a compound (for example, Compound I) may be dispersed within a matrix formed by the polymer in its solid state such that the compound is immobilized in its amorphous form. Whether a compound is molecularly dispersed in a polymer may be evidenced in a variety of ways, e.g., by the resulting solid molecular complex having a single glass transition temperature.

The term "solid molecular complex" as used herein means a solid dispersion that includes Compound I molecularly dispersed within a polymer matrix.

The term "immobilize", as used herein with reference to the immobilization of the active compound in the polymer matrix, means that molecules of the compound interact with molecules of the polymer in such a way that the molecules of the compound are held in the aforementioned matrix and prevented from crystal nucleation due to lack of mobility. In some embodiments the polymer may prevent intermolecular hydrogen bonding or weak dispersion forces between two or more drug molecules of Compound I. See, for example, Matsumoro and Zografi, Pharmaceutical Research, Vo. 16, No. 11, p 1722-1728, 1999.

Accordingly, in a first aspect, provided is a solid dispersion that includes Compound I and a polymer. Also provided is a solid molecular complex that includes Compound I and a polymer. The polymer may be a non-ionic polymer or an ionic polymer. In certain embodiments, the polymer is selected from the group consisting of hydroxypropylmethyl cellulose acetate succinate, hydroxypropylmethyl cellulose, methacrylic acid copolymers, and the like, as well as mixtures of any two or more thereof. In some embodiments the ratio of the amount by weight of Compound I within the solid dispersion or solid molecular complex to the amount by weight of the ionic polymer therein is from about 1:9 to about 5:5. In a preferred embodiment of the invention, the ratio of the amount by weight of Compound I within the solid dispersion or solid molecular complex to the amount by weight of the ionic polymer therein is from about 2:8 to about 4:6. In various embodiments the ratio of Compound I to the polymer in the solid dispersion is not 1:1; for example the ratio may be about 2:8; or about 3:7; or about 4:6. In a preferred embodiment, the ratio of the amount by weight of Compound I within the solid dispersion or solid molecular complex to the amount by weight of the ionic polymer therein is about 3:7. In certain preferred embodiments Compound I may be present in the solid dispersion in an amount of from about 0.1% to about 80%, by weight, of the solid dispersion; or in amount of from about 10% to about 70%, by weight, of the solid dispersion; or in an amount of from about 20% to about 60%, by weight, of the solid dispersion; or in an amount of from about 20% to about 40%, by weight, of the solid dispersion; or in an amount of about 30%, by weight, of the solid dispersion. In certain embodiments of the solid dispersions, the polymer may be present in the solid dispersion in an amount of not less than about 20%, by weight, of the solid dispersion; or in an amount of from about 20% to about 95% by weight of the solid dispersion; or in an amount of from about 20% to about 70% by weight of the solid dispersion.

In certain preferred embodiments Compound I is stable in the solid dispersion (or solid molecular complex) for at least 2 months at 25° C.; or for at least 6 months at 25° C.; or for at least 12 months at 25° C.; or for at least 15 months at 25° C.; or for at least 18 months at 25° C.; or for at least 24 months at 25° C.; or for at least 2 months at 40° C. and 75% relative humidity; or for at least 4 months at 40° C. and 75% relative humidity; or for at least 5 months at 40° C. and 75% relative humidity; or for at least 6 months at 40° C. and 75% relative humidity. In certain preferred embodiments, Compound I is immobilized so that it is primarily in amorphous form within the solid dispersion or solid molecular complex for at least three weeks of storage at 40° C. and 75% relative humidity; or for at least one month of storage at 40° C. and 75% relative humidity; or for at least two months of storage at 40° C. and 75% relative humidity; or for at least three months of storage at 40° C. and 75% relative humidity; or for at least four months of storage at 40° C. and 75% relative humidity; or for at least five months of storage at 40° C. and 75% relative humidity; or for at least six months of storage at 40° C. and 75% relative humidity.

In some embodiments, Compound I is present in the complex as a tosylate salt; or as a mesylate salt. The complex may further include a pharmaceutically acceptable carrier.

As used herein, the term "primarily in amorphous form" means that greater than 50%; or greater than 55%; or greater than 60%; or greater than 65%; or greater than 70%; or greater than 75%; or greater than 80%; or greater than 85%; or greater than 90%; or greater than 95% of the compound present in a composition is in amorphous form.

As used herein, the term "about" used in the context of quantitative measurements means the indicated amount±10%. For example, "about 2:8" would mean 1.8-2.2:7.2-8.8.

As used herein in the context of a pharmaceutically or biologically active compound (for example Compound I), the term "stable" refers to the ability of the compound to retain its activity or to retain certain physical or chemical properties under certain specified conditions. In some embodiments, an active compound is "stable" if the activity at the end of the specified period is at least 50%; or at least 60%; or at least 70%; or at least 75%; or at least 80%; or at least 85%; or at least 90%; or at least 95%; or at least 98% of the activity of the compound at the beginning of the specified period. In some embodiments, a compound in an amorphous form is stable if at least 50%; or at least 60%; or at least 70%; or at least 75%; or at least 80%; or at least 85%; or at least 90%; or at least 95%; or at least 98% of the compound remains in the amorphous form at the end of the specified period. In further embodiments, an amorphous compound is stable if it does not form any detectable crystalline peaks in powder XRD profiles during the indicated period.

The term "methacrylic acid copolymers" as used herein includes methacrylic acid copolymers, methacrylic acid— methacrylate copolymers, methacrylic acid—ethyl acrylate copolymers, ammonium methacrylate copolymers, aminoalkyl methacrylate copolymers and the like. In certain embodiments, a "methacrylic acid copolymer" may be EUDRAGIT® L 100 and EUDRAGIT® L 12,5 (also referred to as, or conforms with: "Methacrylic Acid Copolymer, Type A;" "Methacrylic Acid—Methyl Methacrylate Copolymer (1:1);" "Methacrylic Acid Copolymer L;" "DMF 1242" or "PR-MF 6918"); EUDRAGIT® S 100 and EUDRAGIT® S 12,5 (also referred to as, or conforms with: "Methacrylic Acid Copolymer, Type B;" "Methacrylic Acid—Methyl Methacrylate Copolymer (1:2);" "Methacrylic Acid Copolymer S;" "DMF 1242" or "PR-MF 6918"); EUDRAGIT® L 100-55 (also referred to as, or conforms with: "Methacrylic Acid Copolymer, Type C;" "Methacrylic Acid-Ethyl Acrylate Copolymer (1:1) Type A;" "Dried Methacrylic Acid Copolymer LD;" or "DMF 2584"); EUDRAGIT® L 30 D-55 (also referred to as, or conforms with: "Methacrylic Acid Copolymer Dispersion;" "Methacrylic Acid—Ethyl Acrylate Copolymer (1:1) Dispersion 30 Percent;" "Methacrylic Acid Copolymer LD;" JPE DMF 2584; PR-MF 8216); EUDRAGIT® FS 30 D (also referred to as DMF 13941 or DMF 2006-176); EUDRAGIT® RL 100 (also referred to as, or conforms with: "Ammonio Methacrylate Copolymer, Type A;" "Ammonio Methacrylate Copolymer (Type A);" "Aminoalkyl Methacrylate Copolymer RS;" "DMF 1242" or "PR-MF 6918"); EUDRAGIT® RL PO (also referred to as, or conforms with: "Ammonio Methacrylate Copolymer, Type A;" "Ammonio Methacrylate Copolymer (Type A);" "Aminoalkyl Methacrylate Copolymer RS;" "DMF 1242"); EUDRAGIT® RL 12,5 (also referred to as, or conforms with "Ammonio Methacrylate Copolymer, Type A;" "Ammonio Methacrylate Copolymer (Type A);" "DMF 1242" or "PR-MF 6918"); EUDRAGIT® L 100-55 (also referred to as, or conforms with: "Methacrylic Acid Copolymer, Type C;" "Methacrylic Acid—Ethyl Acrylate Copolymer (1:1) Type A;" "Dried Methacrylic Acid Copolymer LD;" "DMF 2584"); EUDRAGIT® L 30 D-55 (also referred to as, or conforms with: "Methacrylic Acid Copolymer Dispersion" NF "Methacrylic Acid—Ethyl Acrylate Copolymer (1:1) Dispersion 30 Percent;" "Methacrylic Acid Copolymer LD;" "DMF 2584" or "PR-MF 8216"); EUDRAGIT® FS 30 D (also referred to as, or conforms with: "DMF 13941" or "DMF 2006-176"); EUDRAGIT® RL 100 (also referred to as, or conforms with: "Ammonio Methacrylate Copolymer, Type A;" "Ammonio Methacrylate Copolymer (Type A);" "Aminoalkyl Methacrylate Copolymer RS;" "DMF 1242;" or "PR-MF 6918"); EUDRAGIT® RL PO (also referred to as, or conforms with: "Ammonio Methacrylate Copolymer, Type A;" "Ammonio Methacrylate Copolymer (Type A);" "Aminoalkyl Methacrylate Copolymer RS;" or "DMF 1242"); EUDRAGIT® RL 12,5 (also referred to as, or conforms with: polymer conforms to "Ammonio Methacrylate Copolymer, Type A;" "Ammonio Methacrylate Copolymer (Type A);" "DMF 1242" or "PR-MF 6918"); EUDRAGIT® RL 30 D (also referred to as, or conforms with: "Ammonio Methacrylate Copolymer Dispersion, Type A;" "Ammonio Methacrylate Copolymer (Type A);" or "DMF 1242"); EUDRAGIT® RS 100 (also referred to as, or conforms with: "Ammonio Methacrylate Copolymer, Type B;" NF "Ammonio Methacrylate Copolymer (Type B);" "Aminoalkyl Methacrylate Copolymer RS;" "DMF 1242" or "PR-MF 6918"); EUDRAGIT® RS PO (also referred to as, or conforms with: "Ammonio Methacrylate Copolymer, Type B;" "Ammonio Methacrylate Copolymer (Type B);" "Aminoalkyl Methacrylate Copolymer RS;" or "DMF 1242"); EUDRAGIT® RS 12,5 (also referred to as, or conforms with: "Ammonio Methacrylate Copolymer, Type B;" NF polymer conforms to "Ammonio Methacrylate Copolymer (Type B);" "DMF 1242" or "PR-MF 6918"); EUDRAGIT® RS 30 D (also referred to as, or conforms with: "Ammonio Methacrylate Copolymer Dispersion, Type B;" NF polymer conforms to "Ammonio Methacrylate Copolymer (Type B);" or "DMF 1242"); EUDRAGIT® E 100 (also referred to as, or conforms with: "Amino Methacrylate Copolymer;" NF "Basic Butylated Methacrylate Copolymer;" "Aminoalkyl Methacrylate Copolymer E;" "DMF 1242" or "PR-MF 6918"); EUDRAGIT® E PO (also referred to as, or conforms with: "Basic Butylated Methacrylate Copolymer;" "Aminoalkyl Methacrylate Copolymer E;" "Amino Methacrylate Copolymer;" "DMF 1242"); EUDRAGIT® E 12,5 (also referred to as, or conforms with: "Amino Methacrylate Copolymer;" "Basic Butylated Methacrylate Copolymer;" "DMF 1242" or "PR-MF 6918"); EUDRAGIT®NE 30 D (also referred to as, or conforms with: "Ethyl Acrylate and Methyl Methacrylate Copolymer Dispersion;" "Polyacrylate Dispersion 30 Percent;" ("Poly(ethylacrylat-methylmethacrylat)-Dispersion 30%"); "Ethyl Acrylate Methyl Methacrylate Copolymer Dispersion;" "DMF 2822" or "PR-MF 6918"); EUDRAGIT® NE 40 D (also referred to as, or conforms with: DMF 2822); EUDRAGIT® NM 30 D (also referred to as "Polyacrylate Dispersion 30 Percent;" "(Poly(ethylacrylat-methylmethacrylat)-Dispersion 30%);" or "DMF 2822"; PLASTOID® B (also referred to as, or conforms with: "DMF 12102"), or the like.

In a second aspect, provided are methods of making solid dispersions or solid molecular complexes as disclosed herein. The method may involve using Compound I in the form of a tosylate or mesylate salt.

In a third aspect, provided is a crystalline polymorph Form 1 of Compound I. In certain embodiments the crystalline polymorph Form 1 of Compound I exhibits a powder x-ray diffraction pattern having characteristic peak locations of approximately 4.7, 9.4, 11.0, 12.5, and 15.4 degrees 2θ; or having characteristic peak locations of approximately 4.7, 9.4, 10.0, 11.0, 12.5, 14.2, 15.4, 18.6, and 22.2 degrees 2θ; or having characteristic peak locations of approximately 4.7, 9.4, 10.0, 11.0, 12.5, 14.2, 15.4, 16.1, 18.6, 19.0, 22.2 and 26.8 degrees 2θ. In certain embodiments the crystalline polymorph Form 1 of Compound I exhibits a powder x-ray diffraction pattern substantially the same as the powder x-ray diffraction pattern of FIG. 1. Also provided are methods of preparing solid dispersions and solid molecular complexes as described herein wherein the solid dispersion or solid molecular complex is prepared from Compound I in the form of crystalline polymorph Form 1.

In a fourth aspect, provided is a crystalline polymorph Form 2 of Compound I. In certain embodiments the crystalline polymorph Form 2 of Compound I exhibits a powder x-ray diffraction pattern having characteristic peak locations of approximately 8.8, 9.2, 13.5, 19.1 and 24.4 degrees 2θ; or having characteristic peak locations of approximately 6.7, 8.8, 9.2, 13.5, 15.0, 17.7, 19.1, 19.7, 21.4 and 24.4 degrees 2θ; or having characteristic peak locations of approximately 6.7, 8.8, 9.2, 13.5, 14.1, 14.5, 15.0, 16.2, 17.0, 17.7, 19.1, 19.7, 21.4, 22.2, 24.1, 24.4, and 28.1 degrees 2θ. In certain embodiments the crystalline polymorph Form 2 of Compound I exhibits a powder x-ray diffraction pattern substantially the same as the powder x-ray diffraction pattern of FIG. 2. Also provided are methods of preparing solid dispersions and solid molecular complexes as described herein wherein the solid dispersion or solid molecular complex is prepared from Compound I in the form of crystalline polymorph Form 2.

All atoms within the compound described herein are intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^{11}C$, $^{12}C$, $^{13}C$, $^{14}C$; oxygen includes for example 160, 170, 180; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

As used herein, the term "solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein, the term "substantially crystalline" material embraces material which has greater than about 90% crystallinity; and "crystalline" material embraces material which has greater than about 98% crystallinity.

As used herein, the term "substantially amorphous" material embraces material which has no more than about 10% crystallinity; and "amorphous" material embraces material which has no more than about 2% crystallinity.

As used herein, the term "semi-crystalline" material embraces material which is greater than 10% crystallinity, but no greater than 90% crystallinity; preferably "semi-crystalline" material embraces material which is greater than 20% crystallinity, but no greater than 80% crystallinity. In one aspect of the present invention, a mixture of solid forms of a compound may be prepared, for example, a mixture of amorphous and crystalline solid forms, e.g. to provide a "semi-crystalline" solid form. Such a "semi-crystalline" solid form may be prepared by methods known in the art, for example by mixing an amorphous solid form with a crystalline solid form in the desired ratio. In some instances, a compound mixed with acid or base forms an amorphous complex; a semi-crystalline solid can be prepared employing an amount of compound component in excess of the stoichiometry of the compound and acid or base in the amorphous complex, thereby resulting in an amount of the amorphous complex that is based on the stoichiometry thereof, with excess compound in a crystalline form. The amount of excess compound used in the preparation of the complex can be adjusted to provide the desired ratio of amorphous complex to crystalline compound in the resulting mixture of solid forms. For example, where the amorphous complex of acid or base and compound has a 1:1 stoichiometry, preparing said complex with a 2:1 mole ratio of compound to acid or base will result in a solid form of 50% amorphous complex and 50% crystalline compound. Such a mixture of solid forms may be beneficial as a drug product, for example, by providing an amorphous component having improved biopharmaceutical properties along with the crystalline component. The amorphous component would be more readily bioavailable while the crystalline component would have a delayed bioavailability. Such a mixture may provide both rapid and extended exposure to the active compound.

As used herein, the term "complex" refers to a combination of a pharmaceutically active compound and an additional molecular species that forms or produces a new chemical species in a solid form. In some instances, the complex may be a salt, i.e. where the additional molecular species provides an acid/base counter ion to an acid/base group of the compound resulting in an acid:base interaction that forms a typical salt. While such salt forms are typically substantially crystalline, they can also be partially crystalline, substantially amorphous, or amorphous forms. In some instances, the additional molecular species, in combination with the pharmaceutically active compound, forms a non-salt co-crystal, i.e. the compound and molecular species do not interact by way of a typical acid:base interaction, but still form a substantially crystalline structure. Co-crystals may also be formed from a salt of the compound and an additional molecular species. In some instances, the complex is a substantially amorphous complex, which may contain salt-like acid:base interactions that do not form typical salt crystals, but instead form a substantially amorphous solid, i.e. a solid whose X-ray powder diffraction pattern exhibits no sharp peaks (e.g. exhibits an amorphous halo).

As used herein, the term "stoichiometry" refers to the molar ratio of two or more reactants that combine to form a complex, for example, the molar ratio of acid or base to compound that form an amorphous complex. For example, a 1:1 mixture of acid or base with compound (i.e. 1 mole acid or base per mole of compound) resulting in an amorphous solid form has a 1:1 stoichiometry.

As used herein, the term "composition" refers to a pharmaceutical preparation suitable for administration to an intended animal subject for therapeutic purposes that contains at least one pharmaceutically active compound, including any solid form thereof. The composition may include at least one additional pharmaceutically acceptable component to provide an improved formulation of the compound, such as a suitable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. In certain embodiments, a "therapeutically-effective amount" of Compound I refers to such dosages and/or administration for such periods of time necessary to inhibit human b-Raf containing the V600E mutation. Moreover, a therapeutically effective amount may be one in which the overall therapeutically-beneficial effects outweigh the toxic or undesirable side effects. A therapeutically-effective amount of Compound I may varies according to disease state, age and weight of the subject being treated. Thus, dosage regimens are typically adjusted to the individual requirements in each particular case and are within the skill in the art. In certain embodiments, an appropriate daily dose for administration of Compound I to an adult human may be from about 100 mg to about 3200 mg; or from about 250 mg to about 2000 mg, although the upper limit may be exceeded when indicated. A daily dosage of Compound I can be administered as a single dose, in divided doses, or, for parenteral administration, it may be given as subcutaneous injection.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

Additional aspects and embodiments will be apparent from the following Detailed Description and from the claims.

DETAILED DESCRIPTION

Figure 1:
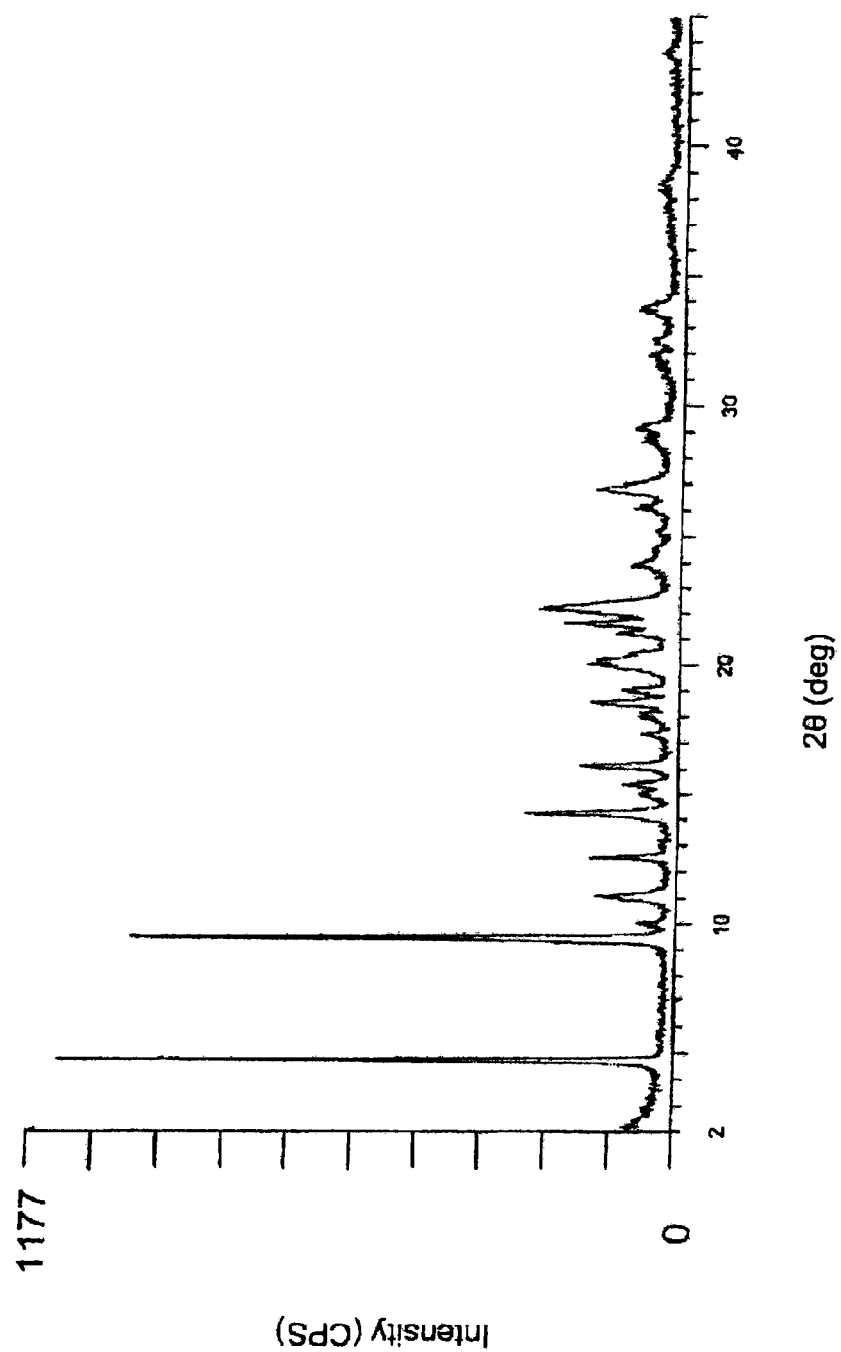
FIG. 1 is a powder x-ray diffraction pattern for the crystalline polymorph Form 1 of Compound I.

Propane-1-sulfonic acid {3-[5-(4-chloro-phenyl)-1H-pyrrolo[2,3-b]pyridine-3-carbonyl]-2,4-difluoro-phenyl}-amide, is a compound with the following structure:

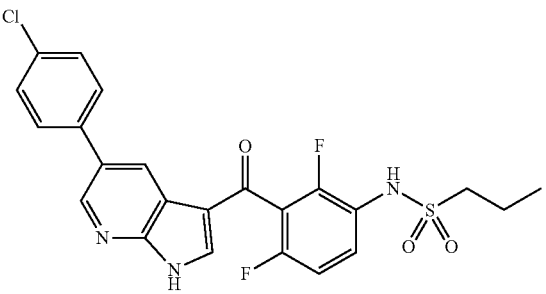 [SMILES: CCCS(=O)(=O)Nc1ccc(F)c(C(=O)c2c[nH]c3ncc(-c4ccc(Cl)cc4)cc23)c1F]

Propane-1-sulfonic acid {3-[5-(4-chloro-phenyl)-1H-pyrrolo[2,3-b]pyridine-3-carbonyl]-2,4-difluoro-phenyl}-amide (Compound I)

In some embodiments, Compound I is a b-raf kinase inhibitor. Normally functioning b-Raf is a kinase which is involved in the relay of signals from the cell membrane to the nucleus and is active only when it is needed to relay such signals. Mutant b-Raf, however, is constantly active and thus plays a role in tumor development. Mutant b-Raf containing a V600E mutation has been implicated in various tumors, for example, colorectal cancer, melanoma, and thyroid cancer. Propane-1-sulfonic acid {3-[5-(4-chloro-phenyl)-1H-pyrrolo[2,3-b]pyridine-3-carbonyl]-2,4-difluoro-phenyl}-amide specifically targets mutant b-Raf containing the V600E mutation. Accordingly, such an inhibitor is used in the inhibition of tumors, particularly solid tumors such as melanoma. As previously stated, the phrase "Compound I", as used herein, will refer to propane-1-sulfonic acid {3-[5-(4-chlorophenyl)-1H-pyrrolo [2,3-b] pyridine-3-carbonyl-2,4-difluoro-phenyl]-amide as well as any salt, conjugate, derivative, or prodrug thereof.

Compounds that have low solubility in water (for example, certain compounds in crystalline form), have a low dissolution rate and as a result can exhibit poor bioavailability. Poorly bioavailable compounds can present problems for therapeutic administration to a patient, often due to unpredictability in dose/therapy effects caused by erratic absorption of the compound by the patient. For example, the intake of food may affect the ability of the patient to absorb such poorly bioavailable compounds, thus potentially requiring dosing regimens to take into account the effect of food. In addition, when dosing, a large safety margin may be required for the dose as a result of the unpredictable dose effects. Further, due to poor bioavailability, a large dose of the compound may be required to achieve a desired therapeutic effect, thus potentially resulting in undesired side effects.

Amorphous forms of Compound I have improved solubility in water as compared to the crystalline form, but is unstable as it has a tendency to crystallize. Thus it is desired to formulate Compound I so that it may stably exist primarily in amorphous form.

Thus, in some aspects and embodiments disclosed and described herein, techniques, methods and compositions for improving the solubility and/or bioavailability of Compound I are provided. In certain embodiments, provided are compositions and methods involving Compound I in a composition, form, or formulation in which it has improved water solubility and/or bioavailability of as compared to Compound I in a crystalline form, or Compound I in a primarily crystalline form.

In some embodiments provided are compositions including Compound I in an amorphous form of the compound. The amorphous form of Compound I may have improved solubility in water as compared to Compound I in a crystalline form. In certain embodiments, formulations of Compound I in which Compound I exists stably in amorphous form may be accomplished, for example, by immobilizing the compound within a matrix formed by a polymer. See, for example, U.S. Pat. No. 6,350,786.

Solid Dispersions and Solid Molecular Complexes of Compound I and a Polymer

In some aspects and embodiments provided are solid dispersions and solid molecular complexes that include Compound I. For example, Compound I may be dispersed within a matrix formed by a polymer in its solid state such that it is immobilized in its amorphous form. In some embodiments the polymer may prevent intramolecular hydrogen bonding or weak dispersion forces between two or more drug molecules of Compound I. See, for example, Matsumoro and Zografi, Pharmaceutical Research, Vo. 16, No. 11, p 1722-1728, 1999. In certain embodiments, the solid dispersion provides for a large surface area, thus further allowing for improved dissolution and bioavailability of Compound I. In certain embodiments a solid dispersion or solid molecular complex includes a therapeutically-effective amount of Compound I.

In some embodiments of the present inventions, Compound I is present in the solid dispersion in an amount of from about 1% to about 50%, by weight; or from about 10% to about 40% by weight; or from about 20% to about 35% by weight; or from about 25% to about 30% by weight. In related embodiments, a polymer is present in the solid dispersion in an amount of from about 0% to about 50% by weight; or from about 5% to about 60% by weight; or from 10% to about 70% by weight. In certain embodiments a polymer is present in the solid dispersion in an amount greater than about 10% by weight; or greater than about 20% by weight; or greater than about 30% by weight; or greater than about 40% by weight; or greater than about 50% by weight. In one preferred embodiment, the solid dispersion is about 30% by weight Compound I and about 70% by weight polymer.

The solid dispersion may comprise Compound I dispersed in a non-ionic polymer. This may be accomplished by various means, including: (A) melting the polymer and dissolving the compound in the polymer and then cooling the mixture; and (B) dissolving both the compound of interest and the polymer in an organic solvent and evaporating the solvent in a rotary evaporator, for example. The resulting solid dispersion may comprise the compound dispersed in the polymer in amorphous form.

A solid dispersion may be formed by dispersing Compound I in an ionic polymer. Such solid dispersion may result in increased stability of Compound I. This may be accomplished by various means, including the methods described above for use in forming a dispersion in a non-ionic polymer. Because ionic polymers have pH dependent solubility in aqueous systems, the resulting solid dispersion of the Compound I and the polymer may be stable at low pH in the stomach and release the Compound I in the intestine at higher pH which is the site of absorption. In preferred embodiments, Compound I in such solid dispersions with an ionic polymer may thus be less capable of separating from the polymer and may be immobilized by the polymer in its amorphous form. Any ionic polymer may be used in the practice of the present invention. Examples of such ionic polymers include hydroxypropylmethyl cellulose acetate succinate (HPMC-AS), hydroxypropylmethyl cellulose phthalate (HPMCP), and methacrylic acid copolymers. Because one purpose of formulating Compound I in a complex with an ionic polymer is to allow for Compound I to be immobilized so that it exists primarily in amorphous form, a polymer which is capable of immobilizing Compound I so that it exists primarily in an amorphous form for an extended period of time is preferred. It has been found that polymers such as HPMC-AS and Eudragit® L 100-55 (a methacrylic acid copolymer) are capable of immobilizing Compound I so that it exists primarily in an amorphous form for at least four weeks while in storage at 40° C. and 75% relative humidity. As such, HPMC-AS and Eudragit® L 100-55 are preferred polymers for use in certain embodiments of the present invention.

HPMC-AS (HPMCAS or AQOAT™, which is available from, for example, Shin-Etsu) is a particularly preferred polymer for use in the practice of certain embodiments of the present invention. It is available in the following grades: AS-LF, AS-MF, AS-HF, AS-LG, AS-MG and AS-HG. HPMC-AS is an anionic, relatively water insoluble, high molecular weight polymer with a pH dependent water solubility, leading to dissolution at pH 5.2 and above. Said dissolution can be tailored between pH 5.2 and 6.5 according to the HPMC-AS grades used. HPMC-AS may be relatively resistant to breakdown in the acidic environment of the stomach and under normal temperatures of storage. At the same time, because HPMC-AS dissolves at pH 5.2 and above, it dissolves in the basic environment of the intestine, thus allowing for improved absorption of Compound I and further allowing for improved bioavailability of the Compound I. Accordingly, in certain embodiments of the invention, Compound I is in a solid dispersion with at least one polymer selected from HPMC-AS grades as mentioned above. It is, however, contemplated that a mixture of two or more of the various HPMC-AS grades can also be used in accordance with the present invention.

In an embodiment of the invention, the ratio of the amount by weight of Compound I within the solid complex to the amount by weight of the ionic polymer therein is from about 1:9 to about 1:1. In a preferred embodiment of the invention, the ratio of the amount by weight of Compound I within the solid complex to the amount by weight of the ionic polymer therein is from about 2:8 to about 4:6. In a preferred embodiment of the invention, the ratio of the amount by weight of Compound I within the solid complex to the amount by weight of the ionic polymer therein is about 3:7.

In an embodiment of the present invention, Compound I is immobilized so that it is primarily in amorphous form within the complex for up to three weeks of storage at 40° C. and 75% relative humidity. In a preferred embodiment, Compound I is immobilized so that it is primarily in amorphous form within the complex for up to one month of storage at 40° C. and 75% relative humidity. In another preferred embodiment, Compound I is immobilized so that it is primarily in amorphous form within the complex for up to two months of storage at 40° C. and 75% relative humidity. In another preferred embodiment, Compound I is immobilized so that it is primarily in amorphous form within the complex for up to three months of storage at 40° C. and 75% relative humidity.

In certain embodiments, HPMC-AS is present in the solid dispersion in amount of from about 1% to about 50% by weight; or from about 5% to about 60% by weight; or from 10% to about 70% by weight. In certain embodiments, HPMC-AS is present in the solid dispersion in an amount greater than about 10% by weight; or greater than about 20% by weight; or greater than about 30% by weight; or greater than about 40% by weight; or greater than about 50% by weight.

The present inventions also relate to compositions comprising a solid dispersion or solid molecular complex as disclosed herein. The composition may, in addition to the solid dispersion or solid molecular complex, also comprise therapeutically inert, inorganic or organic carriers (for example, pharmaceutically-acceptable carriers or excipients). The pharmaceutical composition may also contain additional agents such as preserving agents, solubilizing agents, stabilizing agents, wetting agents, emulsifying agents, sweetening agents, coloring agents, flavoring agents, salts for varying the osmotic pressure, buffers, coating agents and antioxidants. The composition may also contain additional therapeutically-active compounds or more than one therapeutically-active compound/polymer complex (e.g., a solid dispersion or solid molecular complex).

In certain embodiments, the composition includes the solid dispersion or solid molecular complex suspended in an aqueous vehicle containing hydroxypropylcellulose (HPC). In an especially preferred embodiment, the vehicle contains about 2% by weight HPC. In a preferred embodiment, the composition includes colloidal silicon dioxide (silica).

In certain embodiments, the addition of colloidal silicon dioxide may further improve the stability of the solid dispersion or solid molecular complex. In an especially preferred embodiment, the composition includes at least about 0.5% by weight colloidal silicon dioxide.

In certain embodiments provided compositions include Compound I (for example in a solid dispersion or solid molecular complex) and Crospovidone (or Polyplasdone XL; a disintegrating agent for the dosage form), magnesium stearate (a lubricant that may be used in tablet and capsulation operations), and/or croscarmellose sodium (AcDiSol; a disintegrating agent).

In an especially preferred embodiment, the composition comprises the solid dispersion or solid molecular complex suspended in an aqueous vehicle that is up to 2% by weight HPC and at least about 0.5% by weight colloidal silicon dioxide.

Method of Making a Solid Molecular Complex of Compound I and an Ionic Polymer

Also provided are methods of making solid molecular complexes as disclosed herein and compositions comprising the solid molecular complexes. In the method, Compound I may be microprecipitated with a polymer as disclosed herein (for example, HPMC-AS). Microprecipitation may be accomplished by any means known in the art, for example: spray drying or lyophilization; solvent-controlled precipitation; pH-controlled precipitation; hot melt extrusion; and supercritical fluid technology. Each of these methods is described in more detail below.

Once the solid dispersion precipitates out of solution using the various methods, it can be recovered from the solution by procedures known to those skilled in the art, for example by filtration, centrifugation, washing, etc. The recovered solid molecular complex can then be dried (e.g., in air, an oven, or a vacuum) and the resulting solid can be milled, pulverized or micronized to a fine powder by means known in the art. The powder form of the solid dispersion can then be dispersed in a carrier to form a pharmaceutical composition. In a preferred embodiment, at least about 0.5% w/w colloidal silicon dioxide is added to the composition.

a) Spray Drying or Lyophilization Process

Compound I and a polymer (for example, HPMC-AS) may be dissolved in a common solvent having a low boiling point, e.g., ethanol, methanol, acetone, etc. By means of spray drying or lyophilization, the solvent is evaporated by flash evaporation at a temperature close to the boiling point thereof, or under a high vacuum (low vapor pressure), leaving Compound I precipitated in a matrix formed by the polymer. In certain embodiments Compound I is in a mesylate or tosylate salt form, and thus preferably has improved solubility.

b) Solvent Controlled Precipitation

Compound I and a polymer (for example, HPMC-AS) may be dissolved in a common solvent, e.g., dimethylacetamide, dimethylformamide, dimethyl sulfoxide (DMSO), N-methyl pyrrolidone (NMP), etc. The Compound I/polymer solution is added to cold (0 to 7° C., preferably 2 to 5° C.) water adjusted to an appropriate pH (for example in many embodiments an appropriate pH is a pH of 3 or less).

This causes Compound I to microprecipitate in a matrix formed by the polymer (for example, HPMC-AS). The microprecipitate may be washed several times with aqueous medium until the residual solvent falls below an acceptable limit for that solvent. An "acceptable limit" for each solvent is determined pursuant to the International Conference on Harmonization (ICH) guidelines.

In a preferred embodiment, a solution comprising Compound I, an organic solvent (such as dimethylformamide, dimethylacetamide (DMA), dimethyl sulfoxide (DMSO), N-methyl pyrrolidone (NMP), and the like) and the ionic polymer is formed. The organic solvent is preferably DMA at 20 to 25° C. The solution may be formed by first dissolving Compound I into the organic solvent. Then, while stirring, the polymer is added. The mixture is then heated up to between about 50 to about 110° C., preferably to about 70° C.

A second solution that is 0.01 N HCl is also formed. This will herein be termed the "aqueous phase". The aqueous phase has a temperature between about 0 and about 60° C., preferably between 5 and 15° C.

The aqueous phase is then circulated through the mixing chamber of a high shear mixer while the organic phase is dosed into the chamber while the chamber is operating. Dosing may be accomplished with, for example, a gear pump, a hose pump, or a syringe pump. In a preferred embodiment, dosing is accomplished using a gear pump with an injector nozzle pointed into the mixing chamber. The mixing chamber preferably comprises a rotor and a stator. The rotor and the stator may, for example, each have either one or two rows of teeth. In a preferred embodiment, the rotor and the stator each have one row of teeth. The tip speed of the rotor is preferably set at between about 15 and about 25 m/sec.

During the mixing process, Compound I and the polymer precipitate, producing a suspension of particles of the complex of Compound I and the polymer in aqueous organic media. The suspension may then be subjected to a number of passes through a dispersing unit in order to adjust the particle size of the particles of the compound. The suspension may then be centrifuged and washed with the aqueous phase several times in order to remove the organic solvent and then washed once with pure water. The obtained product may then be delumped and dried to obtain the solid complex of the present invention. During the drying process, the temperature of the complex is preferably below 40° C. in order to avoid recrystallization of Compound I.

In certain more specific embodiments, the above method includes the following steps,
(a) dissolution of Compound I and HPMCAS in the same organic solvent to give one single organic phase;
(b) continuously adding the organic phase obtained under (a) into an aqueous phase which is present in a mixing chamber, said mixing chamber being equipped with a high shear mixing unit and two additional openings which connect said mixing chamber to a closed loop wherein said aqueous phase is circulated and passes through the mixing chamber;
(c) precipitation of a mixture consisting of the amorphous form of Compound I and HPMCAS from the aqueous phase mentioned under (b), while the high shear mixer is operating and said aqueous phase is passed through the mixing chamber in a closed loop, resulting in the formation of an aqueous suspension of the precipitate;
(d) continuously circulating the aqueous suspension through the mixing chamber while the high shear mixing unit is operating and after the organic solution prepared under (a) has been completely added to the aqueous phase until a defined particle size and/or particle size distribution is obtained;
(e) isolating the solid phase from the suspension;
(f) washing the isolated solid phase with water; and
(g) delumping and drying the solid phase.

In still more specific embodiments the present methods include the steps, wherein
the organic phase in step (a) above is a 35% solution of Compound I and HPMCAS in DMA, the ratio of Compound I to HPMCAS being 30% to 70% (w/w); and
the continuous adding in step (b) above is achieved via an injector nozzle which is oriented at an angle between 40 and 50° to the longitudinal axis of the high shear mixer and has a distance of about 1 to about 10 mm from the rotor of said high shear mixer which is operating with a tip speed of about 15 to about 25 m/sec.

In still more specific embodiments the present methods include the step, wherein
the continuous adding in step (b) above is achieved via an injector nozzle which is oriented at an angle of about 45° to the longitudinal axis of the high shear mixer and has a distance of about 2 to about 4 mm from the rotor of said high shear mixer which is operating with a tip speed of about 25 m/sec.

In other specific embodiments the present methods include the step, wherein
the drying in step (g) above is achieved via fluidized bed drying.

In a further embodiment there are provided the solid dispersions obtained by the above-mentioned method.

The dried precipitate obtained by the above method can be further processed into any type of solid pharmaceutical preparations or dosage forms, which are known to the person of skill in the art. Particularly preferred are oral dosage forms such as tablets, capsules, pills, powders, suspensions, and the like.

Consequently, so obtained pharmaceutical preparations form further embodiments provided herein.

The term "organic solvent" mentioned under step (a) above means any organic solvent wherein both Compound I and HPMCAS are miscible. Preferred organic solvents are N-Methylpyrrolidone (NMP), Dimethylformamide (DMF), Dimethylsulfoxide (DMSO), Dimethylacetamide (DMA), and the like, with DMA being the most preferred. The combined amount of Compound I and HPMCAS together in the organic phase can be within the range of about 15 to 40 weight %, preferably about 25 to 40, most preferably about 35 weight %. The weight ratio of Compound I/HPMCAS in the organic solvent is about 30/70 weight %, respectively. Preferably, the temperature of the organic solvent is adjusted between 50 and 110° C., preferably 60 and 90° C., most preferred at about 70° C. prior to its addition to the mixing chamber as mentioned under step (b). The mixture of Compound I and HPMCAS in the organic solvent is also designated herein as the "organic phase" or "DMA phase".

The term "aqueous phase" mentioned under step (b) preferably consists of acidic water (pH<7, preferably less than 3), most preferably of 0.01 N hydrochloric acid (HCl). The aqueous phase is kept at a temperature between about 0 and about 60° C., preferably between about 0 and 20° C., more preferred between about 5 and about 15° C., most preferably about 5° C. The aqueous phase circulates out of the bottom valve of its reservoir ((1) of FIG. 5) due to the stream created by the high shear mixer or with an auxiliary pump, preferably a rotary lobe pump, then passes through the high shear mixer, back into the reservoir. Preferably, the outlet of the loop is placed under the fluid level maintained in the reservoir, in order to prevent foaming.

The addition of the organic phase to the mixing chamber as mentioned in step (b) above is achieved via an injector nozzle which directly points into the aqueous phase. Any conventional nozzle known to the person of skill in the art can be used. Preferred injector nozzles show central or acentric geometry and have a diameter of about 1 to 10 mm. The acentric (not centered) geometry and a diameter of 5 mm are especially preferred. The injector nozzle may point to the rotor of the high shear mixing unit at an angle between 0 and 90°, preferably between 40 and 50°, most preferably at 450 (a, FIG. 6). During the process according to the present invention, the distance between the point of the injector nozzle and the tip of the rotor of the high shear mixing unit is about 1 to 10 mm, preferably about 2 to 4 mm and most preferably about 2.6 mm. The addition of the organic phase is preferably carried out at dosing rates of about 60/1 to about 300/1 (ratio of aqueous phase/organic phase during precipitation), preferably about 70/1 to about 120/1 and most preferably at about 100/1. Final ratio of aqueous phase/organic phase after precipitation is in the range of about 5/1-12/1 preferably 7/1-10/1 and most preferably at 8.5/1.

While the organic phase is added (injected) into the aqueous phase of the mixing chamber, the high shear mixing unit is operating. Any conventional high shear mixing unit (rotor/stator unit) known to the person of skill in the art can be applied. The preferred rotor geometry according to the present invention uses a rotor/stator unit with a radial single teeth row or double teeth row or combination thereof. The tip speed of the rotor is about 15 to about 25 m/sec., preferably 25 m/sec.

Subsequent to the complete addition of the organic phase into the aqueous phase, the obtained suspension, thus the precipitate consisting of amorphous Compound I and HPMCAS in the aqueous phase, is further circulated in the closed loop containing the high shear mixing unit. Outside of the high shear mixing unit the circulation must be carried out with the aid of an auxiliary pump, preferably a rotary lobe pump. The suspension is passed through the high shear mixing unit several times, up to the moment where a desired particle size and/or particle size distribution is obtained. Usually the suspension is passed through the high shear mixing unit about 1 to 60 times, most preferably 6 times. The particle size and/or particle size distribution can be determined by standard techniques, well known to the person of skill in the art, such as for example dynamic light scattering. The preferred particle size according to the present invention is with in the range of D50=80-230 m preferably D50=80-160 m.

Isolation of the solid dispersion (MBP) according to step (e) above can be carried out by using conventional filter techniques or centrifuges. Prior to isolation, the suspension is preferably adjusted to about 5 to 10° C. Subsequently, the isolated solid dispersion is washed with acidic water; preferably 0.01 N HCl followed by further washing with pure water in order to substantially remove the organic solvent (step (f)). The isolated (wet) solid dispersion (MBP) usually shows a water content between 60 and 70% (w/w), which is preferably dried before any further processing. The drying can be carried out using any standard techniques known to the person of skill in the art, for example using a cabinet dryer at temperatures between 30 and 50° C., preferably at about 40° C. and at reduced pressure, preferably below 20 mbar. Several drying procedures can be combined or used sequentially, whereby the use of fluidized bed drying is especially preferred as the final drying step according to the present invention.

Figure 7A:
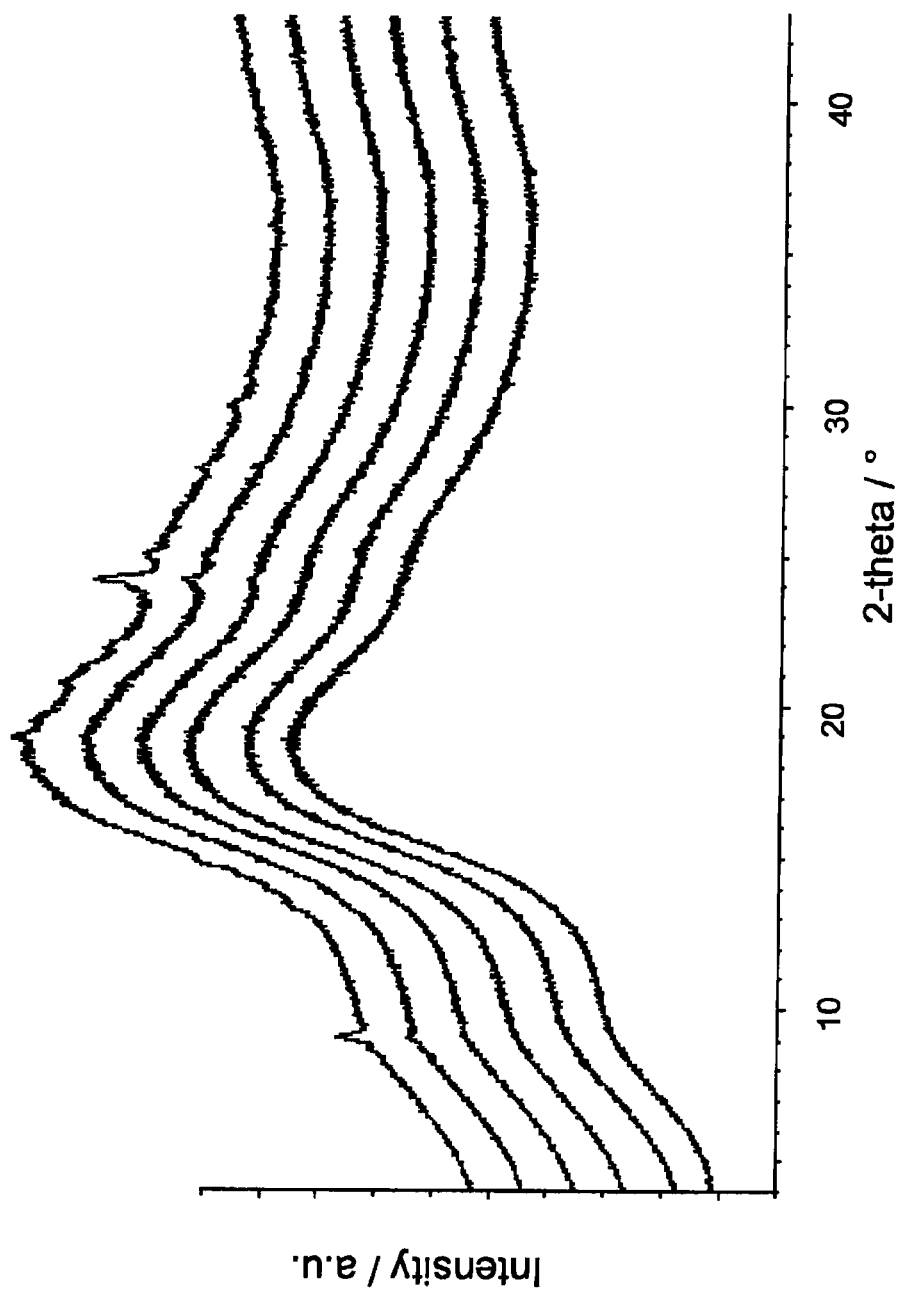
FIGS. 7A and 7B provide a comparison of X-ray patterns obtained from two lots of solid dispersions (MBP's) containing HPMCAS and Compound I, manufactured via high shear mixer precipitation according to the method disclosed in Example 22 (see FIG. 7A) and via conventional spray precipitation (see FIG. 7B).

A specific method of making the (HPMCAS-Compound I) MBP according to steps a) to g) above is described in Example 22, which forms a further preferred embodiment of the present invention. The stability of the solid dispersion (MBP) as obtained by the method of Example 22 was compared with the stability of an MBP obtained via conventional spray precipitation. "Conventional spray precipitation" means that the organic phase was sprayed onto the aqueous phase via a nozzle which is placed outside the aqueous phase, above its surface like is the case for many conventional spray-precipitation techniques. All further process parameters are the same for both methods. The stability, thus the inhibition of re-crystallization of Compound I, is determined by x-ray diffraction measurements, using a conventional wide angle X-ray scattering setup as it is well known to the skilled artisan. Sample preparation was identical for both MBP's. The samples were treated in a climate chamber (50° C. and 90% humidity (RH)) for several hours respective days (0 h, 14 h, 41 h, 4 d, 6 d, 13 d) prior to X-ray measurements. The results are shown in FIG. 7A for the MBP obtained according to Example 22, and FIG. 7B for the MBP obtained by the conventional method. The earliest X-ray curves of both MBP's show a broad halo in the wide angle region with the absence of sharp signals, thereby evidencing that both materials are in an amorphous state. Within several days, sharp signals occur in the X-ray curves obtained from the MBP manufactured by the conventional method (see FIG. 7B), but not in the X-ray curves obtained from the MBP prepared using the method disclosed herein (see FIG. 7A).

Figure 7B:
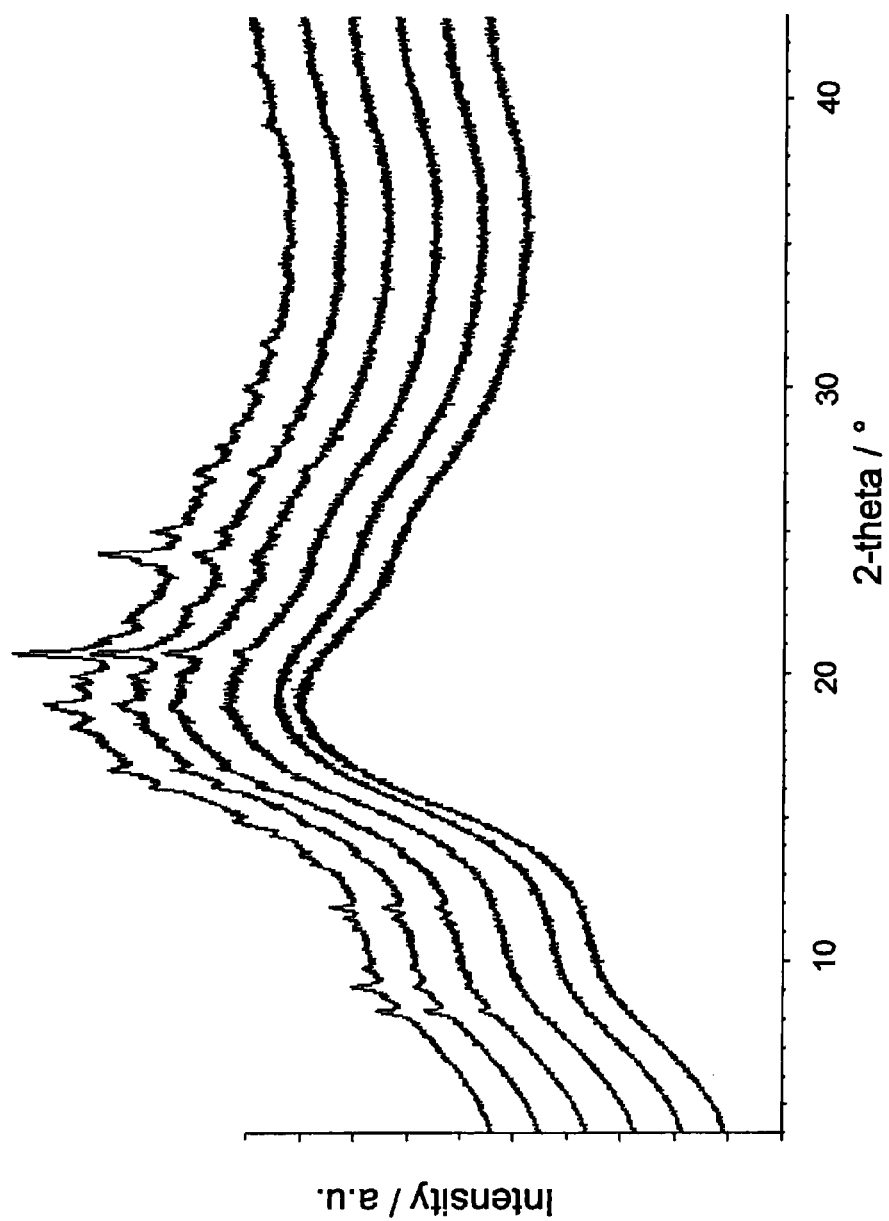

In summary, the results presented in FIGS. 7A and 7B demonstrate that the spray precipitated MBP is less stable against re-crystallization than the high shear precipitated MBP as evidenced by the early occurrence of sharp signals in the diffractograms (see FIG. 7B), which can be allocated to the crystalline form of Compound I. The bottom line in each figure represents the initial sample, the following lines bottom up after 14 h, 41 h, 96 h, 6 d respective 13 d storage in a climate controlled chamber (at 50° C. 90% RH).

Figure 5:
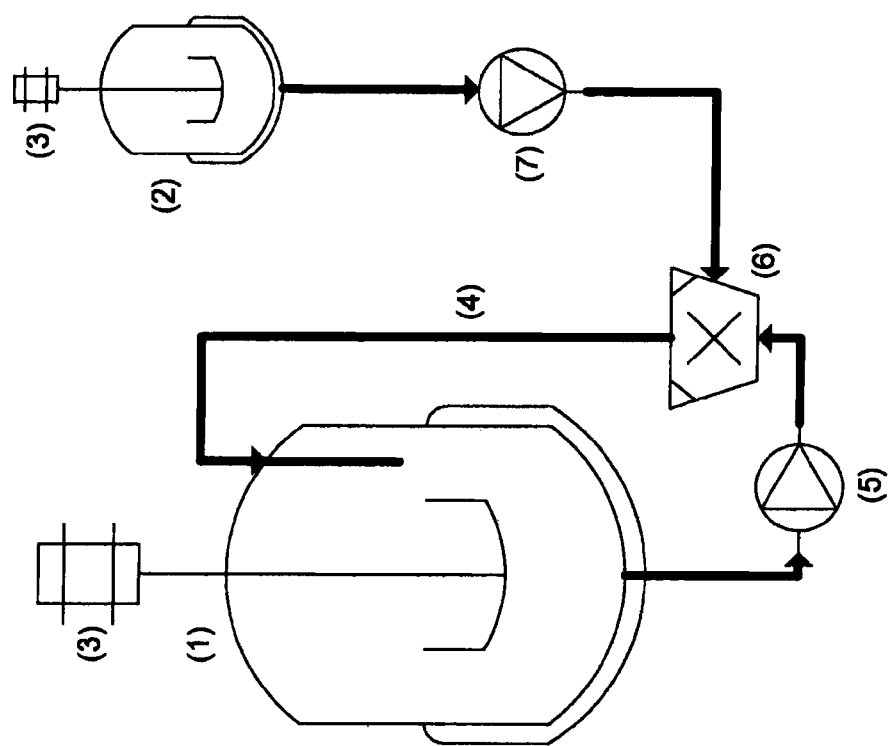
FIG. 5 is a schematic drawing of an exemplary setup for manufacturing a solid dispersion (MBP) according to steps a) to d), more specifically according to Example 22 of the present invention.

The novel processes as provided herein can preferably be carried out using a setup as shown in the accompanying FIG. 5.

A setup substantially as illustrated in FIG. 5 can be used for the following preparation. Thus, FIG. 5 contemplates two reservoirs (vessels) with temperature control means, one for providing the aqueous phase at a controlled temperature (1), the other for providing the organic phase at a controlled temperature (2). Both vessels are further equipped with automatic stirrers (3). The aqueous phase is circulated in a closed loop (4) using a pump (5), while passing through a high shear mixing unit (6). The organic phase is added into the aqueous phase within the high shear mixing unit with the aid of a dosing pump (7) and via an injector nozzle which is shown in more detail in FIG. 6.

Figure 6:
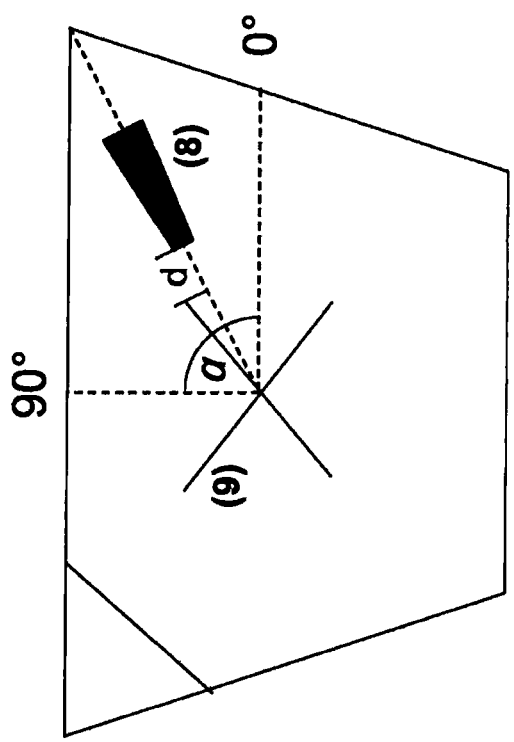
FIG. 6 is a detailed schematic drawing of the high shear mixing unit ((6) of FIG. 5).

As shown in FIG. 6, the nozzle (8) is placed within the aqueous phase inside the high shear mixing unit. The nozzle can be oriented within different angles (u) with respect to the rotor (9) of the high shear mixing unit, and within defined distances (d) of the rotor tip.

The solid dispersion, in particular the MBP obtainable according to the methods provided can be used in a wide variety of forms for administration of drugs such as Compound I, including drugs that are poorly water soluble, and in particular for oral dosage forms. Exemplary dosage forms include powders or granules that can be taken orally either dry or reconstituted by addition of water to form a paste, slurry, suspension or solution; tablets, capsules, or pills. Various additives can be mixed, ground or granulated with the solid dispersion as described herein to form a material suitable for the above dosage forms. Potentially beneficial additives may fall generally into the following classes: other matrix materials or diluents, surface active agents, drug complexing agents or solubilizers, fillers, disintegrants, binders, lubricants, and pH modifiers (e.g., acids, bases, or buffers). Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. At least one function of inclusion of such pH modifiers is to control the dissolution rate of the drug, matrix polymer, or both, thereby controlling the local drug concentration during dissolution.

Additives may be incorporated into the solid amorphous dispersion during or after its formation. In addition to the above additives or excipients, use of any conventional materials and procedures for formulation and preparation of oral dosage forms using the compositions disclosed herein known by those skilled in the art are potentially useful.

Consequently, a further embodiment includes a pharmaceutical preparation containing the solid dispersion as obtained by a method as described herein, in particular as obtained according to steps a) to g) as mentioned above, and more particularly as obtained according to the process described in Example 22.

In still another embodiment, there is provided a solid dispersion as obtained according to the present process for use as a medicament, in particular a solid dispersion comprising HPMCAS and Compound I, more particularly the solid dispersion as obtained according the steps a) to g) above or according to Example 22.

In yet another embodiment there is provided the use of the solid dispersion obtainable by the present steps a) to g) or by the method of Example 22 in the manufacture of medicaments for the treatment of cancer, in particular solid tumors, and more particularly malignant (metastatic) melanomas.

In still another embodiment, there is provided the solid dispersion as obtained according to steps a) to g) above or the method of Example 22 for use as a medicament for the treatment of cancer, in particular solid tumors, and more particularly malignant (metastatic) melanoma.

c) pH-Controlled Precipitation

The process involves the microprecipitation of Compound I in an ionic polymer (for example, HPMC-AS). In this process, Compound I and the polymer are dissolved at a high pH and precipitated by lowering the pH of the solution or vice versa.

In a preferred embodiment, the polymer is HPMC-AS which is insoluble at low pH. Compound I and HPMC-AS are dissolved in an organic solvent such as dimethylformamide, dimethylacetamide (DMA), dimethyl sulfoxide (DMSO), N-methyl pyrrolidone (NMP), and the like. The pH of the solution is then lowered, for example by adding an acid. Addition of the acid includes mixing of the Compound I and polymer solution and the acid, for example by adding acid to the Compound I and polymer solution, adding the Compound I and polymer solution to the acid, or mixing the two simultaneously. At the lowered pH, both Compound I and HPMC-AS simultaneously precipitate out, resulting in a solid molecular complex containing Compound I embedded in a matrix formed by HPMC-AS. The resulting solid molecular complex may then be washed with water to remove the organic solvent.

d) Hot Melt Extrusion Process

Microprecipitation of the Compound I in a polymer (such as HPMC-AS) can be achieved in certain embodiments by a hot melt extrusion process. Compound I and the polymer are mixed and then fed continuously to a temperature-controlled extruder causing the Compound I to be molecularly dispersed in the molten polymer. The resulting extrudate is cooled to room temperature and milled into a fine powder.

e) Supercritical Fluid Process

In this process Compound I and a polymer (such as HPMC-AS) are dissolved in a supercritical fluid such as liquid nitrogen or liquid carbon dioxide. The supercritical fluid is then removed by evaporation leaving the Compound I microprecipitated in the matrix formed by the polymer. In a different method, the Compound I and a polymer (such as HPMC-AS) are dissolved in a suitable solvent. A microprecipitated powder can then be formed by spraying the solution in a supercritical fluid which acts as an antisolvent.

The resulting solid molecular complex prepared by any method may be further processed to provide suitable bioavailability. The solid molecular complex may be processed by roller compaction, for example the complex and other powders may be blended and roller compacted to form a ribbon or sheet that is then milled, mixed with other excipients and encapsulated into 2-pc hard gelatin capsule shells at the desired strength.

Determination of Whether Compound I is in Amorphous Form

Whether Compound I has been successfully immobilized in amorphous form can be determined by various means, including powder X-ray diffraction. In addition, the glass transition temperature of the complex can be measured using modulated DSC and this can also provide information whether the dispersion is a multiphase or uniphase. A uniphase is indicative of such immobilization.

Crystalline Polymorphs (A) Crystalline Polymorph Form 1

Crystalline polymorphs of propane-1-sulfonic acid {3-[5-(4-chloro-phenyl)-1H-pyrrolo[2,3-b]pyridine-3-carbonyl]-2,4-difluoro-phenyl}-amide (Compound I) are provided. In one embodiment, crystalline polymorph Form 1 is provided, wherein the polymorph exhibits a powder x-ray diffraction pattern having characteristic peak locations of approximately 4.7, 9.4, 11.0, 12.5, and 15.4 degrees 2θ. In one embodiment, polymorph Form 1 exhibits a powder x-ray diffraction pattern having characteristic peak locations of approximately 4.7, 9.4, 10.0, 11.0, 12.5, 14.2, 15.4, 18.6, and 22.2 degrees 2θ. In one embodiment, polymorph Form 1 exhibits a powder x-ray diffraction pattern having characteristic peak locations of approximately 4.7, 9.4, 10.0, 11.0, 12.5, 14.2, 15.4, 16.1, 18.6, 19.0, 22.2 and 26.8 degrees 2θ. In one embodiment, crystalline polymorph Form 1 exhibits a powder x-ray diffraction pattern substantially the same as the powder x-ray diffraction pattern of FIG. 1. In one embodiment, a purified crystalline polymorph Form 1 is provided. In one embodiment, a purified crystalline polymorph Form 1 is used in the preparation of a mesylate or tosylate salt form of propane-1-sulfonic acid {3-[5-(4-chloro-phenyl)-1H-pyrrolo[2,3-b]pyridine-3-carbonyl]-2,4-difluoro-phenyl}-amide. In one embodiment, a pharmaceutical composition comprising crystalline polymorph Form 1 and at least one excipient or carrier is provided.

Methods of making crystalline polymorph Form 1 of propane-1-sulfonic acid {3-[5-(4-chloro-phenyl)-1H-pyrrolo[2,3-b]pyridine-3-carbonyl]-2,4-difluoro-phenyl}-amide are provided. The method may include recrystallization of any form of propane-1-sulfonic acid {3-[5-(4-chloro-phenyl)-1H-pyrrolo[2,3-b]pyridine-3-carbonyl]-2,4-difluoro-phenyl}-amide from a mixture of a lower ketone and a lower alcohol, e.g., acetone:absolute ethanol. The propane-1-sulfonic acid {3-[5-(4-chloro-phenyl)-1H-pyrrolo[2,3-b]pyridine-3-carbonyl]-2,4-difluoro-phenyl}-amide may be recrystallized from acetone:absolute ethanol in a ratio of from 1:1 to 5:1, preferably 2:1 by volume.

(B) Crystalline Polymorph Form 2

Figure 2:
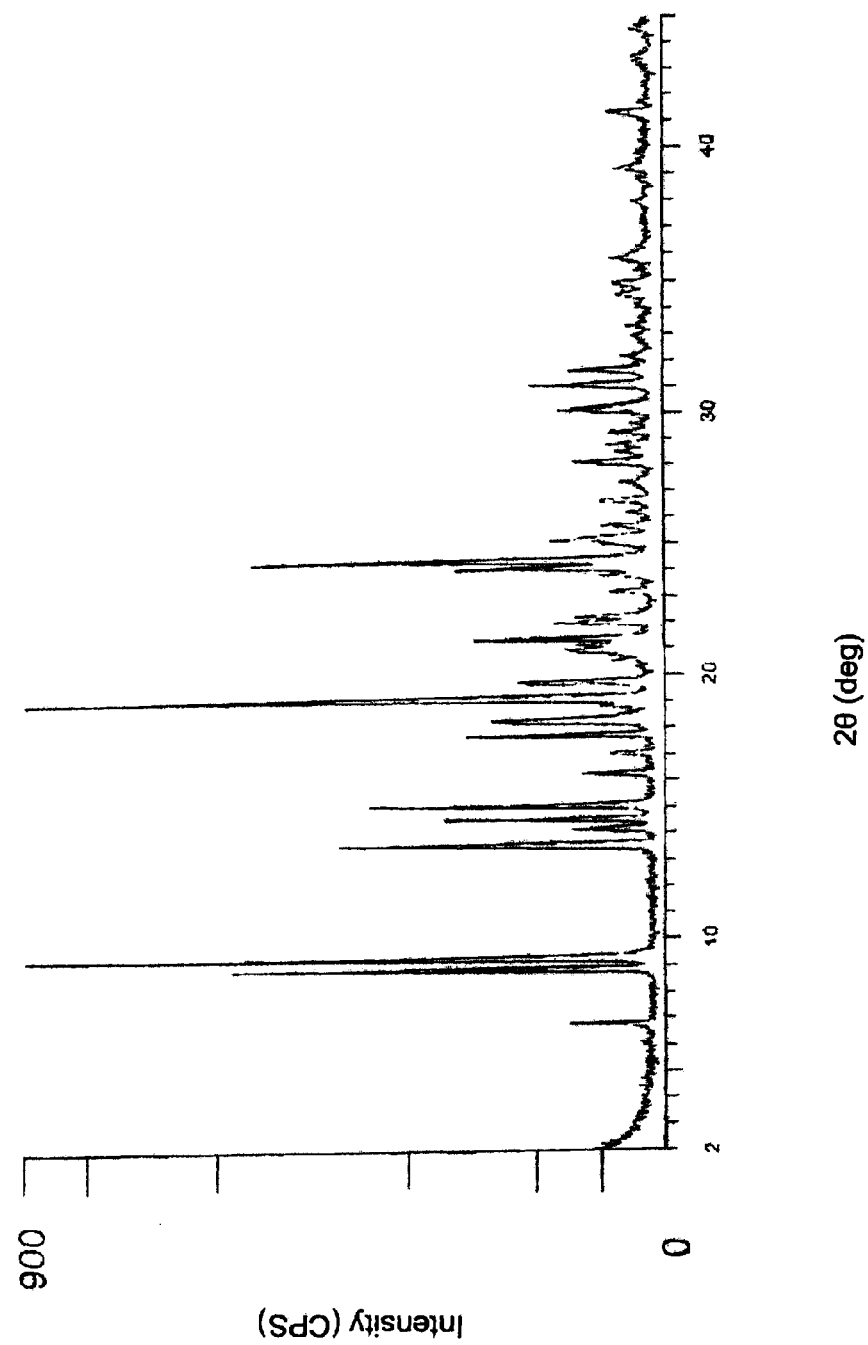
FIG. 2 is a powder x-ray diffraction pattern for the crystalline polymorph Form 2 of Compound I.

Crystalline polymorph Form 2 of propane-1-sulfonic acid {3-[5-(4-chloro-phenyl)-1H-pyrrolo[2,3-b]pyridine-3-carbonyl]-2,4-difluoro-phenyl}-amide is provided, wherein the polymorph exhibits a powder x-ray diffraction pattern having characteristic peak locations of approximately 8.8, 9.2, 13.5, 19.1 and 24.4 degrees 2θ. In one embodiment, polymorph Form 2 exhibits a powder x-ray diffraction pattern having characteristic peak locations of approximately 6.7, 8.8, 9.2, 13.5, 15.0, 17.7, 19.1, 19.7, 21.4 and 24.4 degrees 2θ. In one embodiment, polymorph Form 2 exhibits a powder x-ray diffraction pattern having characteristic peak locations of approximately 6.7, 8.8, 9.2, 13.5, 14.1, 14.5, 15.0, 16.2, 17.0, 17.7, 19.1, 19.7, 21.4, 22.2, 24.1, 24.4, and 28.1 degrees 2θ. In one embodiment, crystalline polymorph Form 2 exhibits a powder x-ray diffraction pattern substantially the same as the powder x-ray diffraction pattern of FIG. 2. In one embodiment, a purified crystalline polymorph Form 2 is provided. In one embodiment, a purified crystalline polymorph Form 2 is used in the preparation of a mesylate or tosylate salt form of propane-1-sulfonic acid {3-[5-(4-chloro-phenyl)-1H-pyrrolo[2,3-b]pyridine-3-carbonyl]-2,4-difluoro-phenyl}-amide. In one embodiment, a pharmaceutical composition comprising crystalline polymorph Form 2 and at least one excipient or carrier is provided.

Methods of making crystalline polymorph Form 2 of propane-1-sulfonic acid {3-[5-(4-chloro-phenyl)-1H-pyrrolo[2,3-b]pyridine-3-carbonyl]-2,4-difluoro-phenyl}-amide are provided, wherein the method comprises direct crystallization from dimethylacetamide/methanol and recrystallization of any form of propane-1-sulfonic acid {3-[5-(4-chloro-phenyl)-1H-pyrrolo[2,3-b]pyridine-3-carbonyl]-2,4-difluoro-phenyl)}-amide from a suitable ether (including cyclic ethers), ester or ketone solvent such as methyl-t-butyl ether:tetrahydrofuran, ethyl acetate, or acetone. In one embodiment, Form 2 of propane-1-sulfonic acid {3-[5-(4-chloro-phenyl)-1H-pyrrolo[2,3-b]pyridine-3-carbonyl]-2,4-difluoro-phenyl}-amide is prepared by heating/melting any form of the compound and re-solidifying.

Mesylate Salt of Compound I

A mesylate salt form of propane-1-sulfonic acid {3-[5-(4-chloro-phenyl)-1H-pyrrolo[2,3-b]pyridine-3-carbonyl]-2,4-difluoro-phenyl}-amide is provided. In one embodiment, a mesylate salt form of propane-1-sulfonic acid {3-[5-(4-chloro-phenyl)-1H-pyrrolo[2,3-b]pyridine-3-carbonyl]-2,4-difluoro-phenyl}-amide is provided. In one embodiment, the mesylate salt form is substantially crystalline. In one embodiment, the mesylate salt form is partially amorphous. In one embodiment, the mesylate salt form is substantially amorphous. In one embodiment, the mesylate salt is used in a microprecipitated bulk process to formulate the salt in an amorphous form. In one embodiment, the mesylate salt is generated in situ in a microprecipitated bulk process to formulate the salt in an amorphous form. In one embodiment, a composition is provided comprising the mesylate salt.

Tosylate Salt of Compound I

A tosylate salt of propane-1-sulfonic acid {3-[5-(4-chloro-phenyl)-1H-pyrrolo[2,3-b]pyridine-3-carbonyl]-2,4-difluoro-phenyl}-amide is provided. In one embodiment, the tosylate salt form is substantially crystalline. In one embodiment, the tosylate salt form is partially amorphous. In one embodiment, the tosylate salt form is substantially amorphous. In one embodiment, the tosylate salt is used in a microprecipitated bulk process to formulate the salt in an amorphous form. In one embodiment, the tosylate salt is generated in situ in a microprecipitated bulk process to formulate the salt in an amorphous form. In one embodiment, a composition is provided comprising the tosylate salt.

Kinase Targets and Indications

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Description of specific target protein kinases contemplated by the present invention follow:

A-Raf:

Target kinase A-Raf (i.e., v-raf murine sarcoma 3611 viral oncogene homolog 1) is a 67.6 kDa serine/threonine kinase encoded by chromosome Xp11.4-p11.2 (symbol: ARAF). The mature protein comprises RBD (i.e., Ras binding domain) and phorbol-ester/DAG-type zinc finger domain and is involved in the transduction of mitogenic signals from the cell membrane to the nucleus. A-Raf inhibitors may be useful in treating neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf:

Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase B-Raf is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, B-Raf kinase is a key component of the RAS→Raf→MEK→ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAF inhibitors, and this can be envisioned as a transition in codon 529 from ACC to ATC.

Niihori et al., report that in 43 individuals with cardio-facio-cutaneous (CFC) syndrome, they identified two heterozygous KRAS mutations in three individuals and eight BRAF mutations in 16 individuals, suggesting that dysregulation of the RAS-RAF-ERK pathway is a common molecular basis for the three related disorders (Niihori et al., Nat Genet. 2006, 38(3):294-6).

c-Raf-1:

Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein). c-Raf-1 is implicated in carcinomas, including colorectal, ovarian, lung and renal cell carcinoma. C-Raf-1 is also implicated as an important mediator of tumor angiogenesis (Hood, J. D. et al., 2002, Science 296, 2404). C-Raf-1 inhibitors may also be useful for the treatment of acute myeloid leukemia and myelodysplastic syndromes (Crump, Curr Pharm Des 2002, 8(25):2243-8). Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2): 139-42).

A-Raf, B-Raf and/or C-Raf inhibitors may be useful in treating A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, sarcoma, carcinoma (e.g. gastrointestinal, liver, bile duct (cholangiocarcinoma), colorectal, lung, breast, pancreatic, thyroid, renal, ovarian, prostate), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-facio-cutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

Alternative Compound Forms or Derivatives

Propane-1-sulfonic acid {3-[5-(4-chlorophenyl)-1H-pyrrolo [2,3-b] pyridine-3-carbonyl-2,4-difluoro-phenyl]-amide}) contemplated herein is described with reference to the specific compound. In addition, Compound I may exist in a number of different forms or derivatives, all within the scope of the present inventions. Alternative forms or derivatives, include, for example, (a) prodrugs, and active metabolites (b) tautomers (c) pharmaceutically acceptable salts and (d) solid forms, including different crystal forms, polymorphic or amorphous solids, including hydrates and solvates thereof, and other forms.

Prodrugs and Metabolites

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. Prodrugs may include variants wherein an —NH group of the compound has undergone acylation, such as the 1-position of the pyrrolo[2,3-b]pyridine ring or the nitrogen of the sulfonamide group of Compound I or a pharmaceutically acceptable salt thereof, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative Reactions:

Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive Reactions:

Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without Change in the Oxidation State:

Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656, 838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physicochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

Tautomers

It is understood that some compounds may exhibit tautomerism. In such cases, the formulae provided herein expressly depict only one of the possible tautomeric forms. It is therefore to be understood that Compound I provided herein is intended to represent any tautomeric form of the depicted compound and is not to be limited merely to the specific tautomeric form depicted by the drawing of the compound.

Pharmaceutically Acceptable Salts

Unless specified to the contrary, specification of Compound I herein includes pharmaceutically acceptable salts of such compound. Thus, Compound I can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. Compound I possesses a sufficiently acidic and a sufficiently basic functional group, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, dichloroacetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see *Remington's Pharmaceutical Sciences*, 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, Compound I is complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining Compound I with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, Compound I or salts thereof described herein are intended to cover hydrated or solvated as well as unhydrated or unsolvated forms of the identified material. For example, Compound I or salts thereof includes both hydrated and non-hydrated forms. Other examples of solvates include the structures in combination with a suitable solvent, such as isopropanol, ethanol, methanol, DMSO, ethyl acetate, acetic acid, or ethanolamine.

Formulations and Administration

Compound I or any form thereof as described herein (including solid molecular complexes) will typically be used in therapy for human subjects. However, Compound I and compositions thereof may also be used to treat similar or identical indications in other animal subjects, and can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, 21$^{st}$ edition, Lippincott, Williams and Wilkins, Philadelphia, Pa., 2005 (hereby incorporated by reference herein).

In some embodiments, compositions (including solid complexes as disclosed herein) include pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, difatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropylmethyl celluloses), HPC (hydroxypropyl cellulose), hydroxyethyl cellulose, hypromellose, and the like.

In an embodiment of the present invention, a formulation is provided which comprises the aforementioned solid complex suspended in an aqueous vehicle. The formulation may further comprise colloidal silicon dioxide which has been found to stabilize the suspension. The silicon dioxide is preferably present in an amount of at least 0.5% by weight of the formulation. The aqueous vehicle preferably is about 2% by weight hydroxypropyl cellulose.

In some embodiments, oral administration may be used. Pharmaceutical preparations for oral use can be formulated into conventional oral dosage forms such as capsules, tablets, and liquid preparations such as syrups, elixirs, and concentrated drops. Compound I may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, polyvinylpyrrolidone, carbopol gel, polyethylene glycol, and/or titanium dioxide, lacquer solutions, and suitable organic solvents or solvent mixtures.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compound may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compound I and compositions thereof for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, Compound I or compositions thereof may be formulated in solid form, including, for example, lyophilized forms, and redissolved or suspended prior to use.

In some embodiments, transmucosal, topical or transdermal administration may be used. In such formulations of Compound I, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of Compound I for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, Compound I or compositions thereof are administered as inhalants. Compound I or compositions thereof may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. Compound I or compositions thereof may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of Compound I or compositions thereof to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

Compound I or compositions thereof may also be used in combination with other therapies for treating the same disease. Such combination use includes administration of Compound I and one or more other therapeutics at different times, or co-administration of Compound I and one or more other therapies. In some embodiments, dosage may be modified for Compound I or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than Compound I or compositions thereof, or at the same time as Compound I or compositions thereof. Use in combination also includes use with a therapy or medical procedure that is administered once or infrequently, such as surgery, along with Compound I or compositions thereof administered within a short time or longer time before or after the other therapy or procedure. In some embodiments, the present invention provides for delivery of Compound I or compositions thereof and one or more other drug therapeutics delivered by a different route of administration or by the same route of administration. The use in combination for any route of administration includes delivery of Compound I or compositions thereof and one or more other drug therapeutics delivered by the same route of administration together in any formulation, including formulations where the two compounds are chemically linked in such a way that they maintain their therapeutic activity when administered. In one aspect, the other drug therapy may be co-administered with Compound I or compositions thereof. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of Compound I and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

EXAMPLES

Examples related to the present invention are described below. In most cases, alternative techniques can be used. The examples are intended to be illustrative and are not limiting or restrictive to the scope of the invention.

Example 1

This example describes the formation of a solid molecular complex comprising Compound I and HPMC-AS.

Propane-1-sulfonic acid {3-[5-(4-chloro-phenyl)-1H-pyrrolo[2,3-b]pyridine-3-carbonyl]-2,4-difluoro-phenyl}-amide and HPMC-AS in a ratio of 3:7 (30% compound and 70% polymer) were dissolved in dimethylacetamide (DMA). The resulting solution was then added with stirring to very cold dilute hydrochloric acid resulting in the co-precipitation of propane-1-sulfonic acid {3-[5-(4-chloro-phenyl)-1H-pyrrolo[2,3-b]pyridine-3-carbonyl]-2,4-difluoro-phenyl}-amide and HPMC-AS as a solid molecular complex wherein propane-1-sulfonic acid {3-[5-(4-chloro-phenyl)-1H-pyrrolo[2,3-b]pyridine-3-carbonyl]-2,4-difluoro-phenyl}-amide was present in a nanoparticulate size range. The ratio of DMA to acid was in the range of 1:5 to 1:10. The co-precipitate was then washed with water to remove DMA, filtered, dried to <2% moisture content and passed through a #30 mesh screen prior to evaluation. The resulting solid molecular complex was 30% by weight propane-1-sulfonic acid {3-[5-(4-chloro-phenyl)-1H-pyrrolo[2,3-b]pyridine-3-carbonyl]-2,4-difluoro-phenyl}-amide and 70% by weight HPMC-AS.

The properties of the resulting solid molecular complex were as follows.

| Property | Measure |
| --- | --- |
| X-ray pattern | Amorphous |
| Tg (range C) | 100-120 |
| Drug loading (% w/w) | 30 |
| Bulk Density (g./cm3) | 0.15-0.45 |
| Absolute Density (g/cm3) | 1-1.5 |
| Specific Surface Area (cm2/g) | 3-10 |
| Intrinsic particle size (nm) | 150 |
| Moisture Content | <2% |
| DMA Content | <0.2% |

Examples 2 to 7

Solid molecular complexes comprising Compound I and HPMC-AS were prepared using methods analogous to that used in Example 1 to produce solid molecular complexes wherein the ratio of the amount by weight of propane-1-sulfonic acid {3-[5-(4-chloro-phenyl)-1H-pyrrolo[2,3-b]pyridine-3-carbonyl]-2,4-difluoro-phenyl}-amide within the solid molecular complex to the amount by weight of the ionic polymer therein is 3:7, 5:5, 5:5, 4:6, 4:6, and 2:8, respectively.

The solid molecular complexes produced in Examples 1 to 7 were evaluated for amorphous nature by powder XRD. The samples were exposed under OPEN conditions by placing the sample in a bottle in the stability chamber without a lid or closure or cap on the at 40° C. and 75% relative humidity (RH) and the properties of the solid molecular complexes following such exposure were observed. The exposure periods are shown in the table below. At the end of the exposure period, a sample of the powder was taken from the bottle and placed in powder X-ray diffraction (XRD) chamber and diffraction pattern obtained. The samples were deemed stable if the powder XRD profile did not show crystalline peaks. The prepared and stored samples were also evaluated by polarized light microscopy. The incidence of polarized light results in a birefringence phenomenon, if crystals are present in the sample. For an amorphous sample, such a test could indicate presence of crystal material which indicates that amorphous material is unstable.

TABLE 1

Evaluation of drug-HPMC-AS solid molecular complexes at varying ratios

| Ex. | Drug: Polymer ratio | Lot number ZG-37427-xxx | Results after open exposure at 40° C./75% RH |
| --- | --- | --- | --- |
| 1 | 3:7 | −183 | STABLE after storage for up to 3 months |
| 2 | 3:7 | −194 | STABLE after storage for up to 3 months |
| 3 | 5:5 | −175 | UNSTABLE due to very small crystal peaks after storage for 3 weeks |
| 4 | 5:5 | −185 | UNSTABLE due to crystal peaks after 2 months |
| 5 | 4:6 | −154 | STABLE after 3 weeks of storage No apparent birefringence by microscopy |
| 6 | 4:6 | −178 | STABLE after storage for up to 2 months |
| 7 | 2:8 | −199 | STABLE after storage for 1 month |

Example 8

This example describes the formation of a solid molecular complex comprising propane-1-sulfonic acid {3-[5-(4-chloro-phenyl)-1H-pyrrolo[2,3-b]pyridine-3-carbonyl]-2,4-difluoro-phenyl}-amide and EUDRAGIT® L 100. Eudragit L 100 is another anionic polymer, a polymethyl methacrylate ester with methacrylic acid as a functional group and dissolves at pH 6.0 and above.

Propane-1-sulfonic acid {3-[5-(4-chloro-phenyl)-1H-pyrrolo[2,3-b]pyridine-3-carbonyl]-2,4-difluoro-phenyl}-amide and EUDRAGIT® L 100 in a ratio of 3:7 (30% compound and 70% polymer) were dissolved in dimethylacetamide (DMA). The resulting solution was then added with stirring to very cold dilute hydrochloric acid resulting in the co-precipitation of propane-1-sulfonic acid {3-[5-(4-chloro-phenyl)-1H-pyrrolo[2,3-b]pyridine-3-carbonyl]-2,4-difluoro-phenyl}-amide and Eudragit L 100 as a solid molecular complex wherein the drug was present in a nanoparticulate size range. The co-precipitate was then washed with water to remove DMA, filtered, dried, and milled to a fine powder. The ratio of DMA to acid was in the range of 1:5 to 1:10. The co-precipitate was then washed with water to remove DMA, filtered, dried to <2% moisture content and passed through a #30 mesh screen prior to evaluation. The resulting solid molecular complex was 30% by weight propane-1-sulfonic acid {3-[5-(4-chloro-phenyl)-1H-pyrrolo[2,3-b]pyridine-3-carbonyl]-2,4-difluoro-phenyl}-amide and 70% by weight Eudragit L 100.

The solid molecular complex samples were evaluated for amorphous nature right after preparation by powder XRD. The samples were the subjected to storage under OPEN conditions at 40 C/75% RH for varying periods of time similar to that shown in Examples 1-7. At the end of the exposure period, a sample of the powder was taken from the bottle and placed in powder X-ray diffraction (XRD) chamber and diffraction pattern obtained. The samples were deemed stable if the powder XRD profile did not show crystalline peaks. The prepared and stored samples were also evaluated by polarized light microscopy. The incidence of polarized light results in a birefringence phenomenon, if crystals are present in the sample. For an amorphous sample, such a test could indicate presence of crystal material which indicates that amorphous material is unstable. Results for this Example are shown in Table 2 below.

Example 9

This example was performed with all the same steps as Example 8, with the exception that propane-1-sulfonic acid {3-[5-(4-chloro-phenyl)-1H-pyrrolo[2,3-b]pyridine-3-carbonyl]-2,4-difluoro-phenyl}-amide and EUDRAGIT® L 100 were dissolved in dimethylacetamide (DMA) in a ratio of 4:6 (40% compound and 60% polymer) instead of 3:7 as in Example 8. Results for this Example are shown in Table 2 below.

Example 10

Solid molecular complexes containing the propane-1-sulfonic acid {3-[5-(4-chloro-phenyl)-1H-pyrrolo[2,3-b]pyridine-3-carbonyl]-2,4-difluoro-phenyl}-amide and Eudragit L 100-55 in ratios of 4:6 and 5:5, respectively, were formed using the microprecipitation process same as that in Example 1. Eudragit L 100-55 is similar to L 100 except that it dissolves at pH 5.5 and above and therefore more closely resembles HPMC-AS in its pH solubility profile. The prepared and stored samples were evaluated by powder XRD. Results for this Example are shown in Table 2 below.

Example 11

This example describes the formation of a solid molecular complex comprising the propane-1-sulfonic acid {3-[5-(4-chloro-phenyl)-1H-pyrrolo[2,3-b]pyridine-3-carbonyl]-2,4-difluoro-phenyl}-amide and hydroxypropylmethylcellulose phthalate (HPMCP), another anionic polymer used for enteric purposes. HPMCP is a cellulose polymer in which some of the hydroxyl groups are replaced with phthalyl esters from 27-35%. It starts dissolving at pH 5.5 and higher. Solid molecular complexes containing propane-1-sulfonic acid {3-[5-(4-chloro-phenyl)-1H-pyrrolo[2,3-b]pyridine-3-carbonyl]-2,4-difluoro-phenyl}-amide and HPMCP in 1:1 ratio were prepared using same process as that used in Example 1. The prepared and stored samples were evaluated by XRD. Results for this Example are shown in Table 2 below.

TABLE 2

Evaluation of drug-polymer solid molecular complexes at varying ratios

| Ex. | Polymer | Lot # ZG-37427-xxx | Drug Polymer Ratio | Initial | Storage under open conditions at 40° C./75% RH |
|---|---|---|---|---|---|
| 8 | Eudragit L100 | -192 | 3:7 | Amorphous, STABLE | STABLE for up to 3 months |
| 9 | Eudragit L100 | -155 | 4:6 | Amorphous, STABLE | UNSTABLE; birefringence observed in polarized light microscopy after 3 weeks |
| 10 | Eudragit L100-55 | -170 | 5:5 | Amorphous, STABLE | UNSTABLE, crystal peaks seen after 3 weeks |
| 11 | HIPMCP | -187 | 5:5 | Crystalline, UNSTABLE | |

Based on Examples 1-11, the propane-1-sulfonic acid {3-[5-(4-chloro-phenyl)-1H-pyrrolo[2,3-b]pyridine-3-carbonyl]-2,4-difluoro-phenyl}-amide-polymer ratio of 4:6 was the highest drug loading (40%) sustainable upon storage with HPMC-AS as polymer. Therefore, this ratio was chosen for comparison with other polymers in a separate study.

Examples 12-16 were prepared by a microprecipitation process similar to that for Example 1. The dried powder samples were evaluated for amorphous nature right after preparation by powder XRD. The samples were further subjected to storage under OPEN conditions at 40 C/75% RH for varying periods of time similar to that shown in Examples 1-7. The results are shown in Table 3 below.

Example 12

Solid molecular complexes containing propane-1-sulfonic acid {3-[5-(4-chloro-phenyl)-1 H-pyrrolo[2,3-b]pyridine-3-carbonyl]-2,4-difluoro-phenyl}-amide and HPMC-AS in ratio of 4:6 were found to be amorphous right after preparation (Table 3) and subject to storage for 4 weeks at 40 C/75% RH.

The XRD of the solid molecular complexes were evaluated.

Example 13

Solid molecular complexes containing propane-1-sulfonic acid {3-[5-(4-chloro-phenyl)-1H-pyrrolo[2,3-b]pyridine-3-carbonyl]-2,4-difluoro-phenyl}-amide and HPMCP in ratio of 4:6 were found to be amorphous right after preparation (Table 3) and subject to storage for 4 weeks at 40 C/75% RH.

Example 14

Solid molecular complexes containing propane-1-sulfonic acid {3-[5-(4-chloro-phenyl)-1H-pyrrolo[2,3-b]pyridine-3-carbonyl]-2,4-difluoro-phenyl}-amide and Eudragit L 100-55 in 4:6 ratio was found to be amorphous right after preparation (Table 3) and subject to storage for 4 weeks at 40 C/75% RH.

Example 15

Solid molecular complexes containing propane-1-sulfonic acid {3-[5-(4-chloro-phenyl)-1H-pyrrolo[2,3-b]pyridine-3-carbonyl]-2,4-difluoro-phenyl}-amide and polyvinylacetate phthalate (PVAP) in 4:6 ratio was crystalline right after preparation and therefore not subject to further testing. PVAP is an anionic enteric polymer formed as the phthalate ester of polyvinylacetate and contains 55-62% of phthalyl groups. It has a low Tg of 42.5 C which renders it unsuitable as a stabilizing polymer matrix. It dissolves at pH>5.

Example 16

Solid molecular complexes containing propane-1-sulfonic acid {3-[5-(4-chloro-phenyl)-1H-pyrrolo[2,3-b]pyridine-3-carbonyl]-2,4-difluoro-phenyl}-amide and cellulose acetate phthalate (CAP) in ratio of 4:6 was crystalline right after preparation and therefore not subject to further testing.

The powder XRD profiles of Examples 12-16 at the initial stage right after preparation are shown in Table 3.

TABLE 3

Evaluation of drug-polymer solid molecular complexes at fixed ratio of 4:6 (40% drug and 60% polymer):

| Ex. | Polymer | Lot # ZG-39422-xxx | Initial XRD |
| --- | --- | --- | --- |
| 12 | HPMC-AS, LF | -129A | STABLE Amorphous |
| 13 | HPMCP | -129B | STABLE Amorphous |
| 14 | Eudragit L100-55 | -129C | STABLE Amorphous |
| 15 | PVAP | -129D | UNSTABLE Crystalline |
| 16 | CAP | -129E | UNSTABLE Crystalline |

After 1 week, the sample prepared under Example 13 showed a small peak in powder XRD indicating conversion to crystalline form. This peak became more pronounced after 2 weeks of storage.

Example 17

Samples prepared in Examples 12 and 14 did not indicate any crystalline peak in powder XRD profiles up to the end of 4 weeks of storage.

In order to further differentiate the samples from Examples 12 and 14, the samples were subject to dissolution test by placing an amount of solid molecular complex equivalent to 80 mg of propane-1-sulfonic acid {3-[5-(4-chloro-phenyl)-1H-pyrrolo[2,3-b]pyridine-3-carbonyl]-2,4-difluoro-phenyl}-amide in 900 mL of pH 6.8 phosphate buffer medium containing 0.09% HTAB surfactant in USP Paddle dissolution apparatus at a speed of 75 rpm.

In one set of experiments, a sieve cut of granules of Examples 12 and 14 were obtained by separating the #25/40 mesh sieve size fraction and subjecting to dissolution test. The HPMC-AS solid molecular complexes had increased amounts with respect to % dissolved as compared to Eudragit L 100-55 solid molecular complexes, with the HPMC-AS solid molecular complexes being about 85% dissolved at 200 minutes and with the Eudragit L 100-55 solid molecular complexes being about 40% dissolved at 200 minutes.

In another experiment, the solid molecular complex samples from Examples 12 and 14 were pre-wetted with vehicle containing hydroxypropyl cellulose (Klucel) for improved dispersion and subjected to dissolution test. The HPMC-AS solid molecular complexes had increased amounts with respect to % dissolved as compared to Eudragit L 100-55 solid molecular complexes, with the HPMC-AS solid molecular complexes being about 60-65% dissolved at 200 minutes and with the Eudragit L 100-55 solid molecular complexes being about 20-25% dissolved at 200 minutes.

Based on results from these experiments, the HPMC-AS was a superior polymer in stabilizing the drug upon storage under stress conditions but also enabling drug release and maintaining supersaturation of amorphous drug during dissolution without reverting to crystalline form within the period of testing. The Eudragit L 100-55 did not enhance drug release as compared to HPMC-AS and therefore is not expected to provide the exposure and bioavailability as well as HPMC-AS. At the end of 3 h, almost 90% drug was released from Example 12 (HPMC-AS) while Example 14 (Eudragit L-100-55) had only about 50% drug released. Thus, a propane-1-sulfonic acid {3-[5-(4-chloro-phenyl)-1H-pyrrolo[2,3-b]pyridine-3-carbonyl]-2,4-difluoro-phenyl}-amide and HPMC-AS solid molecular complex made by the microprecipitation process therefore not only stabilizes the amorphous compound for handling and storage but also ensures rapid drug release resulting in superior dissolution and therefore bioavailability.

Example 18

This Example demonstrates the stabilization of solid molecular complexes in aqueous systems. The solid molecular complex of drug-HPMC-AS is suspended in an aqueous vehicle containing 2% hydroxypropylcellulose (Klucel LF). Upon addition of >0.5% w/w colloidal silicon dioxide, the resulting suspension was found to be stable for up to 8 h under normal conditions and for up to 24 h under refrigerated conditions.

Example 19

Propane-1-sulfonic acid {3-[5-(4-chloro-phenyl)-1H-pyrrolo[2,3-b]pyridine-3-carbonyl]-2,4-difluoro-phenyl}-amide can exist in polymorphic forms, for example as polymorphic forms 1 or 2, where such polymorphic forms may be isolated as the substantially pure polymorph. The desired polymorphic form may be prepared, for example, by using appropriate crystallization conditions. For example, Form 1 was isolated by recrystallization from acetone/absolute ethanol (e.g. 1:1 to 5:1, preferably 2:1 by volume) as explained in detail herein. Form 2 can be formed for example directly via crystallization from dimethylacetamide/methanol or under a variety of recrystallization conditions, for example, is formed by recrystallization from methyl-t-butyl ether/tetrahydrofuran, ethyl acetate, acetone, or is formed by heating/melting and re-solidifying any solid form, such as polymorph Form 1, or a mixture of solid forms. The substantially pure isolated polymorphic forms were characterized by X-Ray Powder Diffraction (XRPD), differential scanning calorimetry (DSC) and infrared spectroscopy (See Example 20 below).

To demonstrate the formation of polymorphic Form 1, propane-1-sulfonic acid {3-[5-(4-chloro-phenyl)-1H-pyrrolo[2,3-b]pyridine-3-carbonyl]-2,4-difluoro-phenyl}-amide (7.8 kg) was treated with acetone:absolute ethanol (1:4 by volume, 19 kg) in a reactor and agitated at 20° C.±5° C. for at least 6 hours. The contents were filtered and the solids were washed with acetone:absolute ethanol (1:4 by volume) mixture. Solids were treated with tetrahydrofuran (26.6 kg), and the suspension was heated to 60° C.±5° C. for at least 30 minutes and agitated. The mixture was cooled to 55° C.±5° C. and methyl-t-butyl ether (92.3 kg) was added.

The resulting suspension was cooled to 20° C.±5° C. for at least 1 hour. The contents were filtered and the solids were washed with methyl-t-butyl ether and dried. The solid was treated with acetone:absolute ethanol (2:1 by volume) in a reactor. The contents were agitated and the suspension was heated at 60° C. until a solution was achieved. The solution was filtered through a large polish filter to remove any residual solid from the methyl-t-butyl ether treatment step. The filtrate was concentrated under vacuum, stirred at 20° C.±5° C. for at least 30 minutes and filtered. The solids were washed with pre-cooled (0° C. to −5° C.) ethanol and dried at 45° C. followed by drying at 75° C. under vacuum until a constant weight was achieved, to provide pure propane-1-sulfonic acid {3-[5-(4-chloro-phenyl)-1H-pyrrolo[2,3-b]pyridine-3-carbonyl]-2,4-difluoro-phenyl}-amide polymorphic Form 1. Form 1 was also prepared treating a sample with 120 mL of acetone:ethanol (1:1 by volume) at refluxing, then filtering hot and removing solvent from the filtrate under vacuum until solid precipitates out.

Example 20

The propane-1-sulfonic acid {3-[5-(4-chloro-phenyl)-1H-pyrrolo[2,3-b]pyridine-3-carbonyl]-2,4-difluoro-phenyl}-amide polymorphic Form 1 and Form 2 were characterized by X-ray powder diffraction, infra-red spectrometry, and differential scanning calorimetry. Samples were analyzed by X-ray powder diffraction (XRPD) using a ShimadzuXRD-6000 X-ray powder diffractometer using Cu Kα radiation. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 3°/min (0.4 sec/0.02° step) from 2.50 to 40° 2θ was used. A silicon standard was analyzed to check the instrument alignment. Data were collected and analyzed using XRD-6100/7000 v.5.0. Sample was prepared for analysis by placing it in an aluminum holder with silicon insert. The results are provided in FIG. 1 (Form 1) and FIG. 2 (Form 2) and the following Table 4.

TABLE 4

XRPD 2θ values for P-0001 polymorphic Form 1 and Form 2.
2θ value (+/−0.2)

| Form 1 | Form 2 |
|---|---|
| 4.7 | |
| | 6.7 |
| | 8.8 |
| 9.4 | 9.2 |
| 10.0 | |
| 11.0 | |
| 12.5 | |
| | 13.5 |
| 14.2 | 14.1 |
| | 14.5 |
| 14.9 | 15.0 |
| 15.4 | |
| 16.1 | 16.2 |
| | 17.0 |
| 17.3 | 17.7 |
| 18.6 | 18.3 |
| 19.0 | 19.1 |
| | 19.7 |
| | 20.6 |
| 20.0 | 20.9 |
| 21.2 | 21.4 |
| 21.6 | 22.0 |
| 22.2 | 22.2 |

TABLE 4-continued

XRPD 2θ values for P-0001 polymorphic Form 1 and Form 2.
2θ value (+/−0.2)

| Form 1 | Form 2 |
|---|---|
| | 23.2 |
| 23.9 | 23.8 |
| | 24.1 |
| | 24.4 |
| | 25.1 |
| | 25.7 |
| 6.1 | 26.6 |
| 6.8 | 28.1 |
| | 28.8 |
| 9.2 | 29.3 |
| | 30.1 |
| | 31.1 |
| | 31.7 |
| | 34.5 |
| | 34.9 |
| | 35.9 |
| | 39.2 |
| | 41.3 |

The propane-1-sulfonic acid {3-[5-(4-chloro-phenyl)-1H-pyrrolo[2,3-b]pyridine-3-carbonyl]-2,4-difluoro-phenyl}-amide polymorphic Form 1 and Form 2 were further analyzed by infra-red spectrometry. Table 5 provides the characteristic wavenumbers observed for each sample.

TABLE 5

IR absorption spectrum wavenumber values for P-0001 polymorphic Form 1 and Form 2.
Wavenumber cm$^{-1}$

| Form 1 | Form 2 |
|---|---|
| 3238 | 3266 |
| | 3121 |
| | 2969 |
| 2879 | 2880 |
| 1709 | |
| 1645 | 1639 |
| 1590 | 1589 |
| 1519 | 1519 |
| 1485 | 1487 |
| 1417 | 1417 |
| 1331 | 1322 |
| 1305 | 1306 |
| 1280 | 1287 |
| 1246 | 1246 |
| 1211 | 1215 |
| 1149 | 1143 |
| 1102 | 1096 |
| 1022 | 1027 |
| 1013 | 1012 |
| 965 | 968 |
| 915 | 916 |
| 891 | 893 |
| | 857 |
| 825 | 825 |
| 796 | 798 |
| 773 | 767 |
| 717 | |
| 685 | 683 |
| 651 | 662 |
| 631 | |
| | 607 |
| 587 | 585 |
| 564 | 558 |
| 550 | |
| 532 | 532 |
| 516 | 508 |
| 503 | |

The propane-1-sulfonic acid {3-[5-(4-chloro-phenyl)-1H-pyrrolo[2,3-b]pyridine-3-carbonyl]-2,4-difluoro-phenyl}-amide polymorphic Form 1 and Form 2 were also analyzed by differential scanning calorimetry (DSC), scanning at 10.00° C. per minute. The DSC thermogram for Form 1 shows an exothermic shift at approximately 152-164° C. and an endothermic peak at 268.0° C. The DSC thermogram for Form 2 shows an endothermic peak at 271.2° C.

Example 21

Propane-1-sulfonic acid {3-[5-(4-chloro-phenyl)-1H-pyrrolo[2,3-b]pyridine-3-carbonyl]-2,4-difluoro-phenyl}-amide is characterized as having functionalities providing both weakly basic and weakly acidic centers which can form organic salt complexes, resulting in improved solubility. For example, the N-7 of the azaindole portion is weakly basic (pKa approximately 4-5) and can form an acid addition salt complex with an organic acid such as benzenesulfonic acid, methylsulfonic acid or toluenesulfonic acid, preferably methanesulfonic acid or toluenesulfonic acid. Such mesylate or tosylate salts provide advantage over the free base, such as an improved solubility, improved intrinsic dissolution rate, and lower melting point than the free base. The improved intrinsic dissolution rate provides an advantage in formulation of the salt, for example, formulation in an amorphous form by methods described in the above examples. The improved solubility provides more efficient and cost effective formulation, for example spray drying or microprecipitated bulk processing can be performed using far less solvent volumes due to the intrinsic solubility. Such advantages may also be provided by formation of the mesylate or tosylate salt in situ during the processing, for example the process of spray drying, solvent controlled precipitation, or pH controlled precipitation. Also, lowered melting of the salt forms provides a more efficient hot melt extrusion process, allowing for the melt to proceed at lower temperatures.

Acid addition salts, including sulfonic acid series of organic anions such as tosylate, besylate or mesylate, of Propane-1-sulfonic acid {3-[5-(4-chloro-phenyl)-1H-pyrrolo[2,3-b]pyridine-3-carbonyl]-2,4-difluoro-phenyl}-amide are preferably formed using acetone, which provides solubility of the free base and is a non-solvent once the salt is formed. Typically, Propane-1-sulfonic acid {3-[5-(4-chloro-phenyl)-1H-pyrrolo[2,3-b]pyridine-3-carbonyl]-2,4-difluoro-phenyl}-amide is added to 20-50 solvent volumes of acetone with stirring and heating (30-35° C.), followed by the addition of 1 equivalent of the desired acid counter ion. The solution is slowly cooled to 2-8° C. and the solid is isolated by either filtration or centrifugation, followed by vacuum drying. The resulting solid may be amorphous, partially amorphous or crystalline, and can be recrystalized as needed from alcohol:acetone:ethyl acetate or alcohol alone to obtain the desired solid in crystalline form.

Figure 3:
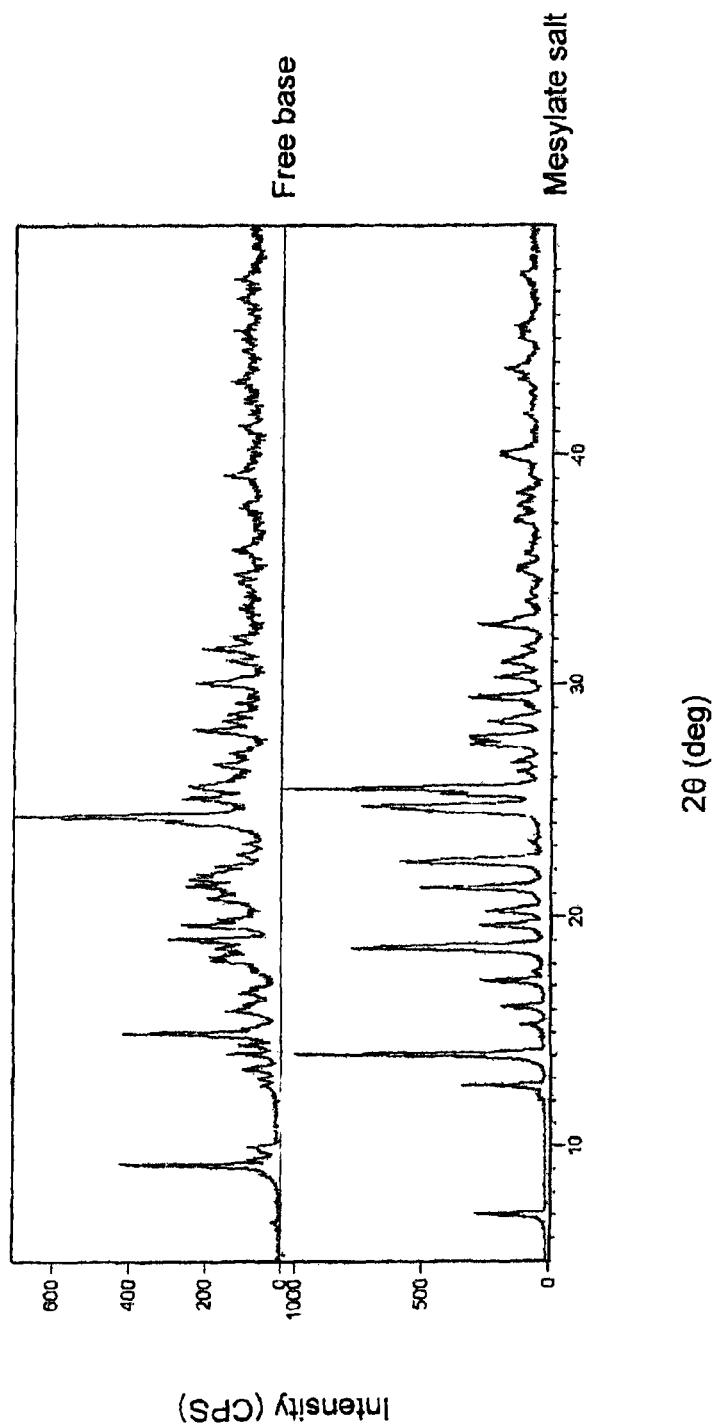
FIG. 3 is a comparison of powder x-ray diffraction pattern for the crystalline polymorph Form 2 and the mesylate salt of Compound I.
Figure 4:
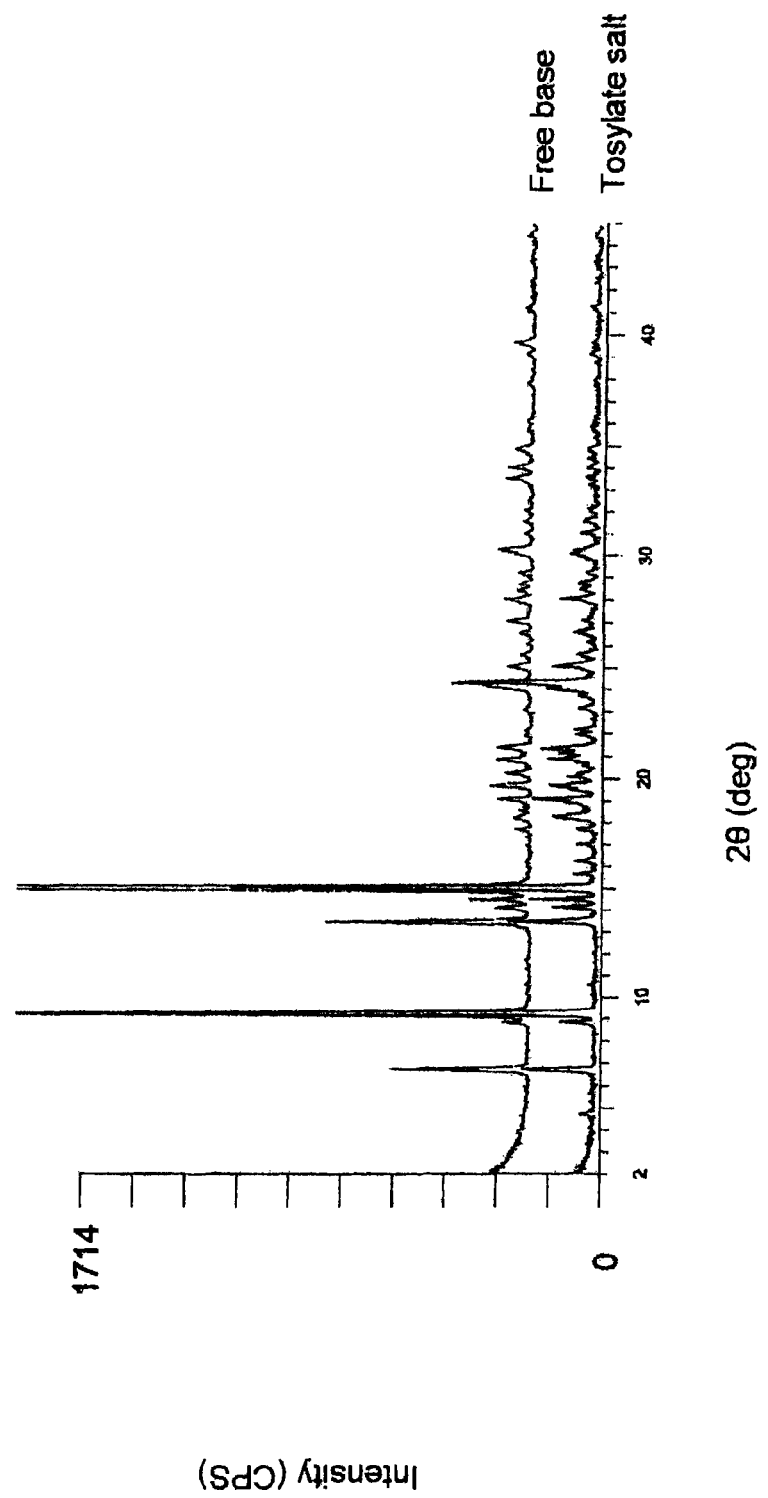
FIG. 4 is a comparison of powder x-ray diffraction pattern for the crystalline polymorph Form 2 and the tosylate salt of Compound I.

The mesylate salt of propane-1-sulfonic acid {3-[5-(4-chloro-phenyl)-1H-pyrrolo[2,3-b]pyridine-3-carbonyl]-2,4-difluoro-phenyl}-amide was prepared by suspending 5 g (9.7 mmol) of polymorph Form 2 in 100 mL of acetone, mixing with heating 30-35° C. Methanesulfonic acid (0.63 mL, 9.7 mmol) was added and the solution cooled to 5° C. over 30 minutes. The resulting solid was isolated by filtration, washed and dried under vacuum to provide the desired salt. The tosylate salt was prepared similarly. Exemplary XRPD patterns for the mesylate and tosylate salts are provided in FIGS. 3 and 4, respectively, as compared to the free base polymorph Form 2. The DSC thermogram for the mesylate salt shows an endothermic peak at approximately 231° C. The DSC thermogram for the tosylate salt shows an endothermic peak at approximately 223° C. and another at approximately 253° C.

The resulting salts are processed through the techniques discussed in the above examples, such as spray drying, solvent controlled precipitation, pH controlled precipitation, or hot melt extrusion to provide the preferred amorphous form, or further processed with suitable excipient materials to provide for a directly compressible or encapsulated dosage form. The salt forms have advantages in such processes, such as to minimize solvent utilization, increase yield, purity and throughput, as well as achieve constructs not attainable using conventional solvent techniques.

Example 22

This example describes the preparation of a solid dispersion (MBP) of amorphous Compound I in HPMCAS
Preparation of the DMA Phase:
The concentration of Compound I and HPMCAS in the organic solvent was 35% (w/w), while the ratio of Compound I and HPMCAS is 30 to 70: The temperature of the solution was adjusted to 70° C.
In a 250 ml double jacketed glass flask reactor 21 g of Compound I were dissolved in 130 g Dimethylacetamide (DMA) at 20-25° C. Under stirring. 48.9 g of HPMC-AS were added to the solution. The mixture was heated up to 70° C. A clear solution was obtained.
Preparation of the Aqueous Phase
In a double jacketed 2.0 liter reactor such as illustrated in FIG. 5, 1210 g of 0.01 N HCl was tempered to 5° C. Out of the bottom valve of the reactor the water phase was circulated by the high shear mixer or with an auxiliary pump, preferred a rotary lobe pump, and then followed by the high shear mixer, back to the top of the reactor. The inlet of the recirculation into the reactor was under the fluid level in order to prevent foaming (see FIG. 5).
Precipitation
High Shear Mixer (HSM)
The tip speed of the rotor in the high shear mixer was set 25 m/sec. A rotor/stator combination with one teeth row, each for rotor and stator was used.
Dosing of the DMA Solution
The DMA solution tempered at 70° C. was dosed with a gear pump via an injector nozzle, which was pointing into the mixing chamber of the high shear mixer, into the circulating aqueous phase.
Dosing Rate of the DMA Solution
The DMA solution was dosed into the aqueous phase resulting in a ratio of HCl/DMA, in the mixing chamber of the high shear mixer of 100/1.
Additional Dispersing in the HSM (after Precipitation), Isolation and Washing
After addition of the DMA solution the obtained MBP suspension was dispersed for an additional time, corresponding to equivalents of the batch passing the high shear mixer. The time was corresponding to a turnover in calculated recirculation times of the batch of 6 times.
The obtained suspension, held at 5-10° C. was separated from the solid MBP. This was done by using a suction filter. The isolated MBP was washed with 0.01 N HCl (15 kg 0.01 N HCl/kg MBP) followed by washing with water (5 kg water/kg MBP) in order to remove the DMA. The isolated (wet) MBP had a water content between 60 and 70%.

Delumping and Drying

Prior to drying the (wet) MBP was delumped by using a sieve mill. The (wet) MBP was dried in a cabinet dryer. During the drying process of the MBP the temperature of the product was below 40° C. in order to avoid recrystallization of the API. The pressure inside the cabinet dryer was below 20 mbar. The water content of the MBP after drying was below 2.0% and was signed amorphous in the XRPD pattern.

Example 23

This example describes the spray dry formation of a solid molecular complex comprising Compound I and HPMC-AS.

Compound I is prepared with a polymer such as HPMCAS, optionally including a surfactant (e.g. an ionic surfactant such as sodium, 1,4-bis(2-ethylhexoxy)-1,4-dioxobutane-2-sulfonate (Docusate Sodium) or a nonionic surfactant such as Polysorbate 80). In general, a suitable solvent system, such as 20:80 (w/w) tetrahydrofuran:acetone is equilibrated to 30° C., and Compound I is added to a level of 2-10% solids in 4-6 portions with stirring. HPMCAS at a suitable ratio, for example 70:30 w/w HPMCAS:Compound I, is added (alternatively HPMCAS and surfactant at for example 65:5:30 HPMCAS:surfactant:Compound I) is added. The temperature is raised to 35-40° C., and the system optionally filtered to ensure removal of any unsolubilized solids. The solution is then spray dried to provide spherical particles with a size distribution of 1-20 microns. Further processing may include drying of the material in a fluid bed or tray dryer, and the resulting material may be densified, for example, by roller compaction. As an example, Compound I and HPMCAS in a ratio 30:70 (w/w) were dissolved to a level of 5.4% solids in a blend of 20:80 (w/w) tetrahydrofuran and acetone. The resulting solution was then spray dried to produce a solid dispersion, amorphous powder. The solution was spray dried using a suitable spray dryer, e.g., a GEA-Niro SDMICRO™ Spray Dryer for smaller batches (e.g. 10 gm solids) and a Niro Mobile Manor Spray Dryer for larger batches (e.g. 1 kg solids). For example, for a 10 gm batch, 35.0 gm of tetrahydrofuran was blended with 140.0 gm of acetone in a glass beaker, and 3.0 gm of Compound I was added with stirring for 10 minutes to dissolve; 7.0 gm of HPMCAS-L (Shin-Etsu grade NF) was then added and stirred. While the solids appeared to be dissolved, the solution was filtered through filter paper prior to spray drying. The solution was spray dried with the GEA-Niro SDMICRO™ Spray Dryer with inlet/outlet conditions of 85° C. and 55° C., respectively, with atomization gas pressure at 0.5 bar. The spray dried material was collected in the cyclone collector, 5.78 gm or 58% yield.

A 1.6 kg batch was also prepared, where the solution was prepared similarly, only instead of filtering, the solution was stirred overnight at room temperature to ensure all solids were dissolved. A 200 mesh screen was attached to the end of the feed hose to remove any un-dissolved particles and the solution was spray dried using the Mobile Manor Spray Dryer. The inlet/outlet conditions were 100° C. and 55° C., respectively, with atomization gas pressure at 1.0 bar, with gas flow rate of 90 kg/hr. The material was spray dried over two days, and material collected after the first day was subjected to vacuum drying at 45° C. to remove residual solvents. The collected material was assessed for bulk density (0.23 gm/mL), particle size (8 microns with a normal distribution and standard deviation of 3 microns), residual solvent (after 89 hours of vacuum drying, the large batch had residual solvents of 0.001% acetone and 0.017% tetrahydrofuran), polarized light microscopy, DSC (the DSC thermogram for the small batch shows an endothermic peak at approximately 243° C., while the thermogram for the large batch showed essentially no peak) and XRPD (which showed an amorphous material).

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to crystallization or co-crystallization conditions for Ret and Ret surrogate proteins and/or various kinase domain sequences can be used. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values That which is claimed is:

1. A crystalline polymorph Form 1 of Compound I:

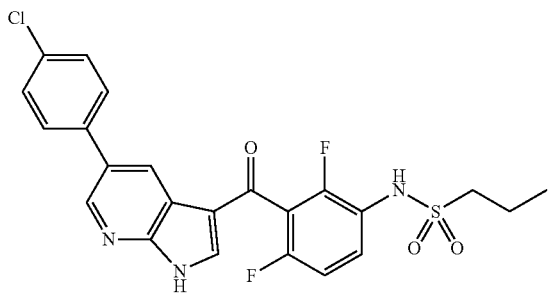 [SMILES: CCCS(=O)(=O)Nc1ccc(F)c(C(=O)c2c[nH]c3ncc(-c4ccc(Cl)cc4)cc23)c1F]

that exhibits a powder x-ray diffraction pattern having characteristic peak locations of approximately 4.7, 9.4, 11.0, 12.5, and 15.4 degrees 2θ.

2. A crystalline polymorph according to claim 1, wherein said polymorph exhibits a powder x-ray diffraction pattern having characteristic peak locations of approximately 4.7, 9.4, 10.0, 11.0, 12.5, 14.2, 15.4, 18.6, and 22.2 degrees 2θ.

3. A crystalline polymorph according to claim 1, wherein said polymorph exhibits a powder x-ray diffraction pattern having characteristic peak locations of approximately 4.7, 9.4, 10.0, 11.0, 12.5, 14.2, 15.4, 16.1, 18.6, 19.0, 22.2 and 26.8 degrees 2θ.

4. A crystalline polymorph according to claim 1, wherein said polymorph exhibits a powder x-ray diffraction pattern substantially the same as the powder x-ray diffraction pattern of FIG. 1.

5. A purified form of the crystalline polymorph of claim 1.

* * * * *

UNITED STATES PATENT AND TRADEMARK OFFICE
CERTIFICATE OF CORRECTION

PATENT NO. : 9,663,517 B2
APPLICATION NO. : 15/241773
DATED : May 30, 2017
INVENTOR(S) : Dipen Desai et al.

Page 1 of 1

It is certified that error appears in the above-identified patent and that said Letters Patent is hereby corrected as shown below:

On the Title Page

Item (73) Assignees, please replace "Hoffman-La-Roche Inc." with --Hoffmann-La Roche Inc.--.

Signed and Sealed this
Seventeenth Day of March, 2020

Andrei Iancu
*Director of the United States Patent and Trademark Office*